US012773488B2

(12) United States Patent
Baxter et al.

(10) Patent No.: US 12,773,488 B2
(45) Date of Patent: Oct. 27, 2026

(54) OPHTHALMIC SURGICAL CASSETTE

(71) Applicant: Alcon Inc., Fribourg (CH)

(72) Inventors: Vincent A. Baxter, Temecula, CA (US); Brad Hua Chen, Mission Viejo, CA (US); Satish Yalamanchili, Irvine, CA (US); Brian William McDonell, Irvine, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/771,616

(22) Filed: Jul. 12, 2024

(65) Prior Publication Data

US 2025/0025623 A1 Jan. 23, 2025

Related U.S. Application Data

(60) Provisional application No. 63/594,908, filed on Oct. 31, 2023, provisional application No. 63/514,428, filed on Jul. 19, 2023.

(51) Int. Cl.

*A61M 1/00* (2006.01)
*A61F 9/007* (2006.01)
*A61M 3/02* (2006.01)

(52) U.S. Cl.

CPC ........... *A61M 1/72* (2021.05); *A61F 9/00736* (2013.01); *A61M 1/77* (2021.05); *A61M 1/80* (2021.05); *A61M 1/804* (2021.05); *A61M 1/82* (2021.05); *A61M 3/0201* (2021.05); *A61M 2205/121* (2013.01); *A61M 2205/123* (2013.01); *A61M 2205/125* (2013.01); *A61M 2205/128* (2013.01); *A61M 2210/0612* (2013.01)

(58) Field of Classification Search

CPC ........ A61M 1/72; A61M 1/77; A61M 3/0201; A61M 2210/0612; A61M 2205/12; A61M 2205/123; A61M 2205/128; A61M 2205/121; A61M 1/82; A61M 2205/125; A61M 1/80; A61M 1/804; A61M 1/73; A61F 9/00736

See application file for complete search history.

(56) References Cited

U.S. PATENT DOCUMENTS

| | | | | |
|---|---|---|---|---|
| 4,713,051 | A | 12/1987 | Steppe et al. | |
| 4,735,610 | A | 4/1988 | Akkas et al. | |
| 4,758,238 | A | 7/1988 | Sundblom et al. | |
| 5,267,956 | A | 12/1993 | Beuchat | |
| 5,282,787 | A | 2/1994 | Wortrich | |
| 5,288,290 | A | 2/1994 | Brody | |
| 5,464,391 | A | 11/1995 | Devale | |
| 5,499,969 | A | 3/1996 | Beuchat et al. | |
| 5,735,307 | A | 4/1998 | Charron | |
| 5,746,719 | A * | 5/1998 | Farra | A61M 1/77 418/56 |
| 5,810,766 | A | 9/1998 | Barnitz et al. | |
| 6,036,458 | A | 3/2000 | Cole et al. | |
| 6,059,544 | A | 5/2000 | Jung et al. | |
| 6,319,223 | B1 | 11/2001 | Wortrich et al. | |

(Continued)

FOREIGN PATENT DOCUMENTS

DE 102018211347 A1 1/2020

*Primary Examiner* — Wesley G Harris

(74) *Attorney, Agent, or Firm* — Patterson + Sheridan, LLP

(57) ABSTRACT

Embodiments disclosed herein provide a surgical cassette that functions as an interface between a patient and a surgical console used to perform a variety of different ophthalmic surgeries.

20 Claims, 29 Drawing Sheets

(56) References Cited

U.S. PATENT DOCUMENTS

| | | | |
|---|---|---|---|
| 6,511,454 | B1 | 1/2003 | Nakao et al. |
| 6,561,999 | B1 | 5/2003 | Nazarifar et al. |
| 7,244,240 | B2 | 7/2007 | Nazarifar et al. |
| 7,326,183 | B2 | 2/2008 | Nazarifar et al. |
| 7,484,769 | B2 * | 2/2009 | Domash ................ A61M 39/12 285/401 |
| 7,524,299 | B2 | 4/2009 | Hopkins et al. |
| 7,559,914 | B2 | 7/2009 | Domash et al. |
| 7,594,901 | B2 | 9/2009 | Hopkins et al. |
| 7,713,237 | B2 | 5/2010 | Nazarifar et al. |
| 7,764,370 | B2 * | 7/2010 | Williams ............... A61B 50/10 356/246 |
| 7,872,746 | B2 | 1/2011 | Gao et al. |
| 7,956,341 | B2 | 6/2011 | Gao |
| 7,981,074 | B2 | 7/2011 | Davis et al. |
| 8,011,905 | B2 | 9/2011 | Artsyukhovich et al. |
| 8,202,243 | B2 | 6/2012 | Morgan |
| 8,343,100 | B2 | 1/2013 | King et al. |
| 8,398,582 | B2 | 3/2013 | Gordon et al. |
| 8,430,840 | B2 | 4/2013 | Nazarifar et al. |
| 8,500,421 | B2 | 8/2013 | Domash et al. |
| 8,545,198 | B2 | 10/2013 | Artsyukhovich et al. |
| 8,777,931 | B2 | 7/2014 | Davis et al. |
| 8,939,927 | B2 | 1/2015 | Sorensen et al. |
| 9,119,699 | B2 | 9/2015 | Gordon |
| 9,119,701 | B2 | 9/2015 | Gordon |
| 9,121,509 | B2 | 9/2015 | Williams |
| 9,132,229 | B2 | 9/2015 | Gao |
| 9,295,765 | B2 | 3/2016 | Muri et al. |
| 9,314,553 | B2 | 4/2016 | Gordon et al. |
| 9,517,162 | B2 | 12/2016 | Huculak et al. |
| 9,549,850 | B2 | 1/2017 | Sorensen et al. |
| 9,561,321 | B2 | 2/2017 | Sorensen et al. |
| 9,931,447 | B2 | 4/2018 | Layser et al. |
| 10,052,228 | B2 | 8/2018 | Boukhny et al. |
| 10,314,741 | B2 | 6/2019 | Sorensen et al. |
| 10,314,953 | B2 | 6/2019 | Ovchinnikov et al. |
| 10,363,111 | B2 | 7/2019 | Fung et al. |
| 10,537,471 | B2 | 1/2020 | Bourne et al. |
| 10,729,581 | B2 | 8/2020 | Boukhny et al. |
| 11,045,354 | B2 | 6/2021 | Sorensen et al. |
| 11,602,586 | B2 | 3/2023 | Bourne et al. |
| 11,877,952 | B2 | 1/2024 | Sorensen et al. |
| 11,878,105 | B2 | 1/2024 | Baxter et al. |
| 12,004,823 | B2 | 6/2024 | Carbone et al. |
| 12,070,417 | B2 | 8/2024 | Gao et al. |
| 2004/0227736 | A1 | 11/2004 | Kamrath et al. |
| 2005/0166681 | A1 | 8/2005 | Onoda et al. |
| 2005/0245888 | A1 | 11/2005 | Cull |
| 2007/0100316 | A1 | 5/2007 | Traxinger |
| 2007/0180903 | A1 | 8/2007 | Gao |
| 2007/0180904 | A1 | 8/2007 | Gao |
| 2007/0232990 | A1 * | 10/2007 | Hopkins ................... G01F 1/66 604/30 |
| 2008/0082040 | A1 | 4/2008 | Kubler et al. |
| 2008/0082077 | A1 | 4/2008 | Williams |
| 2008/0097284 | A1 * | 4/2008 | Gao ........................ A61M 1/72 604/30 |
| 2008/0125697 | A1 | 5/2008 | Gao |
| 2008/0147023 | A1 | 6/2008 | Hopkins et al. |
| 2009/0030372 | A1 | 1/2009 | Finodeyev |
| 2010/0125257 | A1 | 5/2010 | Perkins et al. |
| 2010/0152685 | A1 | 6/2010 | Goh |
| 2010/0286651 | A1 * | 11/2010 | Sorensen ................ A61M 1/82 604/151 |
| 2011/0100129 | A1 | 5/2011 | Gruhler |
| 2011/0295195 | A1 | 12/2011 | Perkins et al. |
| 2011/0313343 | A1 | 12/2011 | Milutinovic et al. |
| 2012/0041362 | A1 | 2/2012 | Gerg et al. |
| 2012/0330254 | A1 | 12/2012 | Walter et al. |
| 2013/0245543 | A1 * | 9/2013 | Gerg ....................... A61M 1/77 604/30 |
| 2014/0213993 | A1 | 7/2014 | Kuebler et al. |
| 2015/0174314 | A1 | 6/2015 | Shener et al. |
| 2015/0250939 | A1 | 9/2015 | Kuntz et al. |
| 2015/0282985 | A1 | 10/2015 | Ross et al. |
| 2015/0335797 | A1 | 11/2015 | Muri et al. |
| 2016/0166742 | A1 | 6/2016 | Layser et al. |
| 2016/0220751 | A1 | 8/2016 | Mallough et al. |
| 2017/0189231 | A1 | 7/2017 | Baxter et al. |
| 2018/0318131 | A1 | 11/2018 | Boukhny et al. |
| 2019/0041284 | A1 | 2/2019 | Giessbil |
| 2019/0099546 | A1 | 4/2019 | Keh et al. |
| 2019/0143008 | A1 | 5/2019 | Brundage et al. |
| 2019/0184072 | A1 | 6/2019 | Madden et al. |
| 2019/0255231 | A1 | 8/2019 | Koppel et al. |
| 2020/0054802 | A1 | 2/2020 | Koppel et al. |
| 2020/0237976 | A1 | 7/2020 | Hickey |
| 2020/0348164 | A1 | 11/2020 | Dam-Huisman |
| 2021/0178033 | A1 | 6/2021 | Nazarifar et al. |
| 2021/0178034 | A1 * | 6/2021 | Nazarifar ............ A61M 3/0201 |
| 2022/0031928 | A1 | 2/2022 | Fineout et al. |

* cited by examiner

OPHTHALMIC SURGICAL CASSETTE

CROSS-REFERENCE TO RELATED APPLICATIONS

This application claims benefit of and priority to U.S. Provisional Patent Application No. 63/594,908, filed Oct. 31, 2023, and U.S. Provisional Patent Application No. 63/514,428, filed Jul. 19, 2023. The entire contents of each of these applications are incorporated herein by reference.

INTRODUCTION

Ophthalmic surgeries may be performed on an anterior or a posterior portion of a patient's eye, depending upon the specific procedure and the patient's condition. One such anterior procedure includes cataract surgery, which involves removing a cataractous lens and replacing the lens with an artificial intraocular lens (IOL). The cataractous lens is typically removed by fragmenting the lens and aspirating the lens fragments out of the eye. The lens may be fragmented using, e.g., a phacoemulsification probe, a laser probe, or another suitable instrument. During the procedure, the probe fragments the lens, and the fragments are aspirated out of the eye through, e.g., a hollow needle or cannula. Throughout the procedure, irrigating fluid is pumped into the eye to maintain an intraocular pressure (IOP) and prevent collapse of the eye.

During cataract surgery, for example, a surgical cassette having one or more peristaltic and/or venturi pumps and one or more valve assemblies may be operably coupled with a fluidics module of a surgical console and used to facilitate the aspiration and irrigation functionalities described above. In general, the one or more valve assemblies of the surgical cassette are operable to control the application of pressure and vacuum generated by the one or more peristaltic pumps during the surgical procedure.

However, conventional surgical cassettes have a number of significant shortcomings including, for example, relatively tight sealing tolerances, relatively high torque required for valve operation, restricted flow capacity, the inability to maintain a secure connection with the surgical console, relatively high fabrication costs and complexity, undesirable fluid displacement during valve operation, and redundancy issues, among others.

Therefore, there is a need for improved surgical cassettes which address at least some of the drawbacks described above.

BRIEF SUMMARY

The present disclosure relates generally to ophthalmic surgical cassettes, valve assemblies therefor, and methods of use thereof.

In certain embodiments, a surgical cassette is provided for ophthalmic irrigation/infusion and/or aspiration/suction during a surgical procedure, the surgical cassette including a base, and a cover coupled to the base, the cover including at least one port in fluid communication with at least one of the plurality of channels disposed in the base. In certain embodiments, a manifold is coupled to the cover, the manifold forming at least one channel with an outer surface of the cover. In certain embodiments, the base includes at least one pump assembly disposed in the base, a plurality of channels in fluid communication with the at least one pump assembly, and one or more valve assemblies disposed in the base and configured to control fluid communication between the plurality of channels of the base, wherein one or more of the channels is in fluid communication with a source of pressure or vacuum The following description and the related drawings set forth in detail certain illustrative features of one or more embodiments.

BRIEF DESCRIPTION OF THE DRAWINGS

The appended figures depict certain aspects of one or more disclosed embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1A:
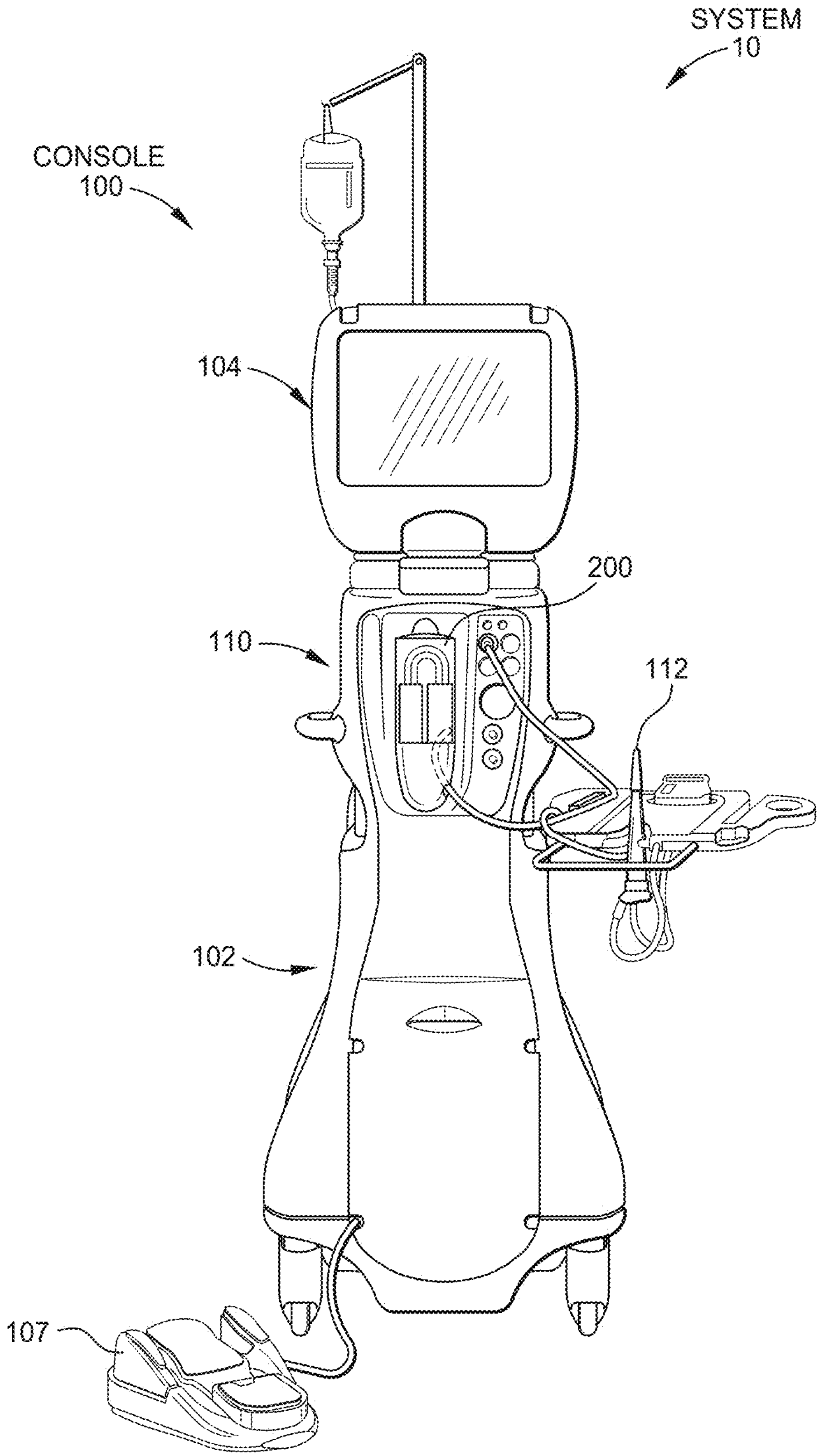
FIG. 1A illustrates an example of an ophthalmic surgical system that may be used to perform ophthalmic procedures on an eye, according to certain embodiments.

The present disclosure relates generally to ophthalmic surgical cassettes and methods of use thereof.

Conventional ophthalmic surgical cassettes and systems have a number of significant shortcomings, including a lack of compatibility for both anterior and posterior surgical procedures. Currently, there is a performance and feature set discrepancy between anterior and posterior ophthalmic surgical cassettes and systems. Some surgical cassettes offer good posterior performance and feature sets, but are large, overly complicated, and lack the requisite fluidic performance for anterior procedures. For example, the ability of such cassettes to mitigate post occlusion break surge is limited, or even absent. Meanwhile, other cassettes offer excellent anterior procedure fluidic performance (including fast response to, and mitigation of, post occlusion break surge), but do not provide larger feature sets for posterior surgical procedures. For example, such cassettes do not support fluid air exchange operations, which require high suction flow rates as provided by, e.g., venturi pumps, nor do they support simultaneous use of both a vitrectomy probe and a phacoemulsification handpiece. There also remains room for fluidics improvement of current anterior surgical systems, such as to reduce surge disturbances in the eye by further increasing response and flow capabilities.

Other performance limitations for both anterior and posterior surgical systems include irrigation/infusion flow accuracy, pressure/vacuum sensor sensitivity to mechanical disturbances, interference fit valves with high operational torque, valves with limited fluid flow capacity, complex fluidic schematics with large fluid volumes in fluidic communication to the eye during venting operations, and large cassette layouts to support the complexity of reservoirs, sensors, valves, pumps, and accessory connections, among others.

The present disclosure provides improved surgical cassettes that address the drawbacks described above.

Certain embodiments disclosed herein provide a surgical cassette that functions as an interface between a patient and a surgical console used to perform a variety of different ophthalmic surgeries. For example, the surgical cassette, in conjunction with the surgical console and its associated console fluidics module, can be utilized for maintaining surgical space within the patient's eye via fluidics balancing during anterior and posterior ophthalmic surgical procedures.

Certain embodiments disclosed herein provide greater flexibility in the layout of the surgical cassette including, e.g., the arrangement of valve assemblies, the flow channels therein, and a manifold which optimizes the surgical cassette for anterior surgical procedures, posterior surgical procedures, or a combination thereof. For example, when compared to conventional surgical cassettes, certain embodiments disclosed herein provide greater flexibility by including different manifolds, each of which include different flow connections that configure the surgical cassette for a specific ophthalmic procedure.

Certain embodiments disclosed herein provide improved valve operation including increased flow capacity and ability to relieve pressure or vacuum to one port without inducing a significant pressure or vacuum disturbance to another port, which is beneficial for post-occlusion break surge mitigation. In certain embodiments, dual path venting is enabled to provide venting to two separate channels simultaneously and individually.

In particular embodiments, a surgical cassette for ophthalmic irrigation/infusion and/or aspiration/suction during a surgical procedure is provided, the surgical cassette including a base, and a cover coupled to the base, the cover including at least one port in fluid communication with at least one of the plurality of channels disposed in the base. In certain embodiments, a manifold is coupled to the cover, the manifold forming at least one channel with an outer surface of the cover. In certain embodiments the base includes at least one pump assembly disposed in the base, a plurality of channels in fluid communication with the at least one pump assembly, and one or more valve assemblies disposed in the base and configured to control fluid communication between the plurality of channels of the base, wherein one or more of the channels is in fluid communication with a source of pressure or vacuum In particular embodiments, a rotatable aspiration valve of a surgical cassette is provided, the rotatable aspiration valve including a plurality of ports, the plurality of ports including a first port, a second port, and a third port. The first port is in fluidic communication with an aspirating handpiece, the second port is in fluidic communication with an aspirating pump disposed within a base of the surgical cassette, and the third port is in fluidic communication with a fluid chamber formed between the base and a cover of the surgical cassette. The aspiration valve is configured to form at least one valve pathway in the surgical cassette. The aspiration valve is further switchable from a first state to a second state. In the first state, the aspiration valve fluidically connects the aspirating handpiece to the aspirating pump. In the second state, the aspiration valve fluidically connects the aspirating handpiece to the fluid chamber for venting a fluidic volume in fluidic communication with the aspirating handpiece. In certain embodiments, the aspiration valve is configured to have a first valve pathway and a second valve pathway. In such embodiments, in the second state, the aspiration valve connects the first valve pathway, which connects from the aspirating handpiece to the fluid reservoir, with the second valve pathway, which connects the aspirating pump to the fluid reservoir, for separate venting of the fluidic volume in fluidic communication with the aspiration pump.

In particular embodiments, a surgical cassette for ophthalmic irrigation/infusion and/or aspiration/suction during a surgical procedure is provided. The surgical cassette includes a base. The base is configured to adjoin to a first cover to facilitate anterior surgical performance, or to adjoin to a second cover to facilitate both anterior and posterior surgical performance.

Generally, the surgical cassettes described herein provide an improvement of fluidics performance (including surge mitigation) for both anterior and posterior procedures in a size reduced form factor, which is facilitated by, for example: a low, exposed vent volume fluidic arrangement; one or more vent valve ports positioned directly over a fluidic chamber; dual vent and low friction valves; alignment features disposed around pressure sensor diaphragms that engage pressure sensors for stable pressure readings; pressure sensors positioned at the center of pumps, adjacent irrigation and aspiration pumps; four face-sealed valve assemblies positioned in corner placements of the cassettes; a fluidic chamber with fluid-directing baffling; a total internal reflection fluid level sensor with barcode reading capabilities; a venturi port providing air connection from the fluidic chamber to a venturi pump in a surgical console; an air filter with drain mitigation between a venturi port and fluid chamber; and, a redundant irrigation pressure sensor in fluidic communication with an irrigation pump and first irrigation pressure sensor. These features, as well as others, are described below in more detail.

FIG. 1A illustrates an example of an ophthalmic surgical system 10 that may be used to perform ophthalmic procedures on an eye, according to certain embodiments. In the illustrated embodiments, system 10 includes console 100 (also referred to as a "surgical console"), a housing 102, a display screen 104, an interface device 107 (e.g., a foot pedal), a fluidics subsystem 110, and a handpiece 112, coupled as shown and described in more detail with reference to FIG. 1B.

Figure 1B:
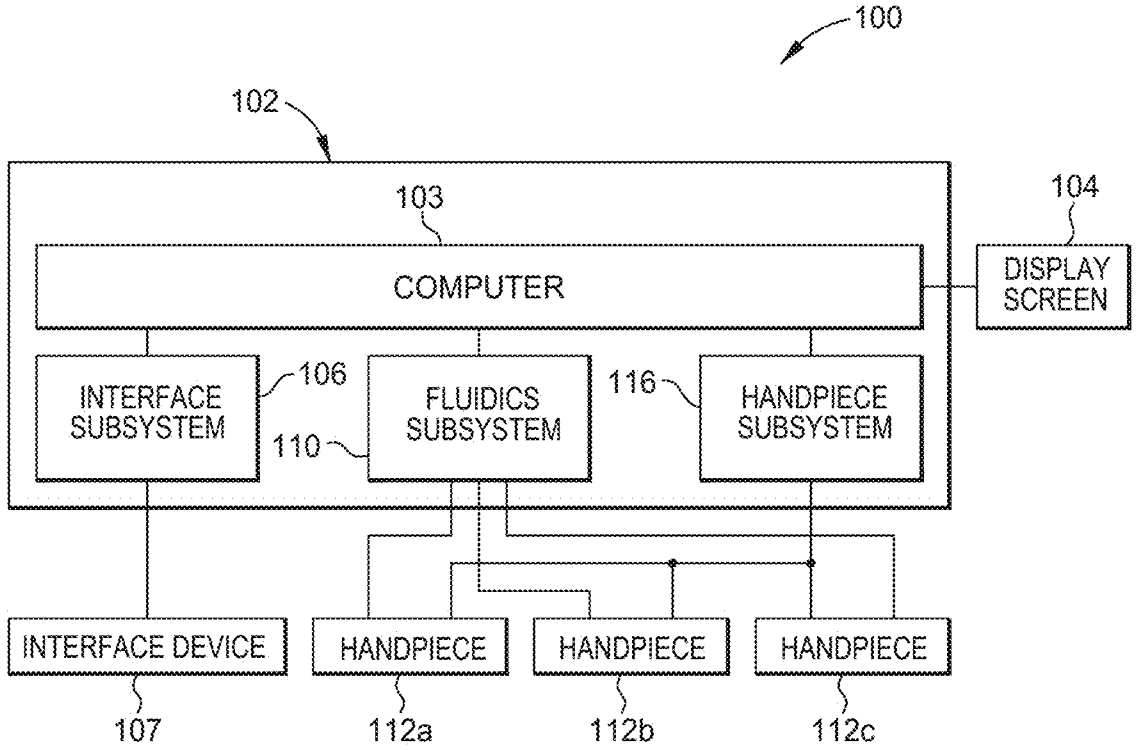
FIG. 1B is an example of subsystems of a console of the ophthalmic surgical system of FIG. 1A, according to certain embodiments.

FIG. 1B is an example of subsystems of console 100 of ophthalmic surgical system 10 of FIG. 1A, according to certain embodiments. Console 100 includes housing 102, which accommodates a computer 103 (with an associated display screen 104) and subsystems 106, 110, and 116, which support interface device 107 and handpieces 112 (112*a-c*). An interface device 107 receives input to surgical system 10, sends output from system 10, and/or processes the input and/or output. Examples of an interface device 107 include a foot pedal, manual input device (e.g., a keyboard), and a display. Interface subsystem 106 receives input from and/or sends output to interface device 107.

Handpiece 112 may be any suitable ophthalmic surgical instrument, e.g., an ultrasonically driven phacoemulsification (phaco) handpiece, a laser handpiece, an irrigating cannula, a vitrectomy handpiece, or another suitable surgical handpiece. Fluidics subsystem 110 provides fluid control for one or more handpieces 112 (112*a-c*). For example, fluidics subsystem 110 may manage fluid for an irrigating cannula. Handpiece subsystem 116 supports one or more handpieces 112. For example, handpiece subsystem 116 may manage ultrasonic oscillation for a phaco handpiece, provide laser energy to a laser handpiece, control operation of an irrigating cannula, and/or manage features of a vitrectomy handpiece.

Computer 103 controls operation of ophthalmic surgical system 10. In certain embodiments, computer 103 includes a controller that sends instructions to components of system 10 to control system 10. A display screen 104 shows data provided by computer 103.

Figure 2:
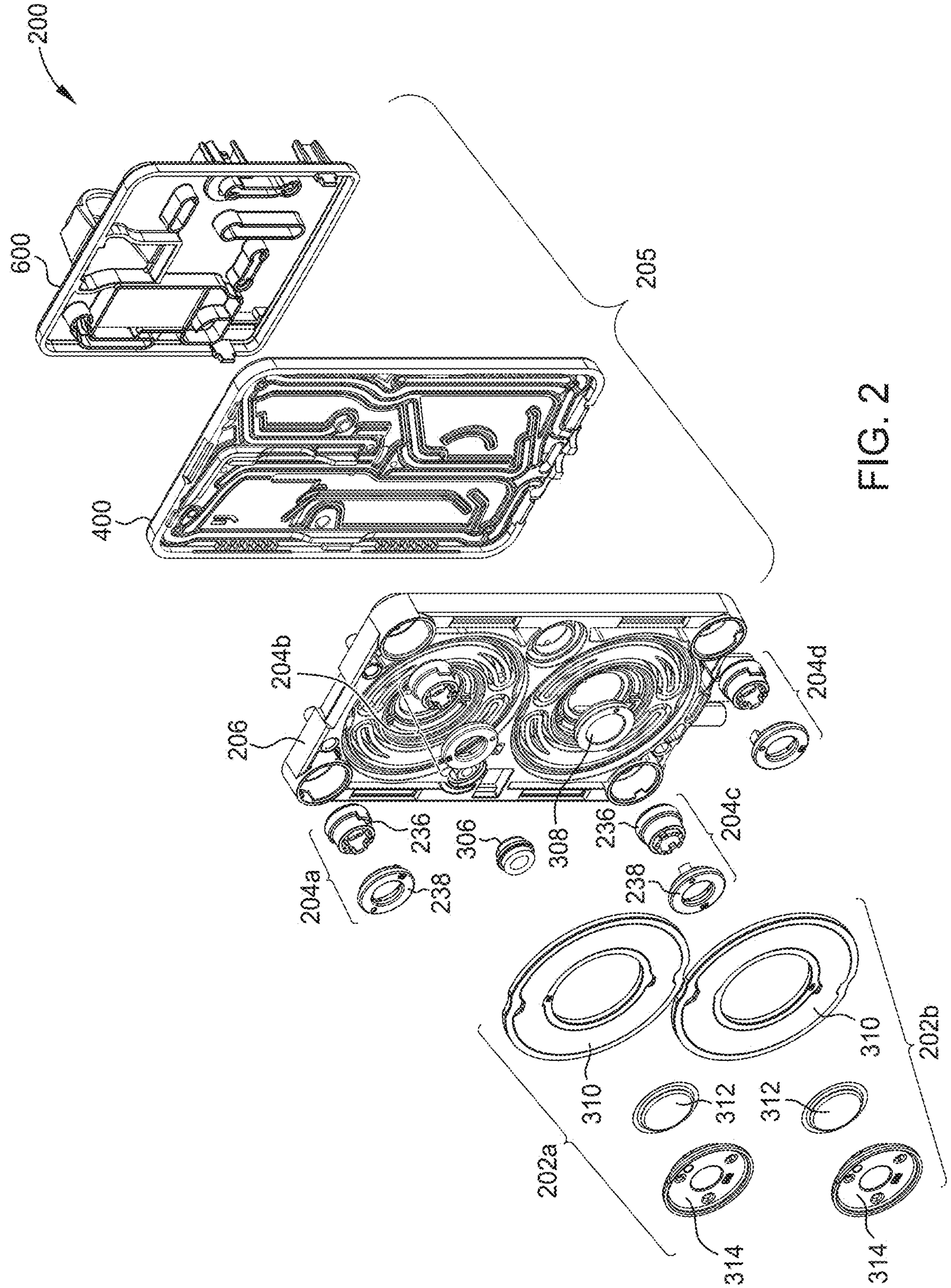
FIG. 2 is an exploded perspective view of an example surgical cassette including a base, a cover, and a manifold, according to certain embodiments.

FIG. 2 is an exploded perspective view of a cassette 200, which may be operably coupled to a console of an ophthalmic surgical system (e.g., console 100 of ophthalmic surgical system 10 illustrated in FIGS. 1A-1B), according to certain embodiments. The cassette 200 has a housing 205, which includes a base 206 and a cover 400 that is coupled to a frontside of the base 206. A manifold 600 is further coupled to a front facing surface of the cover 400. The manifold 600, also referred to as a "handle," may serve, in part, to identify and/or determine a configuration or type of the surgical cassette 200, and/or provide a physical handle or gripping service for a user. Disposed on a backside of the base 206 are a plurality of valve assemblies 204*a-d* arranged at each of the four corners of the base 206, and a plurality of pump assemblies 202*a-b* that are disposed in a stacked, central location relative to the base 206. The backside of the base 206 is configured to interact with the surgical console 100, while the frontside of the base 206 provides an interface for engagement with the cover 400 and/or manifold 600. Each of the plurality of valve assemblies 204*a-d* comprises both a valve body 302 and a valve-retaining ring 304. Each of the plurality of pump assemblies 202*a-b* comprises a pump elastomer 310, a diaphragm 312, and a diaphragm retainer ring 314. Also disposed within the backside of the base 206 is a venturi port seal 306 and a pressure sensor seal 308.

Figure 3B:
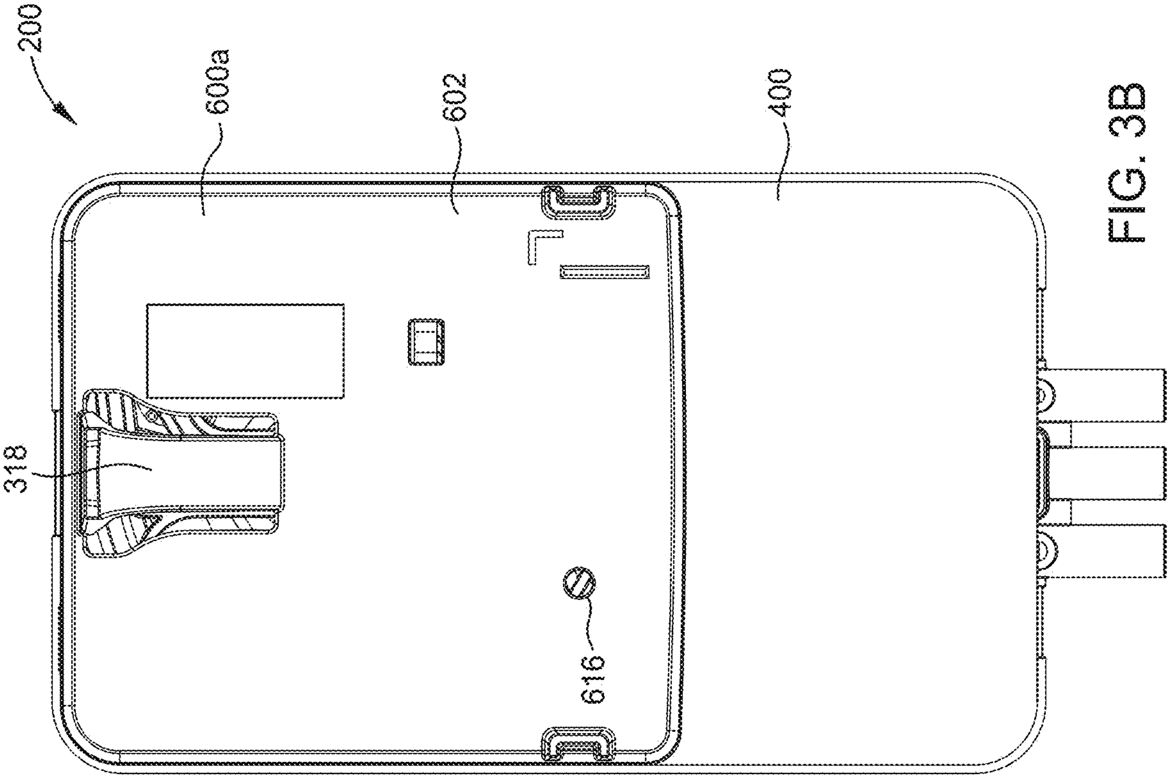
FIG. 3B is a frontside elevation view of the example surgical cassette of FIG. 3A, according to certain embodiments.
Figure 3A:
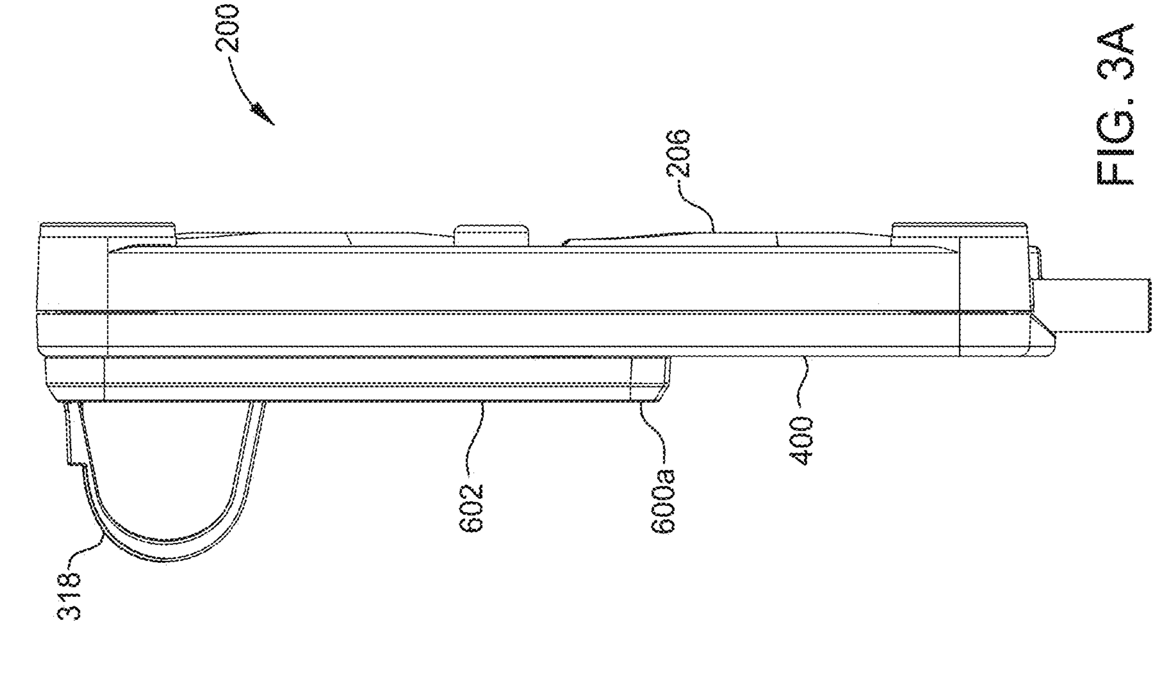
FIG. 3A is a right side elevation view of an example surgical cassette including a manifold that is configured to be used during surgical procedures on an anterior portion of an eye, according to certain embodiments.

FIGS. 3A and 3B show a right side view and a front view, respectively, of the cassette 200 when the base 206 and the cover 400 have been assembled with a manifold 600*a* that configures or specializes the cassette 200 for anterior eye procedures, according to certain embodiments. The manifold 600*a* comprises a substantially smooth outer surface 602 and an ergonomic finger loop 318, or handle, which provides the user an easy way to grip the manifold 600*a* when coupling and decoupling the cassette 200 to and from the surgical console 100.

Figure 4B:
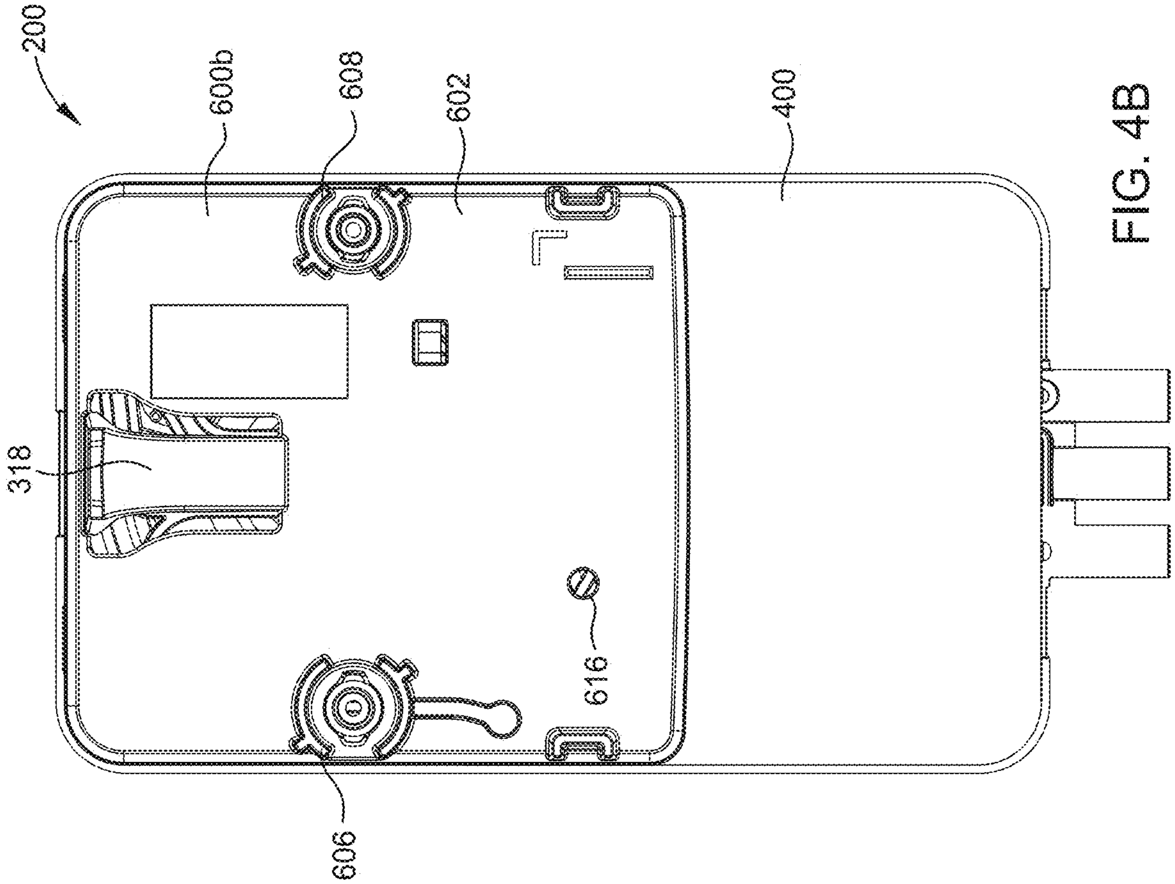
FIG. 4B is a frontside elevation view of the example surgical cassette of FIG. 4A, according to certain embodiments.
Figure 4A:
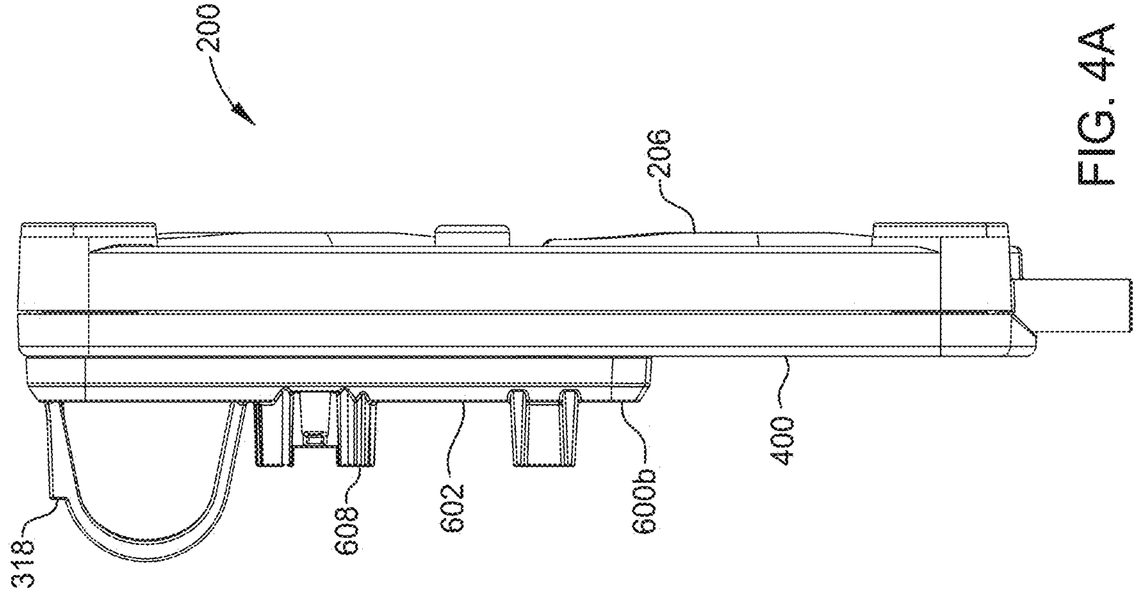
FIG. 4A is a right side elevation view of an example surgical cassette including a manifold that is configured to be used during surgical procedures on a posterior portion of an eye, according to certain embodiments.

In certain other embodiments, the cassette 200 may comprises a manifold 600*b*, which configures or specializes the cassette 200 for posterior eye procedures, according to certain embodiments. For example, as seen in the right side view and front view of FIGS. 4A and 4B respectively, the manifold 600*b* comprises a suction connector 608 and an infusion connector 606 disposed on its outer surface 602 and defined therethrough, as detailed further below with respect to FIGS. 8A and 8B.

Both the anterior manifold 600*a* and the posterior manifold 600*b* comprise an outer surface 602 that comprises a plurality of features that facilitate the directing of fluid flow and which are further described in more detail below with respect to FIGS. 7A-8B. It should be noted that, in certain embodiments, the anterior manifold 600*a* and the posterior manifold 600*b* are identical save for the posterior manifold 600*b* comprising the additional features related to the infusion connector 606 and the suction connector 608, while the anterior manifold 600*a* does not. For clarity purposes, both the anterior manifold 600*a* and the posterior manifold 600*b* will be referred to as the manifold 600 generally, except where such differentiating features are discussed.

Figure 5A:
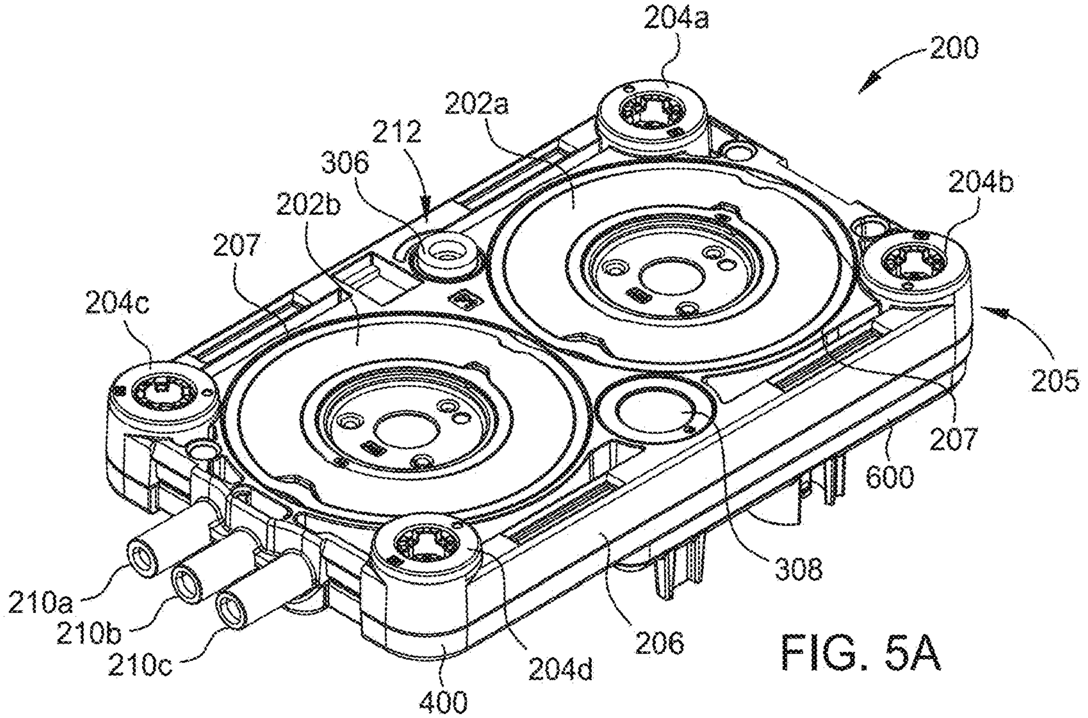
FIG. 5A is a backside isometric view of an example surgical cassette which may be operably coupled to a console of an ophthalmic surgical system, according to certain embodiments.
Figure 5B:
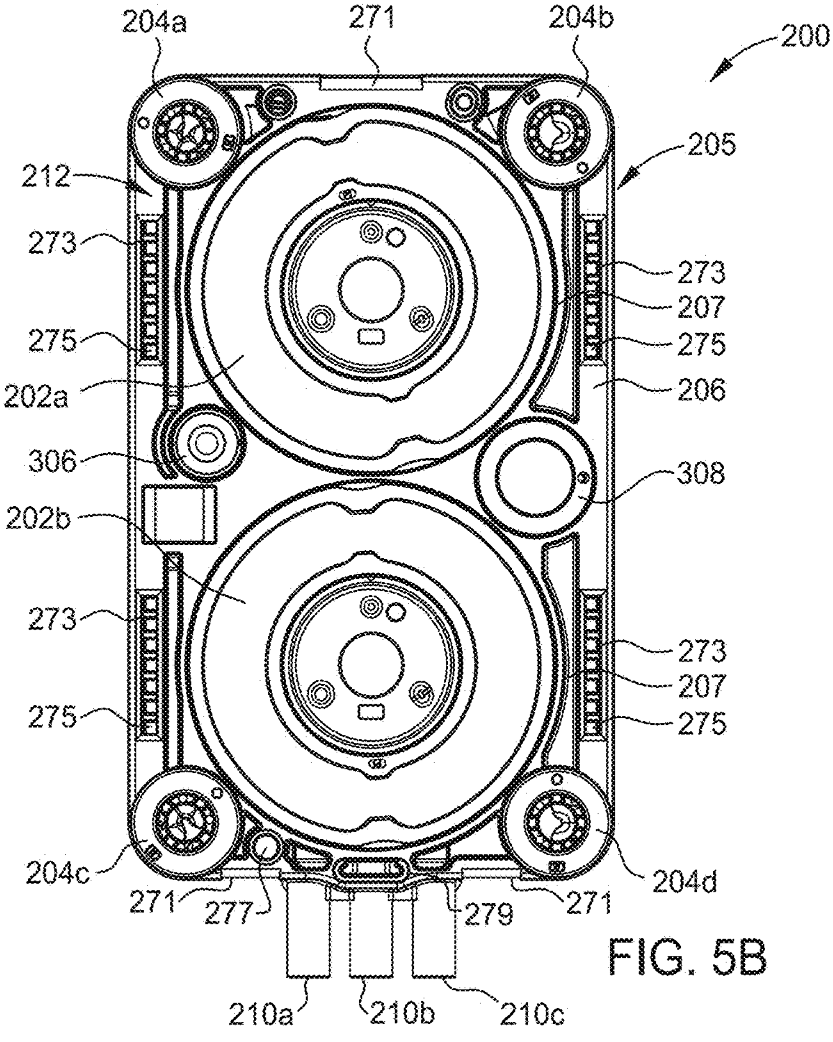
FIG. 5B is a backside elevation view of the surgical cassette of FIG. 2A, according to certain embodiments.

FIG. 5A is a backside isometric view of an example of the base 206 of surgical cassette 200 which may be operably coupled to a console of an ophthalmic surgical system (e.g., console 100 of ophthalmic surgical system 10 illustrated in FIGS. 1A-1B), according to certain embodiments. FIG. 5B is a backside elevation view of the surgical cassette 200 of FIG. 5A, according to certain embodiments. FIGS. 5A-5B are described together herein for clarity. Surgical cassette 200 includes two central and adjacent pump assemblies 202 (202*a-b*), which provide a source of pressure and/or vacuum, and four valve assemblies 204 (204*a-d*), each adjacent to a pump assembly and adjacent to two cassette edges, where the four valve assemblies control pressure and/or fluid communication within surgical cassette 200. In certain other embodiments, there may be only one pump assembly or more than two pump assemblies. In certain other embodiments, there may be more or less than four valve assemblies (e.g., two to six valve assemblies).

In certain embodiments, each of the pump assemblies 202 is disposed within a pump landing 207, or recess, formed in the base 206. The pump landing 207 may include one or more features for coupling the pump assembly 202 to the base 206, in addition to one or more fluid channels configured to facilitate the provision of pressure or vacuum to the surgical cassette 200.

In certain embodiments, and as further described below, surgical cassette 200 may also include two pressure sensor diaphragms 312 and two diaphragm retaining rings 314, each located at the center of a corresponding pump assembly 202, where the pressure sensor diaphragms 312 are used to allow measurement of pressure and/or vacuum within the surgical cassette 200. In certain embodiments, the diaphragm retaining rings 314 incorporate alignment features for engagement to pressure sensors on the console 100. The alignment features may be conical and recessed or may be a group of features including a conical recess, a v-groove recess, and a flat surface positioned around the center of the diaphragm 312. In certain embodiments, an elastomer diaphragm for redundant pressure measurement is disposed adjacent to the two pump assemblies 202.

In certain embodiments, an external source of pressure and/or vacuum is coupled to surgical cassette 200. In such embodiments, the external source may be either in place of or in addition to pump assemblies 202. In certain embodiments, the external source makes a fluidic connection from the console 100 to the surgical cassette 200 through a venturi port with an elastomer seal, described in more detail below, on the face of the surgical cassette 200.

Surgical cassette 200 has the housing 205, including the base 206, the cover 400 coupled to base 206, and the manifold 600 coupled to the cover 400. The base 206 has a plurality of inlet/outlet ports 210 including an aspiration port 210*a*, admin port 210*b*, and irrigation port 210*c*, which provide pressure and/or fluid communication between inside and outside of the housing 205. Fluid lines (e.g., tubing) may be coupled between each port 210*a-c* and a corresponding component of fluidics subsystem 110 and/or a corresponding handpiece 112*a-c* (shown in FIGS. 1A-1B). In certain embodiments, the base 206 and cover 208 form a rectangular shape with rounded corners, allowing the base 206 and cover 208 to circumscribe up to four valves, one at each of the rounded corners.

In certain embodiments, one of a first pump assembly 202*a* or second pump assembly 202*b* provides a source of pressure (e.g., to create a driving force for fluid irrigation), while the other one of the first pump assembly 202*a* or second pump assembly 202*b* provides a source of vacuum (e.g., to create suction for fluid aspiration) within surgical cassette 200. The first pump assembly 202*a* and second pump assembly 202*b* may be peristaltic pumps or any other suitable type of pump for generating pressure and/or vacuum. In certain embodiments, each of the first pump assembly 202*a* and the second pump assembly 202*b* is configured to engage with one or more rollers of a roller pump disposed on a surgical console, such as console 100. For example, when the surgical cassette 200 is coupled to the console 100, the pump elastomer 310 of each pump assembly 202*a*, 202*b* may be contacted against one or more rollers of a roller pump on the console 100. Thereafter, during use, manual forces provided by the rollers rolling along and pressing against the pump elastomers 310, as driven by the pump, may drive fluid within the corresponding pump assembly 202*a* or 202*b*, and thus surgical cassette 200, to generate pressure or vacuum as needed.

In certain embodiments, the first pump assembly 202*a* and second pump 202*b* assembly are identical to each other. For example, the pump elastomer 310 of each pump assembly 202*a*, 202*b* comprises a dual segmented volume that cancels pressure pulsations and is comprised of a two-shot manufacturing design, i.e., silicone rubber or other elastomeric material over a plastic substrate. However, the pump elastomer 310 may further comprise more or less than two segmented volumes (e.g., one to four or more segments).

Valve assemblies 204 are coupled to base 206. Valve assemblies 204 function cooperatively to control pressure and/or fluid communication within and through surgical cassette 200. In the illustrated embodiments, surgical cassette 200 includes a first or bypass valve assembly 204*a*, a second or suction valve assembly 204*b*, a third or irrigation valve assembly 204*c*, and a fourth or venting valve assembly 204*d*. As shown, in the embodiments of FIG. 5A, the four valve assemblies 204 are arranged at the four corners of housing 205 and surrounding the two pump assemblies 202, which are arranged towards a center of housing 205. However, in certain other embodiments, pump assemblies 202 and valve assemblies 204 may have any other suitable arrangement.

In certain embodiments, valve assemblies 204 may be operated to route fluid flow selectively between multiple channels of housing 205, as described in more detail below with respect to FIGS. 9A and 9B. For example, first valve assembly 204*a* and third valve assembly 204*c* may be in pressure and/or fluid communication with first pump assembly 202*a* and port 210*a* to provide aspiration through port 210*a*, and/or irrigation through an infusion port outlet disposed on the manifold 600 during an operation, and second valve assembly 204*b* and fourth valve assembly 204*d* may be in pressure and/or fluid communication with second pump assembly 202*b* and port 210*c* to provide irrigation through port 210*c* during the same operation. In certain embodiments, port 210*b* is an administration port, and fluid that is to be sent to the patient's eye via the port 210*c* may be first flowed into the cassette 200 via the admin port 210*b*. In certain embodiments, port 210*b* may be an auxiliary port, which is inactive during the operation and instead may be used to provide maintenance access for servicing surgical cassette 200 between operations.

The surgical cassette 200 further incorporates clamping and alignment features for mechanical coupling to the console. In certain embodiments, two pairs of vertical clamping slots 273 are disposed symmetrically about the adjacent pump assemblies 202 in the base 206. Clamping pads 275 may be disposed internally in the base 206 at each end of the clamping slots 273 and provide contact points for a clamping mechanism within the console 100. In certain embodiments, a hole 277 and/or a slot 279 are disposed near the lower and/or upper edges of the base 206, which engage and align with pins in the console 100 when the surgical cassette 200 is clamped thereto. Retaining features 271 are disposed at the top and bottom edges of the base 206 and may interface with spring loaded retaining arms in the console to keep the surgical cassette secured after the clamp is disengaged.

Figure 6A:
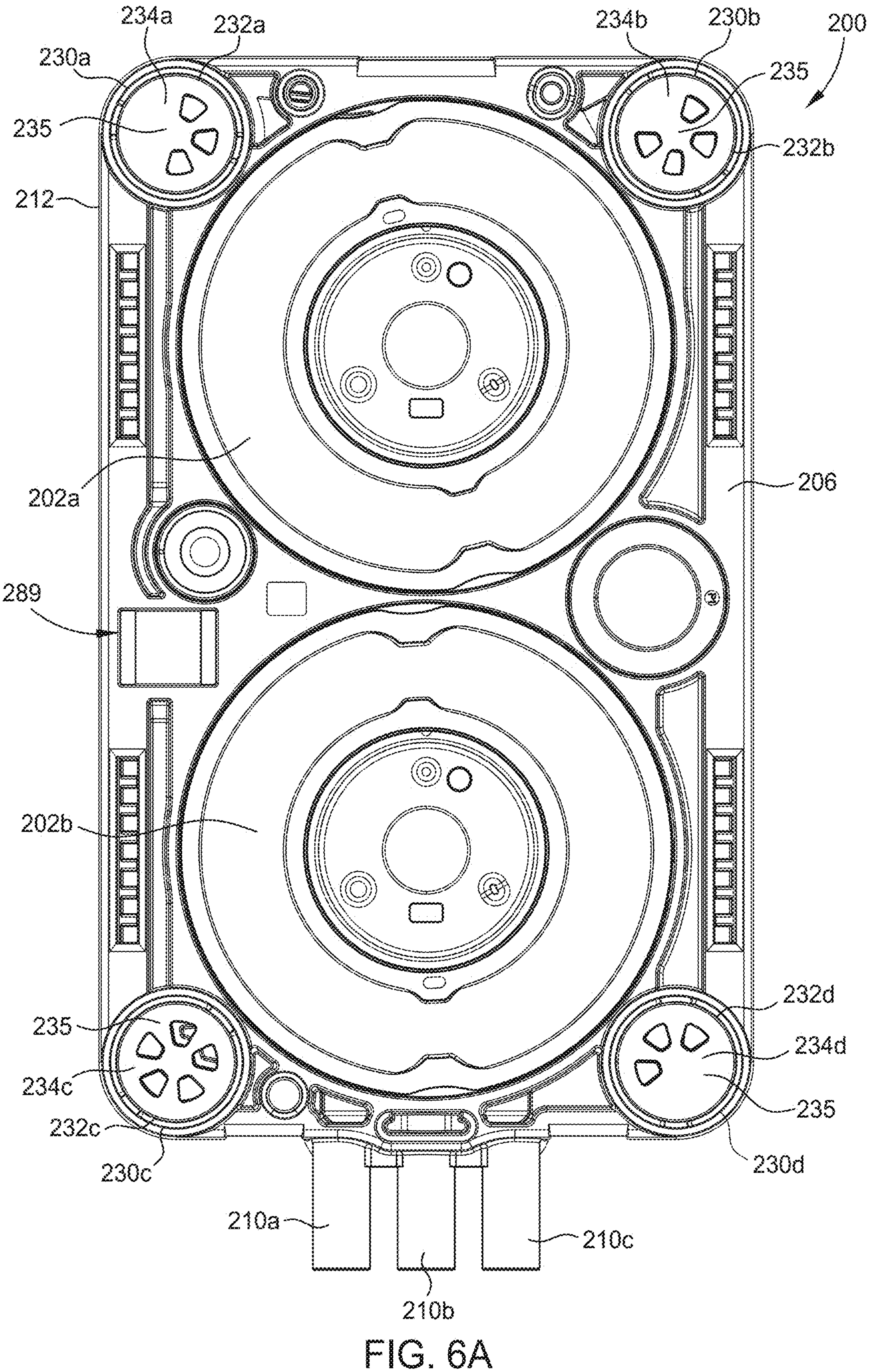
FIG. 6A is a back elevation view of the base portion of the surgical cassette of FIG. 5B with the valve assemblies removed, according to certain embodiments.

Greater detail of the base 206 may be had from FIGS. 6A-D. FIG. 6A is the same backside elevation view of surgical cassette 200 seen in FIG. 5B with the valve assemblies 204*a-d* removed from the base 206 to show corresponding backside surfaces 234*a-d* disposed there beneath.

Figure 6B:
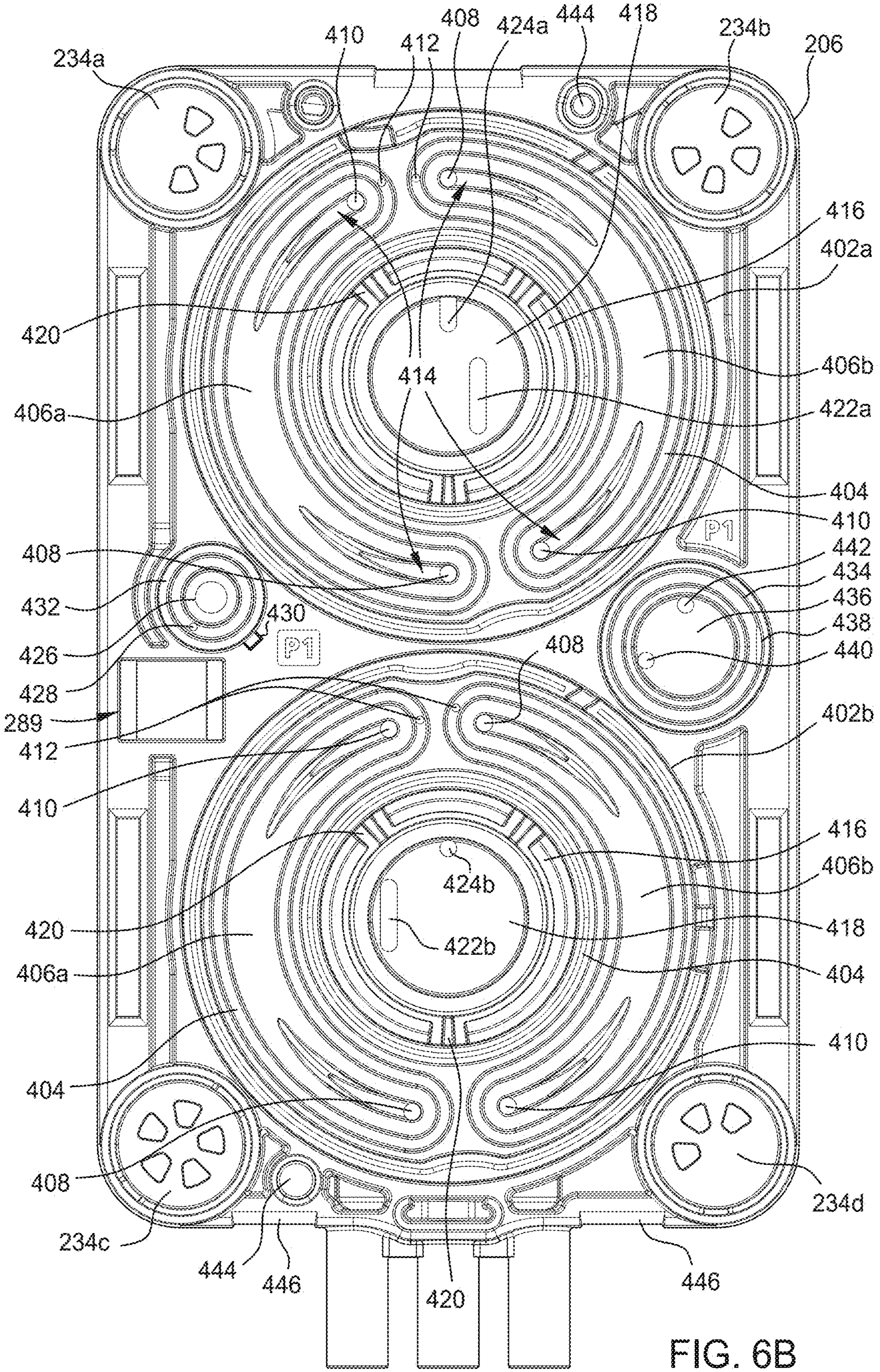
FIG. 6B is a back elevation view of the base of the surgical cassette of FIG. 6A with the pump assemblies, the pressure sensor seal, and the venturi port seal removed, according to certain embodiments.

FIG. 6B shows the same backside elevation view of surgical cassette 200 seen in FIG. 5B with the first and second pump assemblies 202*a-b*, the venturi port seal 306, and the pressure sensor seal 308 removed from the base 206 to show the surfaces and related fluid channels disposed there beneath. Disposed beneath the first pump assembly 202*a* and the second pump assembly 202*b* are a first well 402*a* and a second well 402*b*, respectively. Both the first and second wells 402*a*, 402*b* comprise at least one semi-circular or substantially crescent-shaped grooves 404 that accommodate or seat the pump elastomers 310 therein. However, in certain embodiments, more than two wells 402 may be utilized in combination with a pump assembly 202. A small air hole 412 defined within each groove 404 permits air trapped beneath the pump elastomer 310 to escape when the pump elastomer 310 is being installed during the manufacturing process. In certain embodiments, each of the first and second wells 402*a*, 402*b* comprise a first pump channel 406*a* and second pump channel 406*b*, each pump channel 406*a*, 406*b* further comprising at least one pump channel inlet 408 defined at one end of the pump channel 406 and at least one pump channel outlet 410 defined at an opposing end of the pump channel 406. Also defined within each pump channel 406 and adjacent to each inlet 408 and outlet 410 is a pump channel trough 414 that, in certain embodiments, comprises a tapered width and depth along its arc length, the trough 414 terminating at a corresponding inlet 408 or outlet 410. Each trough 414 is defined to match the substantially semi-circular shape of the pump channel 406, with the trough 414 having a maximum width and depth adjacent to the corresponding inlet 408 or outlet 410 which then narrows in width and becomes shallower along its arc length until becoming flush with the surface of the pump channel 406. The defined shape of each trough 414 delivers better overall pumping performance and improves pressure pulsations when each pump assembly 202*a*, 202*b* is actuated. Each well 402*a*, 402*b* also comprises an angled surface 416 that is disposed more radially inward relative to the pump channels 406, the angled surface 416 providing a transition from the pump channels 406 to bottom surface 418.

In certain embodiments, disposed within the angled surface 416 is a plurality of retainer ring keyways 420 which are configured to accommodate a matching plurality of tabs disposed on the diaphragm retaining rings 314, thereby ensuring that each of the diaphragm retaining rings 314 are properly orientated within each well 402 during the manufacturing process. The bottom surface 418 of the first well 402*a*, which corresponds to the aspiration pump assembly 202*a*, comprises a sensor inlet 422*a* and a sensor outlet 424*a*. In certain embodiments, both sensor inlet 422*a* and sensor outlet 424*a* of the first pump assembly 202*a* comprises an elongated or extended shape. The bottom surface 418 of the second well 402*b*, which corresponds to the irrigation pump assembly 202*b*, also comprises a corresponding sensor inlet 422*b* and a sensor outlet 424*b*; however, according to certain embodiments, only the sensor inlet 422*b* comprises an elongated or extended shape while the sensor outlet 424*b* comprises a substantially circular shape. The sensor inlets 422*a*, 422*b* and the sensor outlet 424*a* of the first well 402*a* comprise an elongated shape so as to minimize the effects of air bubbles and assists in optimizing the path of the fluid as it is being pumped by each respective pump assembly 202*a*, 202*b*.

Also seen in FIG. 6B is a venturi port connection 432, which accommodates the venturi port seal 306 therein. A seal tab 430 ensures that the venturi port seal 306 is properly orientated to the base 206 during the manufacturing process. The venturi port connection 432 also comprises an air hole 428 defined therein so that air may escape as the venturi port seal 306 is being coupled to the venturi port connection 432 during the manufacturing process. A venturi port 426 is further defined within a center of the venturi port connection 432 which allows a venturi pump to be connected thereto which provides a negative or vacuum pressure to the venturi reservoir 282 detailed further below.

FIG. 6B further shows a pressure sensor ring 434 which accommodates the pressure sensor seal 308 therein. An air hole 438 defined in the pressure sensor ring 434 allows air to escape as the pressure sensor seal 308 is being coupled to the pressure sensor ring 434 during the manufacturing process. At the center of the pressure sensor ring 434 is a sensor surface 436 that comprises a pressure sensor inlet 440 and a pressure sensor outlet 442 defined therein. When the cassette 200 is coupled to the console 100, a pressure sensor disposed within the console 100 measures the fluid pressure beneath the pressure sensor seal 308 as fluid is flowing in from the pressure sensor inlet 440, across the sensor surface 436, and then exiting through the pressure sensor outlet 442.

The backside of the base 206 further comprises one or more locating features 444 defined therein that are configured to interact or engage with a corresponding plurality of pins disposed in the console 100 to help ensure that the cassette 200 is properly orientated as it is being coupled to the console 100. Additionally, in certain embodiments, a set of sliding features 446 are configured to interact or engage with a corresponding set of console rollers disposed on the console 100 which act to retain the cassette 200 to the console 100 once properly orientated.

Figure 6C:
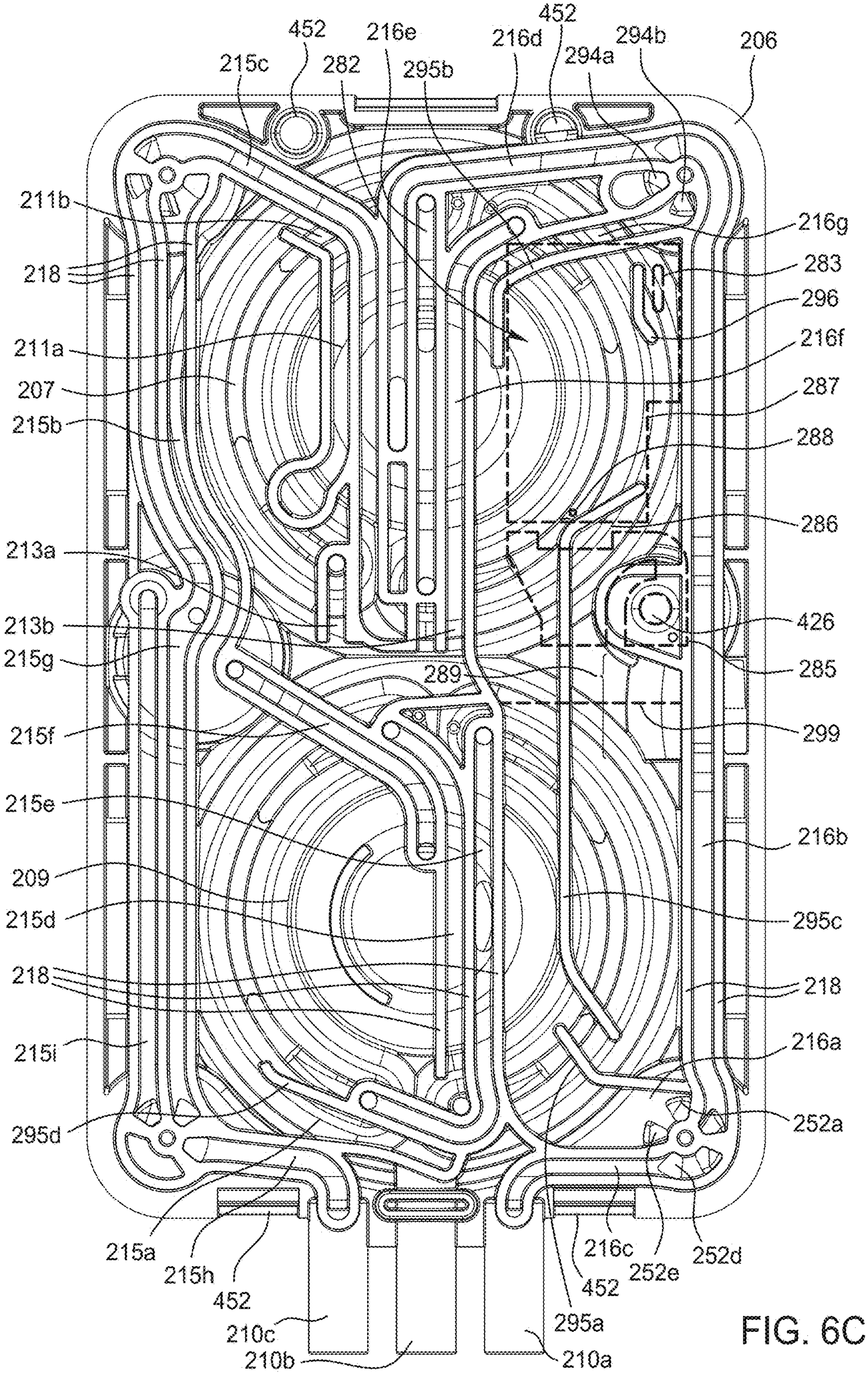
FIG. 6C is a front elevation view of the base of the surgical cassette of FIG. 6B, according to certain embodiments.

FIG. 6C shows a frontside elevation view of the base 206 seen in FIG. 6B, according to certain embodiments. Note that in FIG. 6C, some parts of cover 400 and manifold 600 are shown in phantom for illustrative purposes. As seen in FIG. 6C, a plurality of channels 215*a-i* and 216*a-g* are formed in housing 205.

In certain embodiments, the first plurality of channels 215*a-i* corresponds to an irrigation path within the cassette 200, while the second plurality of channels 216*a-g* correspond to an aspiration path within the cassette 200, both of which are further detailed below. In certain embodiments, a venturi reservoir 282 is formed in a righthand portion of the base 206, while a waste reservoir 207 and an irrigation reservoir 209 are formed in a lefthand portion of the base 206, the waste reservoir 207 being vertically disposed over the irrigation reservoir 209. The plurality of channels 215*a-i* and 216*a-g* are arranged to provide a plurality of independent fluid paths between pump assemblies 202, valve assemblies 204, venturi reservoir 282, waste reservoir 207, irrigation reservoir 209, and inlet/outlet ports 210.

Figure 7A:
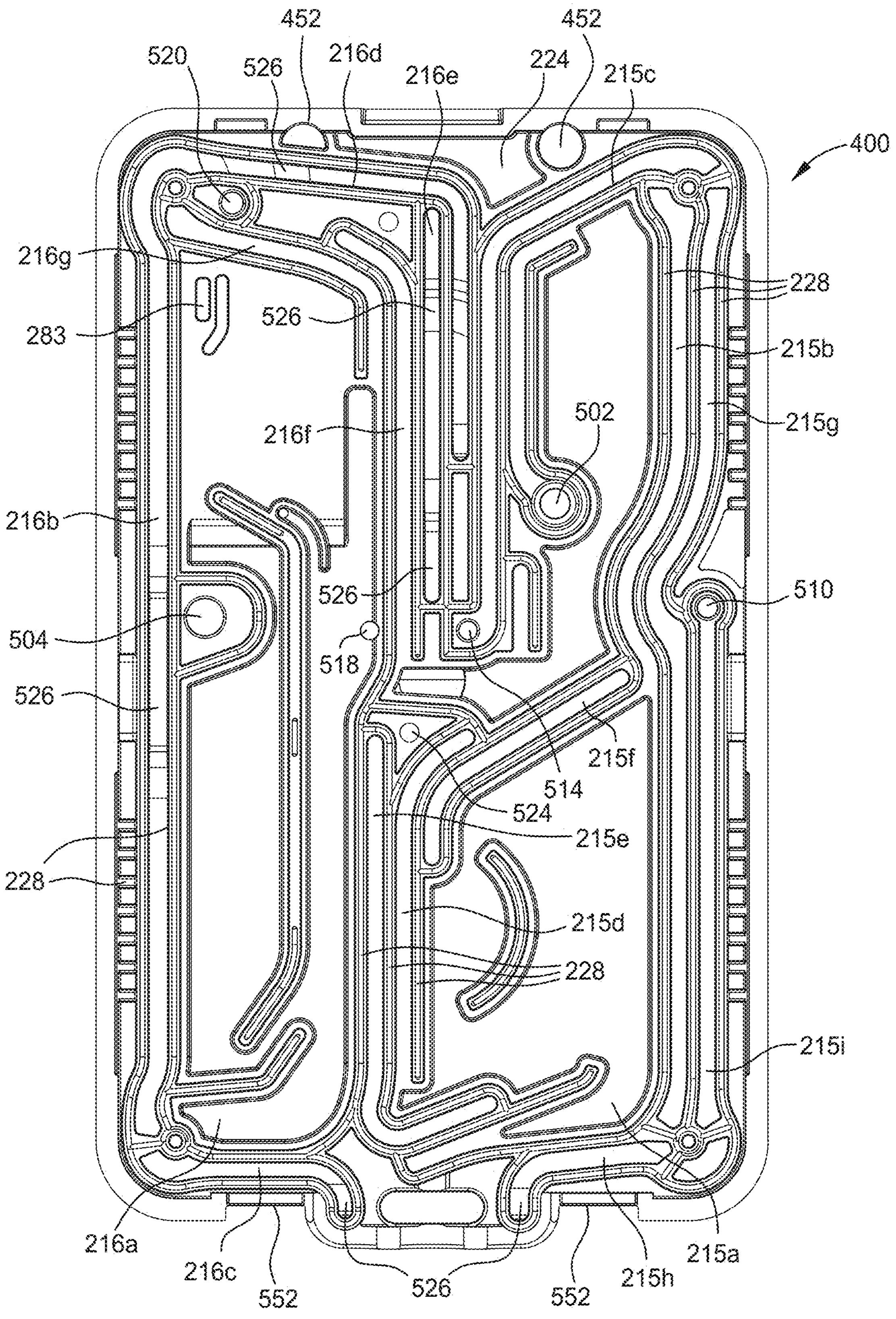
FIG. 7A is a back elevation view of the cover of the surgical cassette, according to certain embodiments.

Each channel 215*a-i* and 216*a-g* is longitudinally and equatorially defined in a first direction and second direction generally parallel to a plane of housing 205. Each channel 215, 216 includes sidewalls 218 oriented perpendicular to the plane of the housing 205 which, when combined with a corresponding plurality of faces 228 disposed on the cover 400 as seen in FIG. 7A, enclose the corresponding channel 216 therebetween. In addition, a depth of each channel 215*a-i* and 216*a-g* is defined in this perpendicular direction between a partition 220 (also referred to as a "lower wall") of base 206 (e.g., a frontside surface 222 thereof) and an inner surface 224 (shown in FIG. 7A) of cover 208.

The plurality of channels 215, 216 are sealingly enclosed through contact between the sidewalls 218 formed on frontside 214 of base 206 and a corresponding or mirror image set of faces 228 extending from inner surface 224 of cover 400. In order to effect sealing, the sidewalls 118 and corresponding faces 228 are molded in certain embodiments to each comprise a cross-section which is substantially half-circular in shape which, when assembled together (e.g., via ultrasonic welding), ensure precise alignment between opposing sides. In some other embodiments, the plurality of channels 215, 216 may be formed in cover 400 instead of base 206 and sealingly enclosed through contact between a backside surface of cover 400 and a corresponding frontside face of base 206. In some other embodiments, base 206 and cover 400 may be integrally formed as a single piece. In such embodiments, base 206 and cover 400 may be injection molded with the use of a slide technique.

FIG. 6C shows the venturi reservoir 282 being disposed inside housing 205 of surgical cassette 200 between base 206 and cover 400 according to certain embodiments. Venturi reservoir 282 serves at least three primary functions that are integral to the operation of surgical cassette 200. In general, venturi reservoir 282 provides a connection to a vacuum source for suction of fluids during a venturi operation, provides a fluid volume sink for normal vacuum venting within the surgical cassette, and provides a fluid volume sink for venting vacuum pressure that may build-up within surgical cassette 200 in the event of a post-occlusion break surge. In certain embodiments, the venturi reservoir 282 also allows air to separate from liquid and then evacuate out the cassette 200 through the surgical console during normal aspiration/suction use with venturi vacuum.

Surgical cassette 200 may be coupled to an external vacuum source (e.g., a venturi source or pump) disposed in console 100. Vacuum pressure from the external vacuum source is applied to venturi reservoir 282 through a vacuum port 283 in cover 400 seen in FIGS. 7A and 7B. In the illustrated embodiments, vacuum port 283 is an elongated slot. In certain embodiments, vacuum pressure within venturi reservoir 282 is about 720 mmHg (millimeters of Mercury). In certain embodiments, maximum air flow through vacuum port 283 is about 1.2 standard liters per minute. The external vacuum source is configured to apply vacuum pressure to venturi reservoir 282 through a vacuum flow path that passes from upstream to downstream through vacuum port 283 in cover 400 and into manifold 600 seen in FIGS. 8A and 8B where the air is filtered before passing back through respective openings in cover 400 and base 206 and reaching the external vacuum source. The vacuum flow path is described in more detail below with respect to FIGS. 9A and 9B.

Figure 7B:
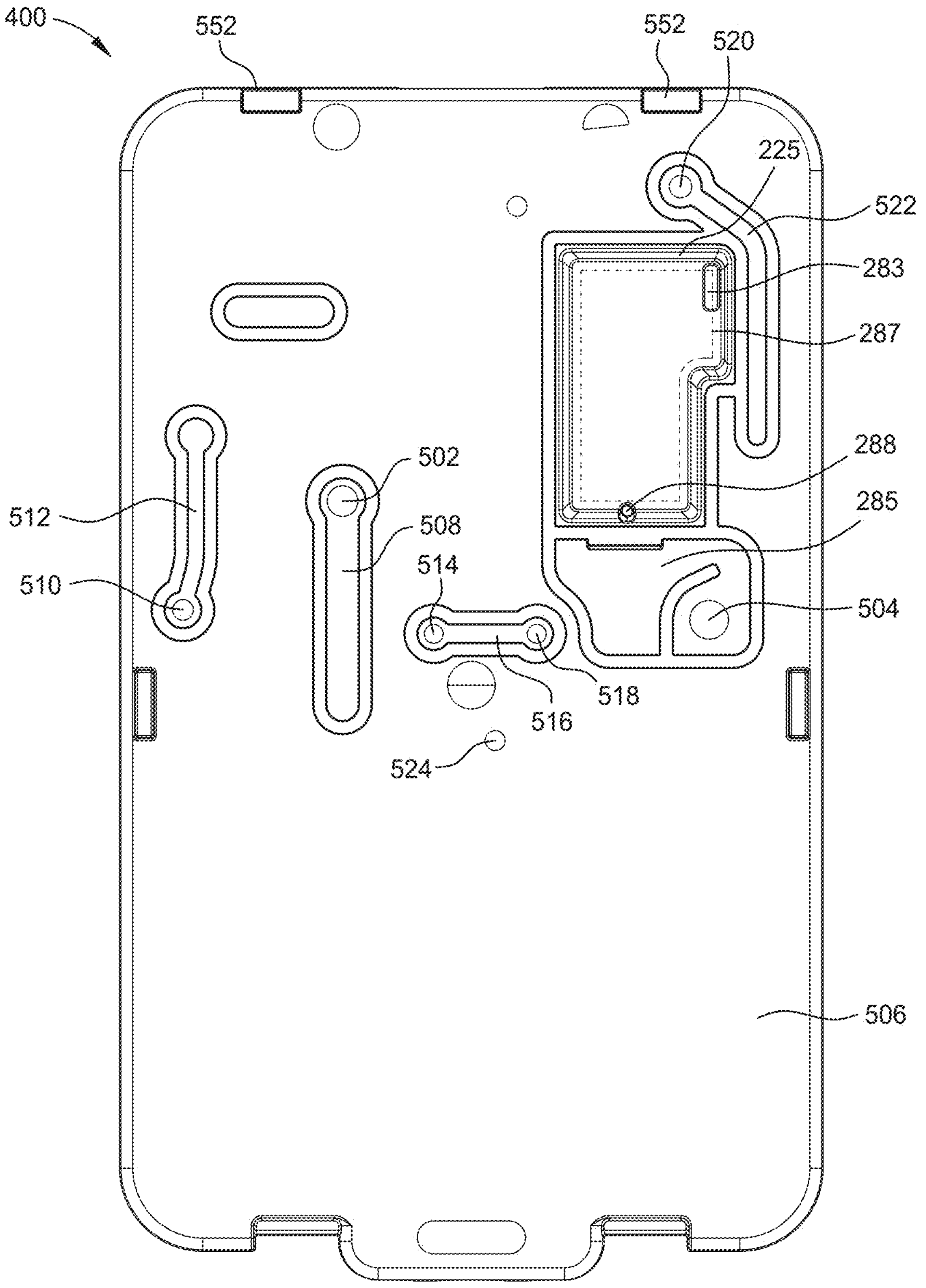
FIG. 7B is a front elevation view of the cover of the surgical cassette of FIG. 7A, according to certain embodiments.

In certain embodiments, the venturi port 426 in backside 212 of base 206 is coupled to a vacuum port on console 100 leading to the external vacuum source. A corresponding venturi pass through 504 in cover 400 is aligned with venturi port 426 in base 206. Venturi port 426 and venturi pass through 504 are oriented in a direction perpendicular to a plane of base 206. Venturi port 426 and venturi pass through 504 are in pressure communication between the external vacuum source and a fluid trap 285 that is defined between cover 400 and manifold 600. Fluid trap 285 is in fluid communication, through vacuum pathway 286, with a filter 287 that is disposed between cover 400 and manifold 600. In certain embodiments, the filter 287 which is seen in FIG. 7B as a broken line component is disposed within a correspondingly shaped filter pocket 225 defined within the cover 400, the filter pocket 225 comprising the venturi port 426 and a filter pocket drain 288 defined therein. Fluid trap 285 catches liquid that leaks through filter 287 and prevents the leaked liquid from entering the vacuum source.

Filter 287 is in pressure communication with the external vacuum source and vacuum port 283 in cover 400. The location of filter 287 overlays at least a portion of venturi reservoir 282 enabling the use of a more compact housing 205 compared to other designs. An upstream side of filter 287 faces towards cover 400. A downstream side of filter 287 faces towards manifold 600. Filter 287 seals with manifold 600 to prevent liquid from leaking around filter 287. Filter 287 permits air to pass from vacuum port 283 to fluid trap 285 in manifold 600 while blocking liquid from passing to the downstream side of filter 287 and into the external vacuum source. In certain embodiments, filter 287 is directly coupled to manifold 600 (e.g., ultrasonically welded), while in other embodiments the filter 287 may be directly coupled to the cover 400. In certain embodiments, filter 287 is hydrophobic, and thus impermeable to aqueous fluids.

In certain cases, liquid is able to pass through vacuum port 283 and becomes trapped between cover 400 and the upstream side of filter 287. The filter drain hole 288 is disposed through cover 400 in a position overlaying a lower end of filter 287. Filter drain hole 288 is in fluid communication between the upstream side of filter 287 and venturi reservoir 282 to drain the trapped liquid back into venturi reservoir 282. Draining of the trapped liquid through filter drain hole 288 helps maintain maximum usable filter area for maximum air flow through vacuum port 283. In certain embodiments, filter drain hole 288 is much smaller than vacuum port 283 in terms of cross-sectional area to prevent or reduce fluid contained in venturi reservoir 282 from easily passing through filter drain hole 288 and in the direction of filter 287. In certain embodiments, the cross-sectional area of filter drain hole 288 is about 10% or less of the cross-sectional area of vacuum port 283.

Returning to FIG. 6C, venturi reservoir 282 includes a level sensor area 289 defined in base 206. Vacuum port 283 is disposed above level sensor area 289. Level sensor area 289 is disposed along an optical path of a light sensor in console 100 that is used to determine a fluid level in venturi reservoir 282. In certain embodiments, the light sensor is an infrared sensor, a single camera sensor, or a complementary metal oxide semiconductor (CMOS) sensor. During normal operation, a nominal fluid level (indicated by dashed line 299) in venturi reservoir 282 is between lower and upper limits of level sensor area 289. The opening corresponds to level sensor area 289. The relatively small size or footprint of level sensor area 289 enables the use of a more compact housing 205 compared to other designs.

In certain embodiments, level sensor area 289 may further comprise a barcode specific to the surgical cassette 200, that when detected by the light sensor in console 100, facilitates identification of the surgical cassette 200. Identification of the surgical cassette 200 may also simultaneously facilitate the retrieving of different types of data relating to the surgical cassette 200 and/or the surgical console 100, such as, e.g., calibration data for pressure sensing.

The presence of air bubbles in or near level sensor area 289 may interfere with accurate detection of the fluid level in venturi reservoir 282 because the air bubbles can obscure the air-liquid interface. Therefore, in certain embodiments, a plurality of air baffles 295 (295*a-d*) as seen in FIG. 6C are disposed within venturi reservoir 282 and the irrigation reservoir 209 in order to divert air bubbles away from level sensor area 289 and irrigation path, respectively. The plurality of air baffles 295 are integral with base 206 and contact cover 400 when cover 400 is coupled to base 206. In some other embodiments, the plurality of air baffles 295 are integral with cover 400 instead of base 206.

A lower air baffle 295*a* is disposed above port 252*e* and extends up and to the left of the viewer in FIG. 6C. An upper air baffle 295*b* is disposed below port 294*b* and extends down and to the left of the viewer in FIG. 6C. Air baffles 295*a-b* form corresponding channel-like structures within venturi reservoir 282 that begin at corresponding ports 252*e*, 294*b* and end on the left side of venturi reservoir 282. For example, first channel 216*a* corresponds to a portion of venturi reservoir 282 below lower air baffle 295*a*. A central air baffle 295*c* is located to the right of the respective ends of air baffles 295*a-b* and extends from below to above level sensor area 289. The position of central air baffle 295*c* prevents air bubbles from crossing level sensor area 289 even after the air bubbles pass above lower air baffle 295*a* and below upper air baffle 295*b*, respectively. An opening between lower air baffle 295*a* and central air baffle 295*c* provides a path for equalization of fluid on the left and right sides of central air baffle 295*c*, so that the fluid level in level sensor area 289 corresponds to the actual fluid level in venturi reservoir 282. An opening between upper air baffle 295*b* and central air baffle 295*c* provides a path for the flow of air bubbles from the left side of central air baffle 295*c* to vacuum port 283 without crossing level sensor area 289.

A liquid baffle 296 is disposed within venturi reservoir 282 above level sensor area 289. Liquid baffle 296 is configured to reduce or prevent liquid from entering vacuum port 283 in cover 400, such as during bubbling, frothing, or overflowing of the liquid contained in venturi reservoir 282. Like air baffles 295, liquid baffle 296 is integral with base 206 and contacts cover 400 when cover 400 is coupled to base 206. An upper portion of central air baffle 295*c* extends directly below liquid baffle 296 so that liquid falling down from liquid air baffle 296 is blocked from entering the right side of central air baffle 295*c* and subsequently prevented from crossing level sensor area 289.

In certain embodiments, the waste reservoir 207 comprises a drain channel 211*a* formed therein, which terminates at one end at a drain port 502 defined in the cover 400 as detailed further below. In certain embodiments, an opposing end of the drain channel 211*a* comprises an angled or bent portion 211*b* that serves to form a lip or rim to the drain channel 211*a*. As fluid collects within the waste reservoir 207, the fluid can only move into the drain channel 211*a* after cresting the angled portion 211*b*. When fluid flow has stopped, the fluid within the waste reservoir 207 will remain below the angled portion 211*b* and will not enter the drain channel 211*a*. In this manner, the angled portion 211*b* ensures that when fluid flow through the cassette 200 is reversed, a defined volume of fluid will always be available within the waste reservoir 207, thereby preventing air from being pumped to other portions of the cassette 200. In certain embodiments, the waste reservoir 207 further comprises reflux structures 213*a*, 213*b* that are formed by a parallel pair of vertically orientated sidewalls 218. When a reverse or reflux flow through the cassette 200 is required, the reflux structures 213*a*, 213*b* serve to draw fluid from a deeper position within the waste reservoir 207 beneath the respective pump channel outlets 410.

Turning now to FIGS. 7A and 7B, greater detail of the cover 400 may be had. FIG. 7A shows a backside of cover 400 comprising an inner surface 224 with faces 228 that correspond to sidewalls 218 to form channels 215, 216 disposed thereon. FIG. 7B shows a frontside of cover 400 comprising an outer surface 506. The cover 400 further comprises a venturi pass through 504 that is aligned and in fluid communication with the venturi port 426 when the cover 400 has been coupled to the base 206. A drain port 502 is further defined through the cover 400, the drain port 502 being disposed at one end of a drain bag channel 508. An infusion port 510 is defined through the cover 400 and is disposed within an infusion channel 512 on the outer surface 506. In certain embodiments, the cover 400 further comprises a bypass inlet 514 and a bypass outlet 518 with a bypass channel 516 disposed there between as seen FIG. 7B. The bypass inlet 514 is in fluid communication with a third irrigation channel 215*c* of the base 206 while the bypass outlet 518 is in fluid communication with the venturi reservoir 282 within the base 206, as detailed further below so that fluid within the irrigation path may be bypassed or sent directly to the venturi reservoir 282 as needed. The cover 400 further comprises a suction port 520, which is disposed within a suction channel 522 disposed on the outer surface 506 of the cover 400. The suction port 520 is in fluid communication with a seventh aspiration channel 216*g* within the cassette 200 as detailed further below so that fluid suctioned from a posterior portion of the patient's eye may be sent directly to the venturi reservoir 282. The fluid trap 285, drain bag channel 508, infusion channel 512, bypass channel 516, and suction channel 522 are each sealingly enclosed through contact between the outer surface 506 of the cover 400 and a corresponding or mirror image inner surface 604 set of the posterior manifold 600*b* described in further detail below.

In certain embodiments, the cover 400 comprises a plurality of flow path optimization features 526 formed therein which, when the cover 400 is joined with the base 206 to form respective channels 215, 216, cooperate with the sidewalls 218 to provide a smooth flow path therein. In certain embodiments, the flow path optimization features 526 may comprise angled or sloping surfaces to compensate for a corresponding angle, slope, or other non-uniform surface within the portions of the channels 215, 216 disposed on the base 206.

Figure 11B:
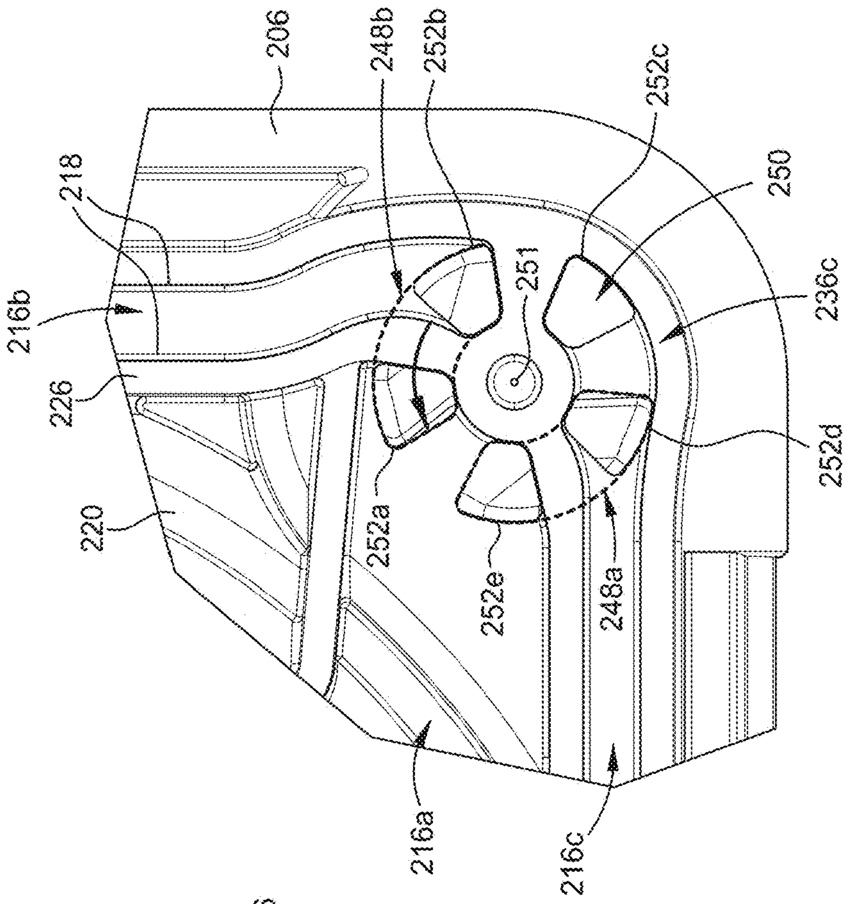
FIGS. 11A-11B are frontside elevation views of a portion of the surgical cassette of FIG. 2A illustrating two different valve positions, according to certain embodiments.
Figure 11A:
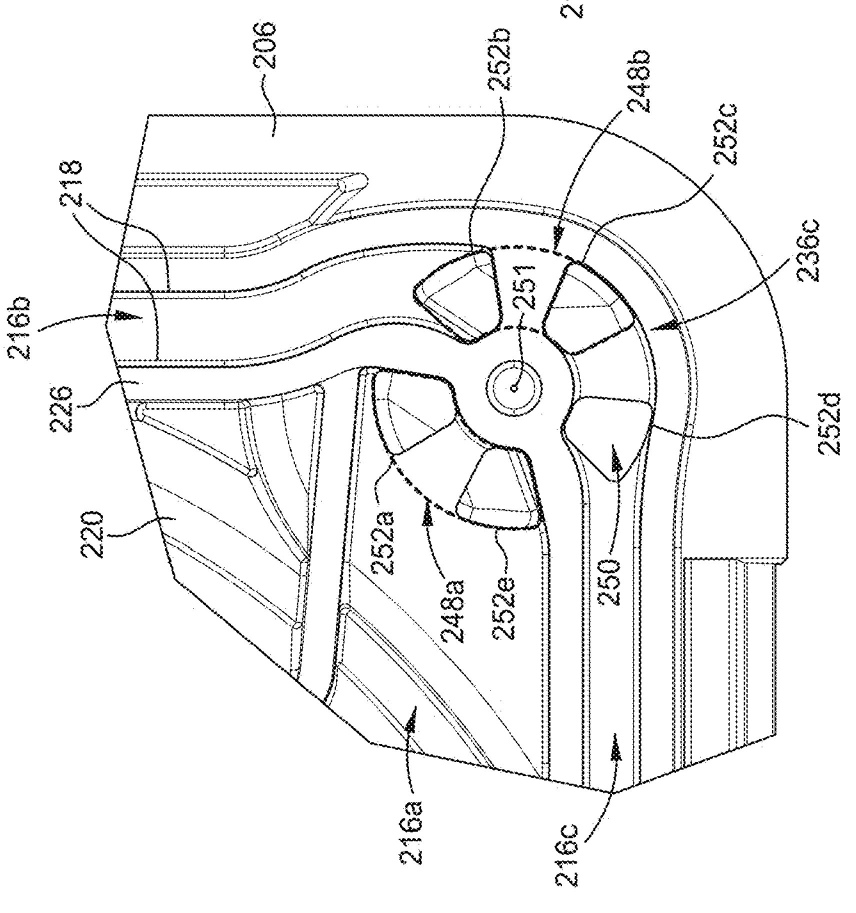

In certain embodiments, the cover 400 also comprises a sterilization port 524 defined therein which permits a sterilization gas such as ethylene oxide or its equivalent to pass there through during the manufacturing process so as to properly sterilize the internal components of the cassette 200. While FIGS. 7A and 7B show a single sterilization port 524 defined in a central portion of the cover 400, in certain embodiments, additional or different sterilization ports defined in other locations around the cover 400 other than what is explicitly shown may be utilized. In certain other embodiments, the base 206 may also comprise one or more sterilization ports in addition to or instead of the cover 400. For example, a base sterilization hole 251 may be defined through each valve assembly 204 as seen in FIGS. 11A and 11B.

Figure 8A:
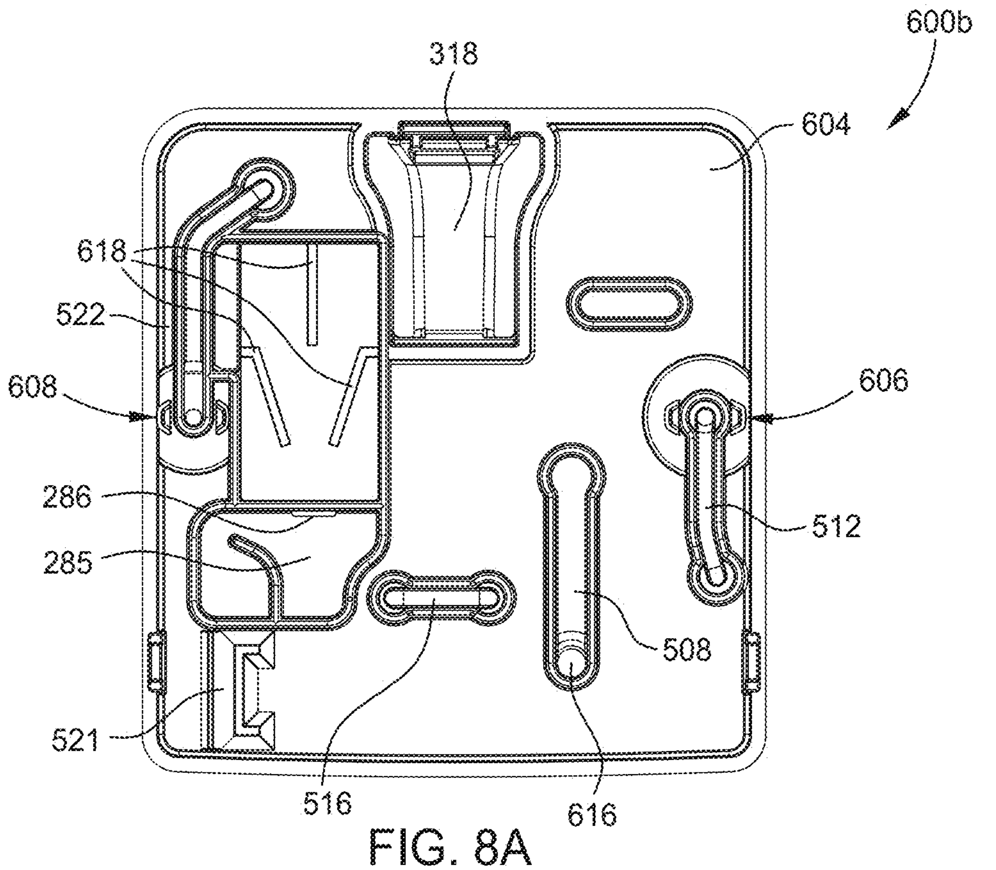
FIG. 8A is a back elevation view of the manifold of the surgical cassette, according to certain embodiments.
Figure 8B:
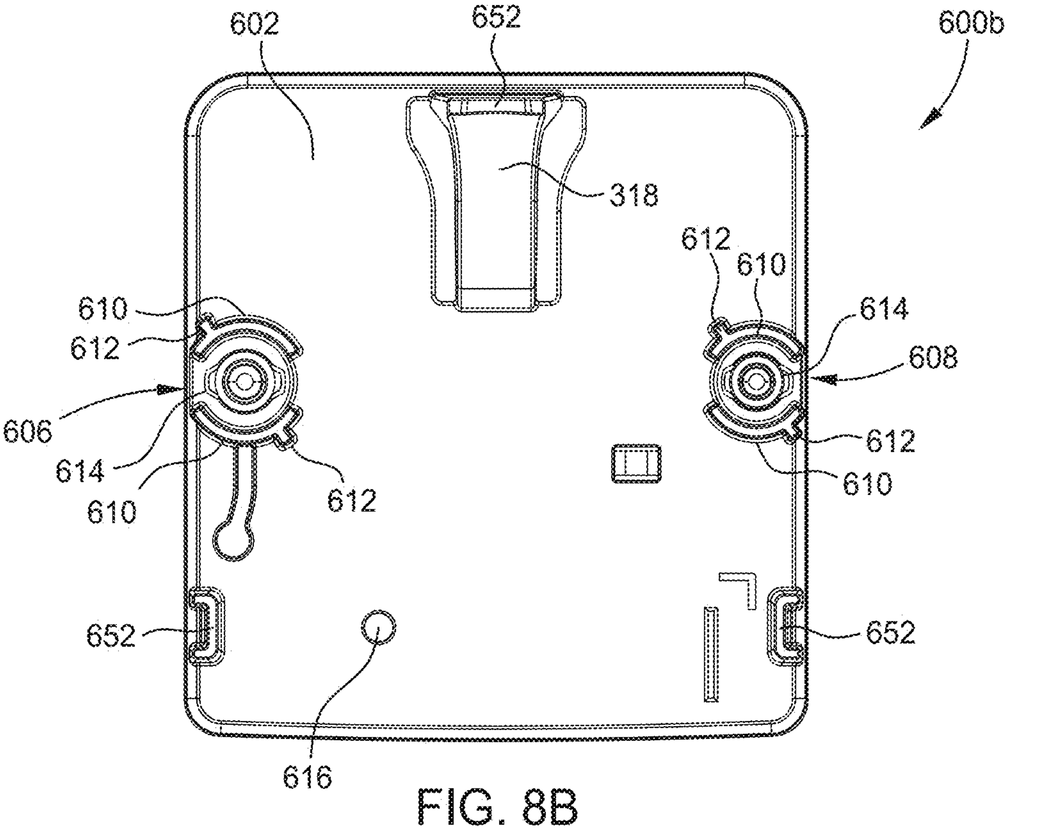
FIG. 8B is a front elevation view of the manifold of the surgical cassette of FIG. 8A, according to certain embodiments.

Turning FIGS. 8A and 8B, greater detail of the posterior manifold 600*b* may be had. FIG. 8A shows a backside of cover 400 comprising an inner surface 604 with features that correspond to the features disposed on the outer surface 506 of the cover 400 to form channels 508, 512, 516, 522 disposed thereon. FIG. 8B shows a frontside of the posterior manifold 600*b* comprising an outer surface 602. Defined through the posterior manifold 600*b* is an infusion connector 606 and a suction connector 608. In certain embodiments, both the infusion connector 606 and the suction connector 608 comprise a pair of sterile guards 610 disposed on the outer surface 602, which each comprise at least one angle indicator 612 that assist outside connections or tubing to couple to each of the connectors 606, 608 with the proper orientation. Each connector 606, 608, in certain embodiments, also comprise at least one locking element 614 which is configured to lock or maintain the outside connection or tubing in fluid contact with the cassette 200 after being coupled to each respective connector 606, 608. The outer surface 602 of the anterior manifold 600*a*, in contrast, comprises a more smooth or continuous surface as compared to the posterior manifold 600*b*.

As best seen in FIG. 8A, disposed on the inner surface 604 of the manifold 600*b*, it can be seen that in certain embodiments, a drain bag outlet 616 is defined through the manifold 600*b* and is in fluid communication with the drain port 502 of the cover 400 via the drain bag channel 508. The infusion connector 606 is in fluid communication with the infusion port 510 defined in the cover 400 via the infusion channel 512, while the suction connector 608 in turn is in fluid communication with the suction port 520 defined in the cover 400 via the suction channel 522. In certain embodiments, a plurality of filter support ribs 618 are disposed on the inner surface 604 so as to correspond and align with the filter pocket 225 disposed on the outer surface 506 of the cover 400. When in use, the filter support ribs 618 provide structural support to the filter 287 so that it does not sag, sink, or otherwise deform under changing pressures. Additionally, because each of the filter support ribs 618 contact the edges of the filter pocket 225 but not each other, any air bubbles caught therein have sufficient space to move down towards the vacuum pathway 286. Additionally in certain embodiments, the inner surface 604 comprises at least one light deflector 521 configured to prevent unwanted light from reaching the level sensor area 289. In one embodiment, the light deflector 521 may be comprised of a plurality of grooves with a substantially V-shaped cross-section; however, in certain other embodiments the light deflector 521 may comprise one or more prisms. In other embodiments, a sticker, tag, or another removable component may be selectively coupled to the manifold 600, the sticker or tag being comprised of material which either deflects or blocks incoming light, thereby further preventing light from reaching the level sensor area 289. In other embodiments, the manifold 600 may be at least partially comprised of light blocking ink or may have light blocking ink applied to its surfaces so as to deflect or block incoming light from the level sensor area 289.

In certain embodiments, the base 206, cover 400, and manifold 600 each comprise a corresponding plurality of stacking features. For example, the base 206 comprises a plurality of base stacking features 452 seen FIG. 6C, the cover 400 comprises a plurality of cover stacking features 452 seen in FIGS. 7A and 7B, and the manifold 600 comprises a plurality of manifold stacking features 652 seen in FIG. 8B. In certain embodiments as illustrated in the corresponding figures, the stacking features 452, 552, 652 are seen as being substantially circular, semi-circular, or rectangular in shape and may comprise a variety of different configurations including notches, clips, recesses, protrusions or the like. Each of the stacking features 452, 552, 652 are used during the manufacturing process allowing multiple bases 206, covers 400, and/or manifolds 600 to be efficiently stacked upon one another as they are removed from a mold, assembly line or other manufacturing step.

Returning to FIGS. 5A-6A, pump assemblies 202 and valve assemblies 204 are located on a backside 212 of base 206. Cover 400 is coupled to a frontside 214 (shown in FIG. 2) of base 206, which faces away from backside 212. In certain embodiments, the cover 400 may be welded, bonded, or fastened to base 206 using any suitable coupling mechanism. For example, cover 400 may be coupled to base 206 using a solid-state welding technique (e.g., ultrasonic welding in which high-frequency ultrasonic mechanical vibrations are locally applied to parts being held together under pressure to create a solid-state weld). In the illustrated embodiments, the cover 400 is coupled directly to frontside 214 of base 206 and the manifold 600 is coupled to cover 400. In some other embodiments, the cover 400 may consist of only a single piece, for example, the manifold 600 may be integrally formed or molded with the cover 400 so as to provide a single unitary component. Backside 212 of base 206 is configured to interface with console 100 when surgical cassette 200 is coupled thereto. For example, a drive interface on a valve body of each valve assembly 204 may engage a corresponding drive mechanism of console 100 for rotating the corresponding valve body. The valve body is described in more detail below with respect to FIGS. 10A-11B. In certain embodiments, the drive mechanism is a direct drive mechanism, wherein the drive interface engages with a motor (e.g., without gears) that operates at lower torque with faster valve response time when compared to a geared drive motor which is conventionally used. In such embodiments, the valve body may be rotated in a one-to-one ratio with the drive motor. However, the embodiments described herein may use any suitable type of drive motor.

Four bores 230 (230*a-d*) as best seen in FIG. 6A are formed in backside 212 of base 206 for receiving a corresponding valve assembly 204. Each bore 230 is defined by a cylindrical inner wall 232 (232*a-d*) and a backside surface 234 (234*a-d*) of partition 220 (seen in FIG. 10B). In certain other embodiments, there may be more or less than four bores to correspond to each valve assembly. One or more ports are formed through partition 220. The ports connect frontside surface 222 and opposite backside surface 234 of partition 220. Each port corresponds to one of the plurality of channels 215, 216 in contact with, or adjoining, frontside surface 222 of partition 220. The ports are described in more detail below with respect to FIGS. 11A and 11B.

Figure 10A:
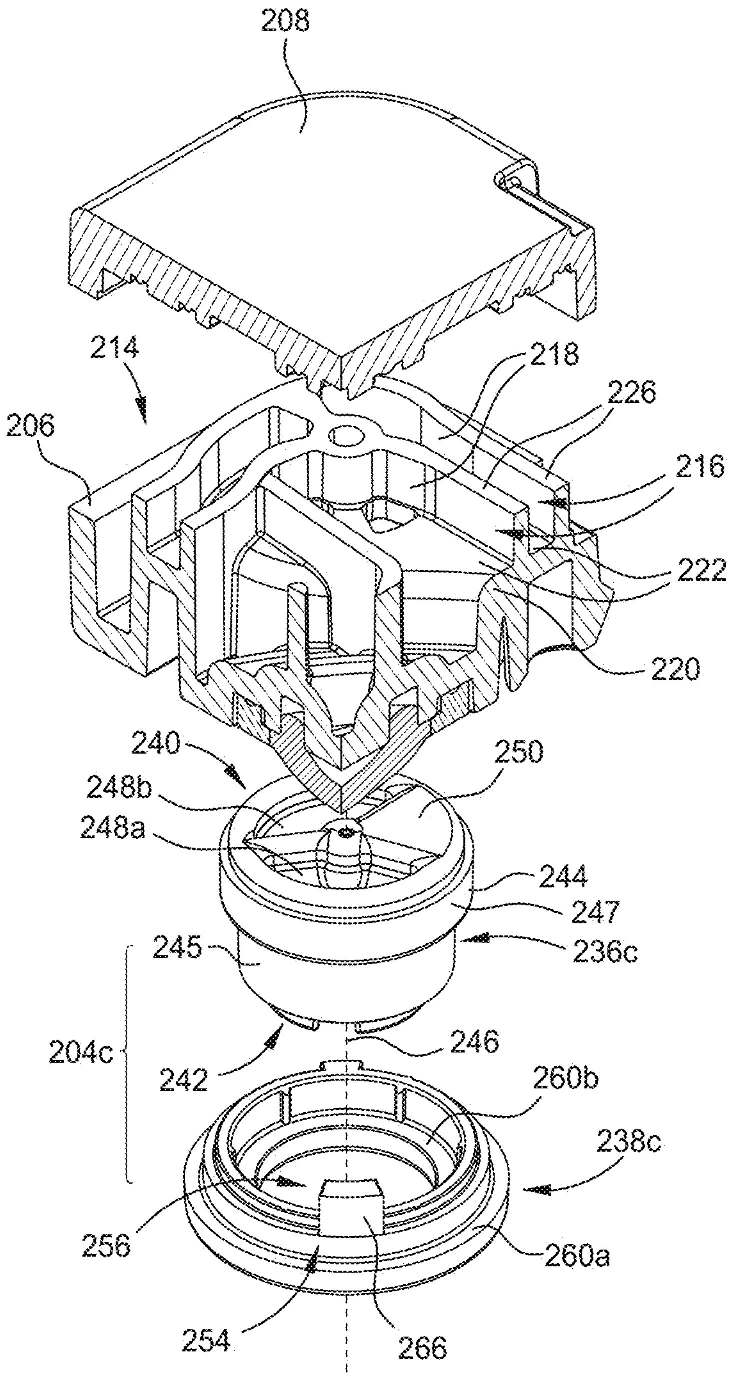
FIG. 10A is an enlarged exploded frontside isometric views of a portion of the surgical cassette of FIG. 2A illustrating an example valve assembly having two passages in the valve body, according to certain embodiments.
Figure 10B:
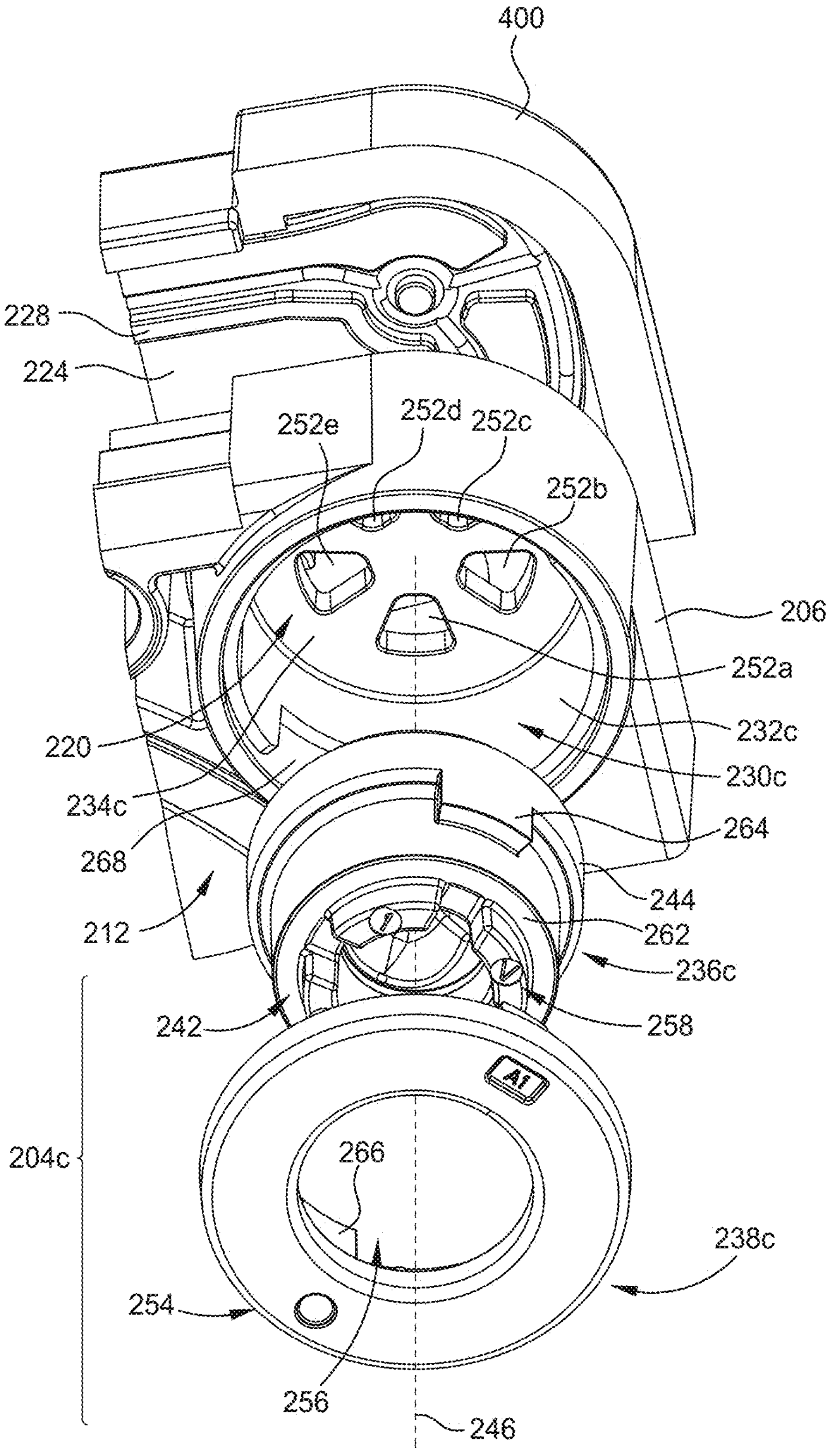
FIG. 10B is an enlarged exploded backside isometric view of a portion of the surgical cassette of FIG. 2A illustrating an example valve assembly having two passages in the valve body, according to certain embodiments.

Greater detail of the valve assemblies 204 and the operation thereof within the base 206 may be seen in FIGS. 10A and 10B, which show a top-down perspective exploded view and a bottom-up perspective exploded view of the third valve assembly 204*c*, respectively. Each valve assembly 204 generally includes a valve body 236 (236*a-d*) configured to be disposed in a corresponding bore 230 and a retaining ring 238 (238*a-d*) for retaining the valve body 236 in the bore 230. The valve body 236 and retaining ring 238 fit together in a stacked arrangement. The valve body 236 is disposed between backside surface 234 and the corresponding retaining ring 238. The retaining ring 238 applies a retention force on the corresponding valve body 236 to press the valve body 236 against backside surface 234, as described in more detail below. In some other embodiments, instead of being defined within base 206, each bore 230 may be defined within a corresponding retaining ring 238 that fits around a corresponding valve body 236. In some other embodiments, each valve body 236 may be rotatably coupled to base 206 using a retention cap. The retention cap may be disposed through valve body 236 (e.g., aligned with a longitudinal axis of valve body 236). In such embodiments, each valve body 236 may be coupled to base 206 without being disposed in a corresponding bore 230.

Valve body 236*c* of third valve assembly 204*c* as seen in FIGS. 10A and 10B has a first end 240, a second end 242, a cylindrical outer surface 244 connecting first end 240 and second end 242, and a longitudinal axis 246 orthogonal to first end 240. Cylindrical outer surface 244 includes multiple stepped portions having different outer dimensions. In some embodiments, the cylindrical outer surface 244 is comprised of a base portion 245 separated from a collar portion 247, the collar portion 247 having a larger diameter relative to the base portion 245 as best seen in FIG. 10A. In one embodiment, the base portion 245 has an approximate diameter of 13 mm (millimeters) and a longitudinal length of 5 mm, while the collar portion has an approximate diameter of 16 mm and a longitudinal length of 3 mm. Transitioning from the collar portion 247 to a sealing material 250 is a second shoulder 249.

Valve body 236*c* is rotatable about longitudinal axis 246. In certain embodiments, two recessed passages 248 (248*a-b*) are formed in valve body 236*c* at first end 240, while in other embodiments three passages may be formed in each valve body 236. In FIG. 10A, first passage 248*a* and second passage 248*b* are about equal in length when measured in a circumferential direction about longitudinal axis 246 (e.g., extending about longitudinal axis 246 in a circumferential direction by about 140° (degrees)-150°). In the illustrated embodiments, each passage 248 is sized to simultaneously open fluid communication with two ports of base 206 as described in more detail below with respect to FIGS. 11A-11B. In some other embodiments, each passage 248 may be sized to simultaneously open fluid communication with any suitable number of ports (e.g., two, three, or four ports). In the illustrated embodiments, passages 248 include arc-shaped annular segments extending circumferentially about longitudinal axis 246. In certain embodiments, a cross-section of passages 248 may be circular, round, oval, polygonal, square, any other suitable shape, or combinations thereof. Terminal ends of each passage 248 are defined through first end 240 of valve body 236*c*. In certain embodiments, a center axis of each passage 248 at the terminal ends is parallel to longitudinal axis 246. In certain embodiments, at least a portion of each passage 248, e.g., the portion between the terminal ends, is orthogonal to longitudinal axis 246. In certain embodiments, during fabrication, passages 248 are machined or molded in a direction parallel to longitudinal axis 246, e.g., starting from first end 240. In other words, an entire surface of each passage 248 is visible from first end 240 when viewed in a direction parallel to longitudinal axis 246. In the illustrated embodiments, passages 248 include an equal or symmetrical flow area. In some other embodiments, passages 248 may have different or asymmetric flow areas. In certain other embodiments, there may be only one passage or more than two passages formed in the valve body.

Valve body 236*c* includes a sealing material 250 at first end 240, which rotatably contacts backside surface 234*c* of base 206 for sealing first end 240 with backside surface 234*c*. Sealing between first end 240 and backside surface 234*c* forms a sealing interface between planar (e.g., non-cylindrical) surfaces. Because the sealing interface is on a longitudinal end (i.e., first end 240) of valve body 236*c*, this sealing arrangement may be referred to as "end-sealing" or "face-sealing." Face-sealing of valve body 236*c* facilitates flexibility in positioning and number of ports 252 in valve body 236*c*, and further facilitates the positioning of valve assemblies 204 at the corners of surgical cassette 200. In certain embodiments, sealing material 250 is formed from a rubber or elastomeric material (e.g., silicone rubber) which is bonded (e.g., overmolded) to valve body 236*c* at first end 240. In some other embodiments, valve body 236*c* and sealing material 250 may be integrally formed from the same material (e.g., high-density polyethylene).

Retaining ring 238*c* has an annular body 254 with a center opening 256. Retaining ring 238*c* fits over and around valve body 236*c* such that a drive interface 258 (shown in FIG. 10B) of valve body 236*c* is received within center opening 256. In some embodiments, drive interface 258 engages a drive mechanism of console 100 for rotating valve body 236 about longitudinal axis 246. Annular body 254 includes multiple stepped portions having different outer dimensions. At least one portion of annular body 254 is disposed radially between outer cylindrical surface 244 of valve body 236*c* and cylindrical inner wall 232*c* of bore 230*c*. At least another portion of annular body 254 is disposed outside bore 230*c*. An outer shoulder 260*a* formed between the stepped portions of annular body 254 contacts backside 212 of base 206 when retaining ring 238*c* is partially or fully seated in bore 230*c*. In certain embodiments, a lubricant (e.g., silicone oil) may be used to facilitate relative rotation between interfacing surfaces of valve body 236*c* (e.g., backside surface 262) and retaining ring 238*c* (e.g., inner shoulder 260*b*), and/or between sealing material 250 and backside surface 234*c*. In certain embodiments, one or more of the interfacing surfaces may be impregnated with lubricant. In some embodiments, the lubricant may be any liquid that provides a lubricious and/or hydrophobic coating.

The retention force applied by the retaining ring 238 is applied in a direction parallel to longitudinal axis 246 (axially) and forces first end 240 of valve body 236*c* towards backside surface 234*c* of base 206 which compresses sealing material 250 against backside surface 234*c* thereby forming a seal between passages 248 and corresponding ports 252. In certain embodiments, sealing material 250 is compressed in the direction parallel to longitudinal axis 246 (axially) up to 34% of its total height, thereby compressing or reducing the overall height down to approximately 1 mm, when retaining ring 238*c* is fully seated in bore 230*c*. In certain embodiments, retaining ring 238*c* is coupled to base 206 using a solid-state welding technique (e.g., ultrasonic welding) so that no gap or space is present between the inner shoulder 260*b* of the retaining ring 238 and the backside surface 262 of the valve body 236. In some other embodiments, retaining ring 238 may for example be snap-fit, threaded, and/or adhered to base 206. In certain embodiments, the valve body 236*c* itself may be snap-fit, threaded, and/or adhered directly to base 206 without use of the retaining ring 238.

In certain embodiments, valve body 236 includes a hard stop feature that can be used to correlate a rotational state of valve body 236 with one of the base 206 or retaining ring 238 in order to ensure proper alignment between passages 248 and corresponding ports 252 during operation.

In certain other embodiments, the hard stop feature may comprise one or more optical indicators disposed on the valve body 236 and the retaining ring 238, respectively, for detection by optical sensors on the surgical console 100. For example, instead of physical contact being made between the valve body 236 and the retaining ring 238, the one or more optical indicators may indicate when a first maximum rotational position between the valve body 236 and retaining ring 238 is achieved, thereby indicating to the surgical console 100, or other system, the current alignment or rotational position the valve body 236 is in relative to the retaining ring 238.

In certain embodiments, a plurality of ports 252 are formed through partition 220 from backside surface 234 to frontside surface 222. In operation, valve body 236*c* is rotatable relative to backside surface 234*c* of base 206 to align each passage 248 with a corresponding port 252 (252*a-c*) of base 206 to open pressure and/or fluid communication between corresponding ones of the plurality of channels 216. A flow axis through each port 252 is parallel to longitudinal axis 246 of valve body 236*c*. A shape of each port 252 may correspond to a cross-section of each passage 248 of valve body 236*c* to help maintain flow therethrough. In certain embodiments, a cross-sectional shape of each passage 248 may be formed by continuing a shape of the corresponding port 252 as a swept surface through valve body 236*c*.

In the illustrated embodiments, five ports 252 are formed through partition 220, from the backside surface 234 to frontside surface 222, within each bore 230. However, there may be any suitable number of ports (e.g., two to seven ports, such as three ports) in each bore 230. In the illustrated embodiments, ports 252 include arc-shaped annular segments. In some other embodiments, ports 252 may be circular, round, oval, polygonal, square, any other suitable shape, or combinations thereof. In the illustrated embodiments, ports 252 have an equal flow area. In some other embodiments, ports 252 may have different flow areas. In the illustrated embodiments, ports 252 are uniformly spaced in the circumferential direction. In some other embodiments, ports 252 may have different spacing in the circumferential direction.

FIGS. 11A-11B are frontside elevation views of a portion of surgical cassette 200 of FIG. 5A illustrating two different valve positions, according to certain embodiments. In FIGS. 11A-11B, cover 400 and manifold 600 is omitted for clarity. An exemplary first valve rotational state of valve assembly 204*c* is illustrated in FIG. 11A. In the first valve rotational state, first passage 248*a* (indicated with dashed outline) of valve body 236*c* is aligned with first port 252*a* and fifth port 252*e* of venturi reservoir 282. When first passage 248*a* is aligned with both ports of venturi reservoir 282, fluid communication with venturi reservoir 282 is closed, and therefore, the first port 252*a* and fifth port 252*e* may be referred to as "closed" in the first valve rotational state. First port 252*a* is adjacent to fifth port 252*e* and is disposed through partition 220 of base 206 below level sensor area 289 like fifth port 252*e* as described above. In the first valve rotational state, second passage 248*b* (indicated with dashed outline) is aligned with a second port 252*b* corresponding to a second channel 216*b* and a third port 252*c* corresponding to a third channel 216*c*, thereby opening fluid communication between second channel 216*b* and third channel 216*c*. In the first valve rotational state, a sector of sealing material 250 in a clockwise direction relative to second passage 248*b* is aligned with a fourth port 252*d*, thereby closing fluid communication through fourth port 252*d*.

In certain embodiments, in the first valve rotational state, a hard prime may be performed on second channel 216*b* upstream of first pump assembly 202*a* (also referred to as an "aspiration path" of surgical cassette 200). In general, the hard prime involves building-up vacuum very high in the aspiration path and then suddenly opening the aspiration path to liquid from venturi reservoir 282. The sudden rush of liquid causes a high flow rate through the aspiration path and shears any trapped air bubbles from their positions. The trapped air bubbles are allowed to enter the main flow stream and are passed to a drain bag coupled to surgical cassette 200. In certain embodiments, the hard prime is an automated sequence performed by computer 103 of console 100. The hard prime may be performed as part of the surgical setup of surgical cassette 200. The hard prime provides lower and more repeatable total aspiration path compliance (improved vacuum responsiveness) of surgical cassette 200 and results in lower fluid volume surges during post-occlusion break surge events.

In certain embodiments, second channel 216*b* is in fluid communication with first pump assembly 202*a* (also referred to as an "aspiration pump") and third channel 216*c* is in fluid communication with an aspiration line, e.g., of a surgical handpiece or other device for aspirating fluid from the eye (e.g., handpiece 112 shown in FIG. 1A). In such embodiments, the first rotational state corresponds to an aspiration state.

An example operation of valve assembly 204*c* is described below. In certain embodiments, occlusion or blockage of fluid flow through the handpiece (or other device) can occur during aspiration due to build-up of surgical material (e.g., lens fragments, debris, etc.) causing vacuum pressure to build-up between the handpiece and, e.g., first pump assembly 202*a*. With sufficient vacuum pressure build-up, breakage of the occlusion often occurs leading to a rapid surge of fluid being aspirated from the eye and into valve assembly 204*c* through third channel 216*c*, and in certain embodiments, including second channel 216*b* and first pump assembly 202*a*. This process is commonly referred to as post-occlusion break surge.

The occurrence of post-occlusion break surge may be mitigated using certain embodiments disclosed herein. In certain embodiments, post-occlusion break surge is indicated by a rapid pressure change that may be detected using a pressure sensor in the handpiece or the surgical cassette 200. When post-occlusion break surge is detected, valve assembly 204*c* may be switched from the first valve rotational state of FIG. 11A to a second valve rotational state illustrated in FIG. 11B by rotating valve body 236*c* counterclockwise about longitudinal axis 246 by about 72 degrees (as indicated by the arrow). In the second valve rotational state, first passage 248*a* (indicated with dashed outline) of valve body 236*c* is aligned with fourth port 252*d* and fifth port 252*e*, thereby opening fluid communication between venturi reservoir 282 and third channel 216*c*. In the second valve rotational state, second passage 248*b* (indicated with dashed outline) is aligned with first port 252*a* and second port 252*b*, thereby opening fluid communication between venturi reservoir 282 and second channel 216*b*. In the second valve rotational state, the sector of scaling material 250 in a clockwise direction relative to second passage 248*b* is aligned with third port 252*c*, thereby closing fluid communication through third port 252*c*.

In embodiments with second channel 216*b* in fluid communication with first pump assembly 202*a* and third channel 216*c* in fluid communication with a surgical handpiece (as described above), other device, or surgical site, the second rotational state corresponds to a dual path venting state. Thus, fluid communication is open between first channel 216*a* of venturi reservoir 282 and first pump assembly 202*a* through second channel 216*b*. In the dual path venting state, fluid communication is also open between first channel 216*a* of venturi reservoir 282 and the surgical handpiece, other device, or surgical site, through third channel 216*c*. Valve assembly 204*c* may be switched from the aspiration state shown in FIG. 11A to the dual path venting state shown in FIG. 11B by rotating valve body 236*c* counterclockwise about longitudinal axis 246 by about 72 degrees (as indicated by the arrow). Switching to the dual path venting state immediately when post-occlusion break surge is detected mitigates the resulting rapid aspiration of fluid from the eye by filling second channel 216*b* and third channel 216*c* with fluid before significant fluid flow from the eye occurs.

In the dual path venting state, first port 252*a* and fifth port 252*e* are opened simultaneously. Having first port 252*a* and fifth port 252*e* opened at the same time provides independent venting to venturi reservoir 282 of vacuum pressure built-up within corresponding channels 216*b-c* of base 206. For instance, vacuum pressure built-up in third channel 216*c* between fifth port 252*e* and the aspiration path is vented through fifth port 252*e*. Likewise, vacuum pressure built-up in second channel 216*b* between first port 252*a* and first pump assembly 202*a* is vented through first port 252*a* independently of the venting of the surgical site through channel 216*c* (e.g., the aspiration path). In certain embodiments, second channel 216*b* has a volume of about 4 cc (cubic centimeters), whereas the aspiration path (including third channel 216*c*) has a volume of only about 0.5 cc. Thus, the relatively high compliance of second channel 216*b* contributes a majority of the vacuum pressure volume that leads to the post-occlusion break surge. Therefore, the independent venting that is provided by switching fluid communication between second channel 216*b* leading to the pump and third channel 216*c* leading to the eye greatly reduces the post-occlusion break surge volume.

In certain embodiments, in response to detecting post-occlusion break surge, the surgical cassette 200 may be vented by pumping irrigation/infusion fluids through pump assembly 202*b* and downstream toward port 210*c*, while second valve assembly 204*b* and/or fourth valve assembly 204*d* are disposed in a rotational state corresponding to a venting state.

In certain embodiments, instead of the valve assembly 204*c* being rotated in the counterclockwise direction as shown in FIGS. 11A and 11B, the valve body 236*c* may instead be rotated clockwise about longitudinal axis 246, thereby venting second channel 216*b* and cutting off third channel 216*c*. In other words, rotating the valve body 236*c* clockwise would switch the fluid connection to the surgical site from the highly compliant path of the second channel 216*b* which is concurrently vented independently.

In certain embodiments, first port 252*a* and fifth port 252*e* of venturi reservoir 282 may be combined into one port. Similarly, third port 252*c* and fourth port 252*d* may be combined into one port. Thus, in some embodiments, there may be three ports utilized for dual path venting. In certain embodiments, a single path valve 402 may be used to vent channel 216*c* to venturi reservoir 216*a*. In other embodiments, channel 216*b* may be vented after channel 216*c* by continuing ration of the valve body 402.

Figure 9A:
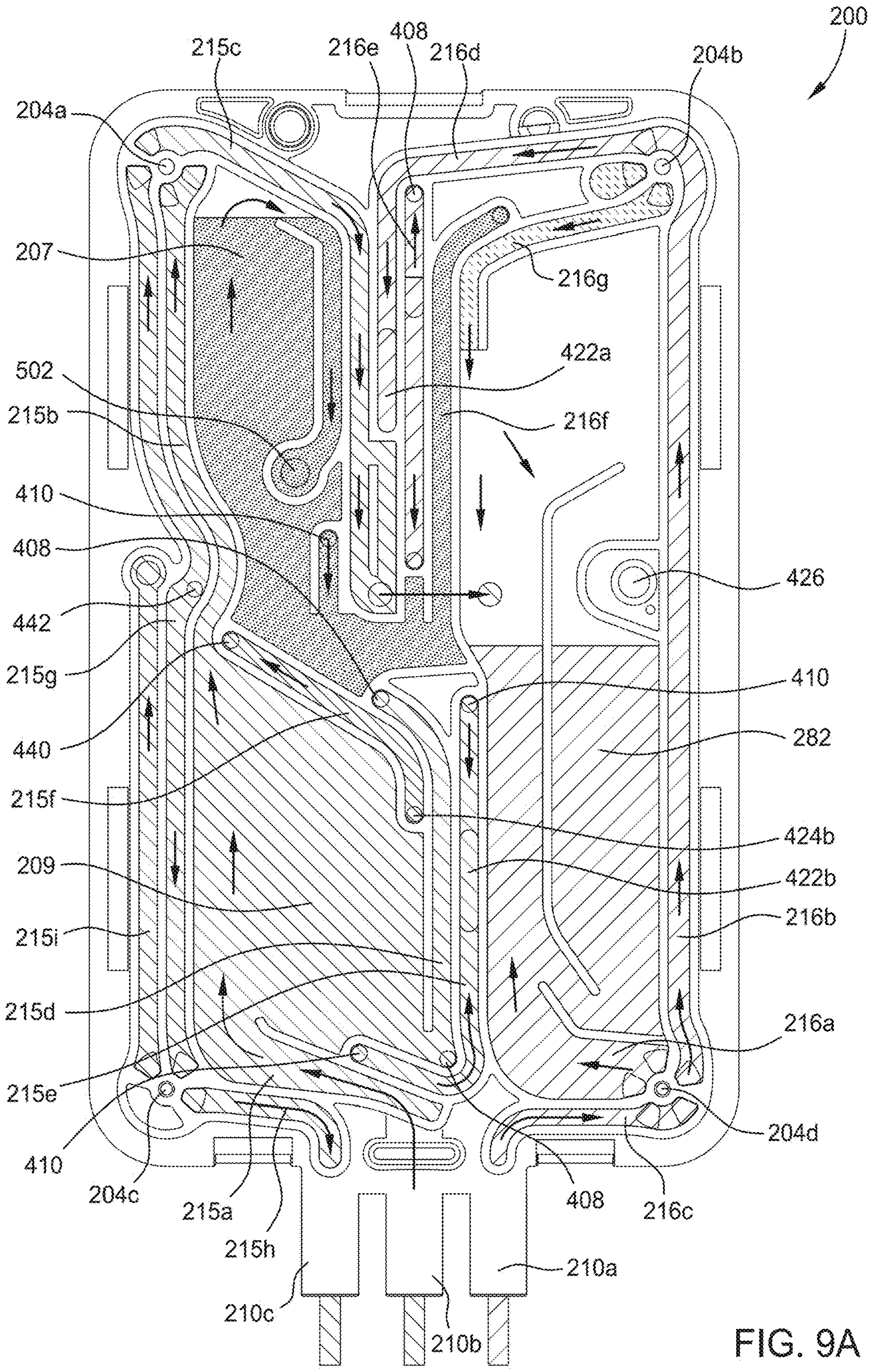
FIG. 9A is a front elevation view of the base of the surgical cassette of FIG. 6C illustrating the flow paths of fluid taken through the base, according to certain embodiments.
Figure 9B:
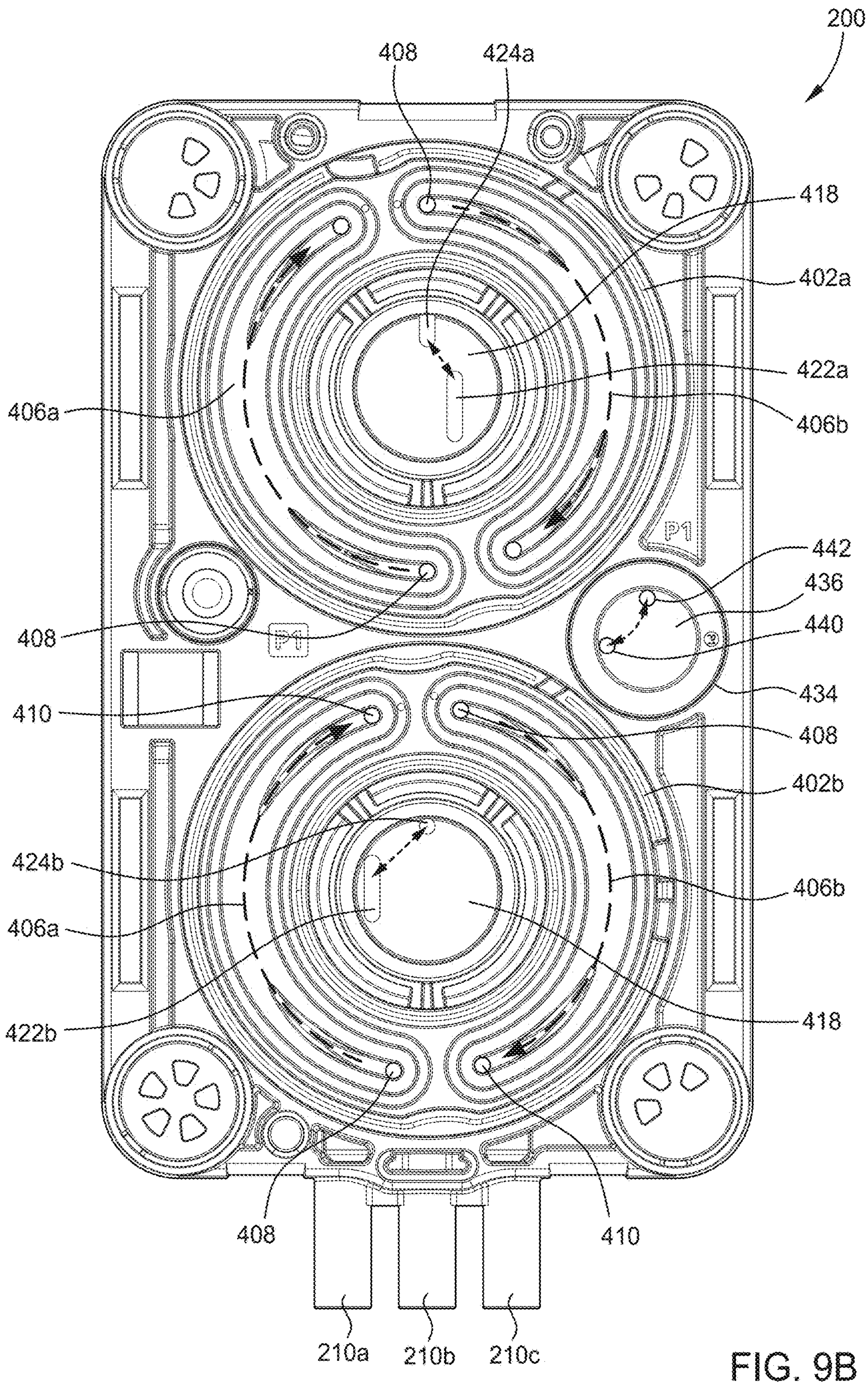
FIG. 9B is a back elevation view of the base of the surgical cassette of FIG. 6B illustrating the flow paths of fluid taken through the base, according to certain embodiments.

Greater detail of the aspiration, suction, irrigation, and infusion flow paths provided by the cassette 200 may be had by turning to FIGS. 9A and 9B.

In certain embodiments, an aspiration fluid path is provided by the cassette 200 where venturi reservoir 282 receives fluids originating from an anterior portion of the patient's eye that are aspirated through aspiration port 210*a* of base 206. For example, aspirated fluids may enter aspiration port 210*a*, flow through third aspiration channel 216*c* through the venting valve assembly 204*d*, and then enter into venturi reservoir 282 through port 252*e* and the first aspiration channel 216*a*. Thus, port 252*e* is in fluid communication with an aspiration line of surgical handpiece 112 (shown in FIG. 1A) through port 210*a* of base 206. Port 252*e* is disposed through base 206 below level sensor area 289. It should be noted that valve assemblies 204 are shown in FIG. 9A with their respective valve bodies 236 removed for clarity purposes.

In certain embodiments, when the irrigation valve assembly 204*d* is appropriately manipulated or actuated, the aspirated fluid may also or instead be directed along the second aspiration channel 216*b* as shown by the dashed line arrow to and then through the suction valve assembly 204*b* to the fourth aspiration channel 216*d*. Under vacuum pressure from the pump assembly 202*a*, the fluid is drawn into the sensor inlet 422*a* where it then enters the first well 402*a* on the frontside of the base 206 seen in FIG. 9B. As the fluid traverses across the bottom surface 418 of the first well 402*a*, a pressure reading may be detected by a pressure sensor disposed in the surgical console 100 via the diaphragm 312 (seen in FIG. 2) disposed there between.

Fluid then exits the first well 402*a* through the sensor outlet 424*a* and enters the fifth aspiration channel 216*e* on the frontside of the base 206 seen in FIG. 9A. From here, according to the current configuration of the valve assemblies 204 of certain embodiments, fluid is drawn vertically upward and through the pump channel inlet 408 of the second pump channel 406*b*, and/or vertically downward and through the pump channel inlet 408 of the first pump channel 406*a*. The pump assembly 202*a* drives the fluid through the first pump channel 406*a* and the second pump channel 406*b* in a clockwise direction indicated by the dashed arrows seen in FIG. 9B, where it then exits through the respective pump channel outlet 410 in each pump channel 406*a*, 406*b*.

Returning to FIG. 9A, fluid which exits the second pump channel 406*b* is deposited into the waste reservoir 207, while fluid which exits the first pump channel 406*a* is also ultimately sent to the waste reservoir 207 via the sixth aspiration channel 216*f*. Fluid will continue to be collected within the waste reservoir 207 until it reaches the edge of the angled portion 211*b* of the drain channel 211*a*, at which point the excess fluid will drop into the drain channel 211*a* and then exit the base 206 through the drain port 502 defined in the cover 400. The fluid will then travel through the drain bag channel 508 defined between the cover 400 (seen in FIG. 7B) and the manifold 600 and then exit the manifold 600 and the cassette 200 entirely through the drain bag outlet 616 (seen in FIGS. 8A and 8B) and into related tubing, drain bag, or the like. Meanwhile, fluid that does not enter the drain channel 211*a* within the drain reservoir 207 remains therein so as to be available for any desired reverse or reflux flows through the aspiration channels 216.

In certain embodiments, a suction fluid path is provided by the cassette 200 where venturi reservoir 282 receives fluids that are suctioned through suction connector 608 on the frontside of manifold 600*b*. For example, fluids originating from a posterior portion of the patient's eye may pass through the suction connector 608, flow through suction channel 522 defined between manifold 600*b* and cover 400, through suction port 520 in cover 400, and into port 294*a* of the suction valve assembly 204*b* in base 206. Fluid may then enter into venturi reservoir 282 through the eighth aspiration channel 216*g*. Port 294*b* is disposed through base 206 above level sensor area 289. In certain embodiments, fluids entering venturi reservoir 282 through port 252*e* or port 294*b* include a mixture of liquid, such as BSS (Balanced Salt Solution), and air. In some other embodiments, the fluid is only liquid or only air. In certain embodiments, a flow rate of the fluid is about 200 cc/min (cubic centimeters per minute) or less. Fluid collected within the venturi reservoir 282 may pass through the aspiration path described above upon the appropriate actuation of the venting valve assembly 204*d* and the suction valve assembly 204*b*. It is in this fashion that the cassette 200 may provide means to remove fluid from both the anterior and posterior portions of the patient's eye, provided that a posterior manifold 600*b* has been coupled to the cover 400. In contrast, if an anterior manifold 600*a* is coupled to the cover 400 according to certain other embodiments, then only the aspiration from the anterior portion of the patient's eye may be performed.

In certain embodiments, fluid that is be sent to the patient's eye may be stored or maintained within the cassette 200 via the admin port 210*b*. For example, driven by pressure from the pump assembly 202*b*, fluid is drawn through the admin port 210*b* and into the irrigation reservoir 209 via the first irrigation channel 215*a* as indicated by the dashed arrows.

In certain embodiments, an irrigation and/or an infusion fluid path is provided by the cassette 200 where fluid within the irrigation reservoir 209 is ultimately directed to an anterior portion of the patient's eye. For example, as seen in FIG. 9A, upon actuation of the pump assembly 202*b*, at least a portion of the fluid within the irrigation reservoir flows into the fourth irrigation channel 215*d*, where it is directed both vertically upward to the pump channel inlet 408 of the second pump channel 406*b* of the second well 402*b*, and vertically downward to the pump channel inlet 408 of the first pump channel 406*a* of the second well 402*b*.

Returning to FIG. 9B, the pump assembly 202*b* drives the fluid through the first pump channel 406*a* and the second pump channel 406*b* of the second well 402*b* in a clockwise direction indicated by the dashed arrows seen in FIG. 9B where it then exits through the respective pump channel outlets 410 in each pump channel 406*a*, 406*b*.

In certain embodiments, as fluid exits from the first pump channel 406*a*, it enters into one end of the fifth irrigation channel 215*e*, while fluid which exits from the second pump channel 406*b* enters an opposing end of the fifth irrigation channel 215*e* as seen in FIG. 9A. The fluid from both ends of the fifth irrigation channel 215*e* is drawn into the sensor inlet 422*b* where it then enters the second well 402*b* on the frontside of the base 206 seen in FIG. 9B. As the fluid traverses across the bottom surface 418 of the second well 402*b*, a pressure reading may be detected by a pressure sensor disposed in the surgical console 100 via the diaphragm 312 (seen in FIG. 2) disposed there between.

Fluid then exits the second well 402*b* through the sensor outlet 424*b* and enters the sixth irrigation channel 215*f* on the frontside of the base 206 seen in FIG. 9A. From here, fluid is then drawn into the pressure sensor ring 434 via the pressure sensor inlet 440 and then across the sensor surface 436 as seen in FIG. 9B. As the fluid traverses across the sensor surface 436 of the pressure sensor ring 434, a pressure reading may be detected by a redundant pressure sensor disposed in the surgical console 100 via the pressure sensor seal 308 (seen in FIG. 2) disposed there between. After the pressure of the fluid has been measured by the redundant pressure sensor, fluid exits the pressure sensor ring 434 through the pressure sensor outlet 442.

Returning to FIG. 9A, fluid from the pressure sensor outlet 442 moves into the seventh irrigation channel 215*g* where, according to the current configuration of the valve assemblies 204 of certain embodiments, fluid is drawn vertically upward and through the seventh irrigation channel 215*g* to the bypass valve assembly 204*a*, and/or vertically downward and through the seventh irrigation channel 215*g* to the irrigation valve assembly 204*c*.

In certain embodiments, fluid directed through the irrigation valve assembly 204*c* via the seventh irrigation channel 215*g* may be directed out of the cassette 200 through the eighth irrigation channel 215*h* and then the irrigation port 210*c* where it may then be directed to an anterior portion of the patient's eye using the surgical console 100, the handpiece 112, and related tubing. However, in other embodiments, fluid directed through the irrigation valve assembly 204*c* may instead or additionally be transferred to the ninth irrigation channel 215*i* and then subsequently out of the infusion port 510 defined in the cover 400. In this instance, fluid then passes through the infusion channel 512 defined between the cover 400 and the manifold 600 and then subsequently out of the manifold 600 through the infusion connector 606 into related tubing where it then may be delivered to a posterior portion of the patient's eye. It is in this fashion that the cassette 200 may provide irrigation and infusion to the anterior and posterior portions of the patient's eye, respectively, provided that a posterior manifold 600*b* has been coupled to the cover 400. In contrast, if an anterior manifold 600*a* is coupled to the cover 400 according to certain other embodiments, then only irrigation to the anterior portion of the patient's eye may be performed.

In certain embodiments, fluid directed through the bypass valve assembly 204*a* via the seventh irrigation channel 215*g* is transferred or directed to the third irrigation channel 215*c* which directs the fluid to the bypass inlet 514 defined in the cover 400. Fluid then passes through the bypass channel 516 (seen in FIG. 7B) defined between the cover 400 and the manifold 600 and then subsequently out of the cover 400 through the bypass outlet 518. The fluid is then directly deposited into the venturi reservoir 282 as seen in FIG. 9A where it may then be sent along the aspiration/suction path described above upon manipulation of the venting and suction valve assemblies 204*d*, 204*b*.

In certain embodiments, fluid initially within the irrigation reservoir 209 may be bypassed directly to the venturi reservoir 282 by being drawn through the second irrigation channel 215*b* which in turn leads to the bypass valve assembly 204*a*. From there, the fluid may be transferred to the third irrigation channel 215*c* which will then permit the fluid to ultimately flow into the venturi reservoir 282 in the same sequence discussed above.

Figure 12:
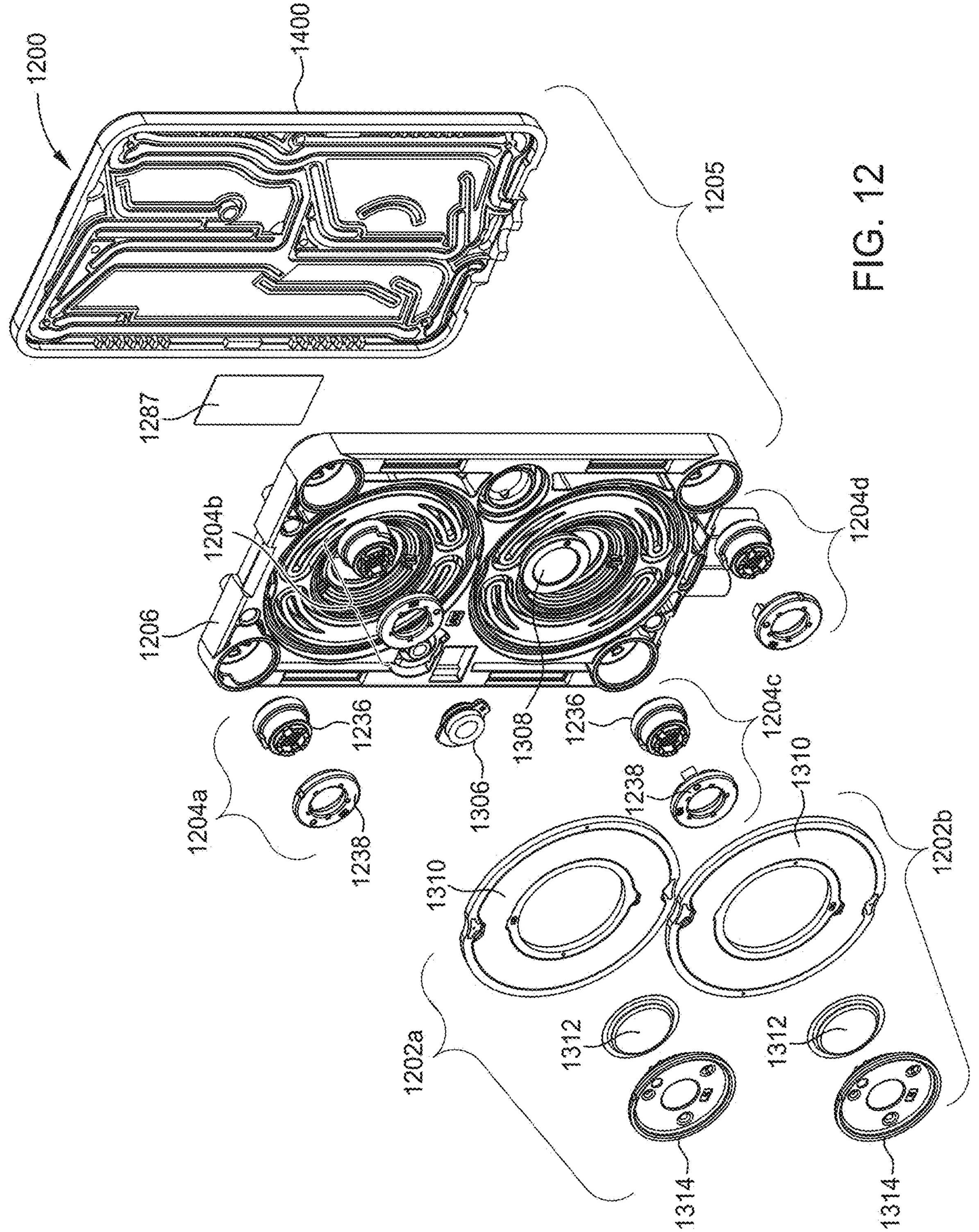
FIG. 12 is an exploded perspective view of another example surgical cassette including a base and a cover, according to certain embodiments.

FIG. 12 is an exploded perspective view of another example surgical cassette 1200, which may be operably coupled to a console of an ophthalmic surgical system (e.g., console 100 of ophthalmic surgical system 10 illustrated in FIGS. 1A-1B), according to certain embodiments. The surgical cassette 1200 has a housing 1205, which includes a base 1206 and a cover 1400 that is coupled to a frontside of the base 1206.

Disposed on a backside of the base 1206 are a plurality of valve assemblies 1204*a-d* arranged at each of the four corners of the base 1206, and a plurality of pump assemblies 1202*a-b* that are disposed in a stacked, central location relative to the base 1206. The backside of the base 1206 is configured to interact with the surgical console 100, while the frontside of the base 1206 provides an interface for engagement with the cover 1400. A filter 1287 is disposed between the base 1206 and the cover 1400. Each of the plurality of valve assemblies 1204*a-d* comprises both a valve body 1302 and a valve retaining ring 1304. Each of the plurality of pump assemblies 1202*a-b* comprises a pump elastomer 1310, a diaphragm 1312, and a diaphragm retainer ring 1314. Also disposed within the backside of the base 1206 is a venturi port seal 1306 and a pressure sensor seal 1308.

The surgical cassette 1200 is substantially similar in function to surgical cassette 200, and thus, comprises similarly functioning components thereto. However, unlike the surgical cassette 200, the surgical cassette 1200 does not include a manifold (e.g., manifold 600). Accordingly, in certain examples, surgical cassette 1200 may be described as a "two-layer" construction, whereas surgical cassette 200 may be described as a "three-layer" construction in certain examples.

Figure 13B:
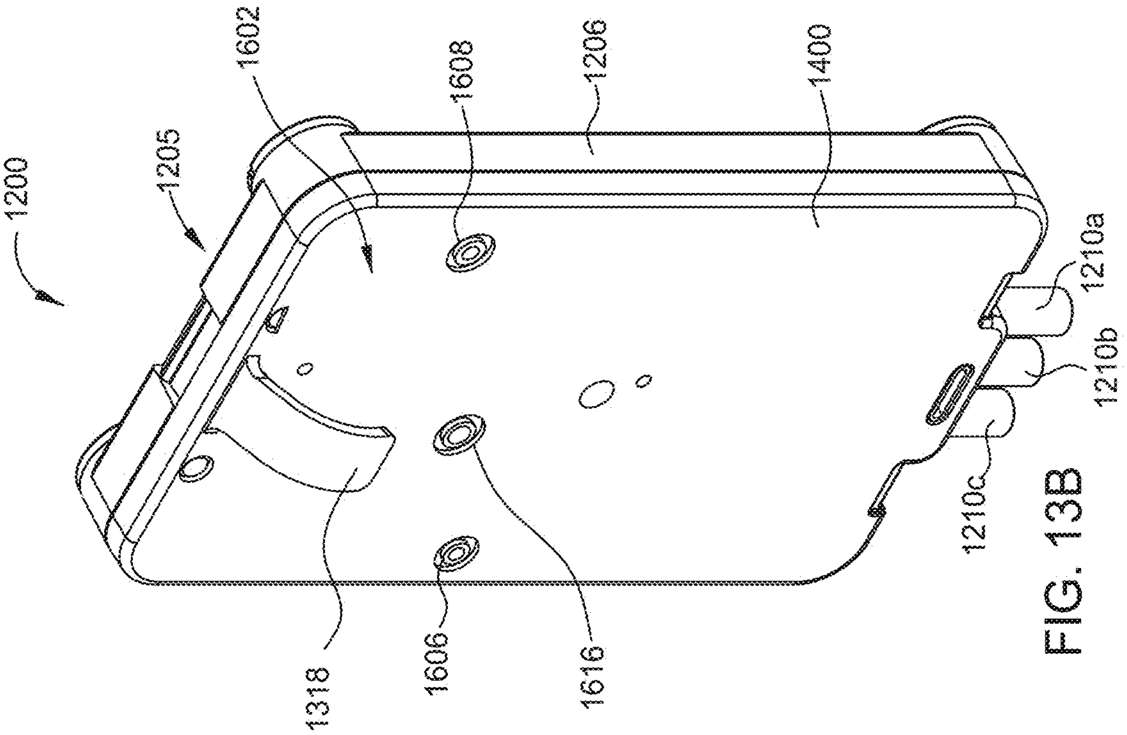
FIG. 13B is a frontside isometric view of the example surgical cassette of FIG. 13A, according to certain embodiments.
Figure 13A:
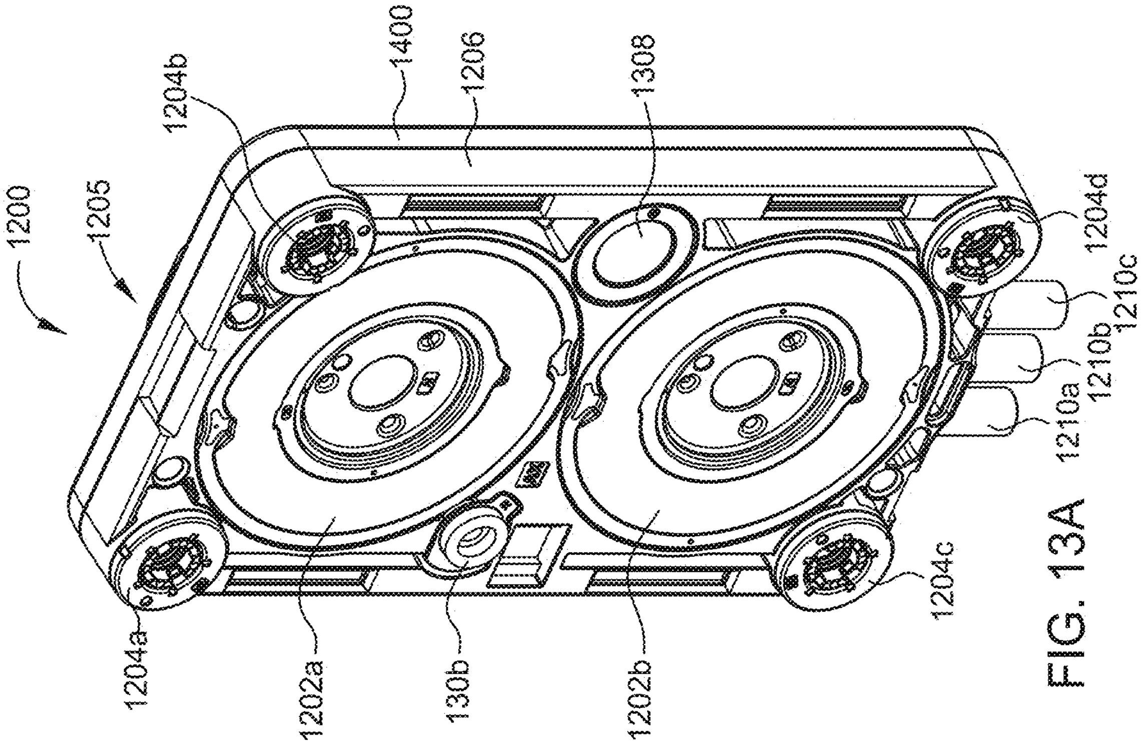
FIG. 13A is a backside isometric view of the example surgical cassette of FIG. 12, according to certain embodiments.
Figure 14B:
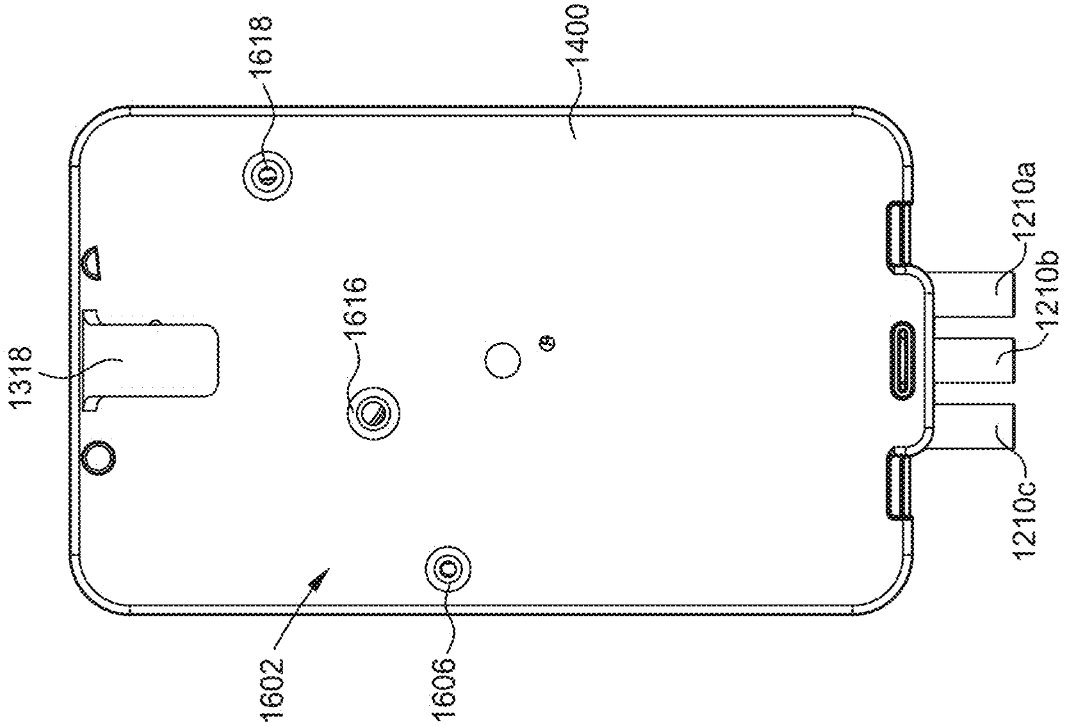
FIG. 14B is a frontside elevation view of the example surgical cassette of FIG. 14A, according to certain embodiments.
Figure 14A:
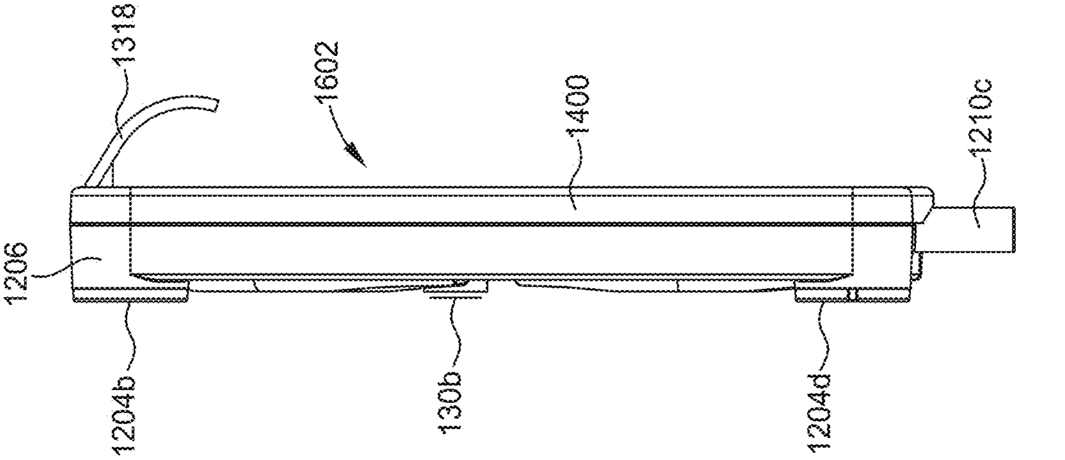
FIG. 14A is a right side elevation view of the example surgical cassette of FIG. 12, according to certain embodiments.

FIG. 13A is a backside isometric view of the example surgical cassette 1200, according to certain embodiments. FIG. 13B is a frontside isometric view of the example surgical cassette 1200, according to certain embodiments. For clarity, FIG. 12 and FIGS. 13A and 13B are herein described together. FIG. 14A is a right side elevation view of the example surgical cassette of FIG. 12, according to certain embodiments. FIG. 14B is a frontside elevation view of the example surgical cassette of FIG. 14A, according to certain embodiments. For clarity, FIGS. 13A and 13B and FIGS. 14A and 14B are herein described together.

Surgical cassette 1200 has the housing 1205, including the base 1206, the cover 1400 coupled to base 1206. The base 1206 has a plurality of inlet/outlet ports 1210 including an aspiration port 1210*a*, an admin port 1210*b*, and an irrigation port 1210*c*, which provide pressure and/or fluid communication between inside and outside of the housing 1205. Fluid lines (e.g., tubing) may be coupled between each port 1210*a-c* and a corresponding component of fluidics subsystem 110 and/or a corresponding handpiece 112*a-c* (shown in FIGS. 1A-1B).

As shown in FIG. 13A, surgical cassette 1200 includes two pump assemblies 1202 (1202*a-b*), which provide a source of pressure and/or vacuum, and four valve assemblies 1204 (1204*a-d*), which control pressure and/or fluid communication within the surgical cassette 1200. In certain other embodiments, there may be only one pump assembly or more than two pump assemblies. In certain other embodiments, there may be more or less than four valve assemblies (e.g., two to six valve assemblies).

Generally, pump assemblies 1202 and valve assemblies 1204 are substantially similar in structure and function to pump assemblies 202 and valve assemblies 204, respectively.

In certain embodiments, an external source of pressure and/or vacuum is coupled to the surgical cassette 1200. In such embodiments, the external source may be either in place of or in addition to the pump assemblies 1202.

In certain embodiments, one of the first pump assembly 1202*a* or second pump assembly 1202*b* provides a source of pressure (e.g., to create a driving force for fluid irrigation), while the other one of the first pump assembly 1202*a* or second pump assembly 1202*b* provides a source of vacuum (e.g., to create suction for fluid aspiration) within surgical cassette 1200. The first pump assembly 1202*a* and second pump assembly 1202*b* may be peristaltic pumps or any other suitable type of pump for generating pressure and/or vacuum. In certain embodiments, each of the first pump assembly 1202*a* and the second pump assembly 1202*b* is configured to engage with one or more rollers of a roller pump disposed on a surgical console, such as console 100. For example, when the surgical cassette 1200 is coupled to the console 100, the pump elastomer 1310 of each pump assembly 1202*a*, 1202*b* may be contacted against one or more rollers of a roller pump on the console 100. Thereafter, during use, manual forces provided by the rollers rolling along and pressing against the pump elastomers 1310, as driven by the pump, may drive fluid within the corresponding pump assembly 1202*a* or 1202*b*, and thus surgical cassette 200, to generate pressure or vacuum as needed.

In certain embodiments, the first pump assembly 1202*a* and second pump 1202*b* assembly are identical to each other. For example, the pump elastomer 1310 of each pump assembly 1202*a*, 1202*b* comprises a dual segmented volume that cancels pressure pulsations within the pump assembly and is comprised of a two-shot manufacturing design, i.e., silicone rubber or other elastomeric material over a plastic substrate. However, the pump elastomer 1310 may further comprise more or less than two segmented volumes (e.g., one to four or more segments).

Valve assemblies 1204 are coupled to base 1206. Valve assemblies 1204 function cooperatively to control pressure and/or fluid communication within and through surgical cassette 1200. In the illustrated embodiments, surgical cassette 1200 includes a first or bypass valve assembly 1204*a*, a second or suction valve assembly 1204*b*, a third or irrigation valve assembly 1204*c*, and a fourth or venting valve assembly 1204*d*. As shown, in the embodiments of FIG. 13A, the four valve assemblies 1204 are arranged at the four corners of the base 1206 and surrounding the two pump assemblies 1202, which are arranged towards a center of the base 1206. However, in certain other embodiments, pump assemblies 1202 and valve assemblies 1204 may have any other suitable arrangement.

In certain embodiments, valve assemblies 1204 may be operated to route fluid flow selectively between multiple channels of the housing 1205, as described in more detail above with respect to FIGS. 9A and 9B. For example, first valve assembly 1204*a* and third valve assembly 1204*c* may be in pressure and/or fluid communication with first pump assembly 1202*a* and port 1210*a* to provide aspiration through port 1210*a*, and/or infusion through the infusion port 1606 disposed on the cover 1400 during an operation, and second valve assembly 1204*b* and fourth valve assembly 1204*d* may be in pressure and/or fluid communication with second pump assembly 1202*b* and port 1210*c* to provide irrigation through port 1210*c* during the same operation, and/or suction through the suction port 1608. In certain embodiments, port 1210*b* may be an auxiliary port that is inactive during the operation and instead may be used to provide maintenance access for servicing surgical cassette 1200 between operations.

As shown in FIGS. 13B and 14B, a frontside of the cover 1400 comprises a substantially smooth outer surface 1602 and an ergonomic finger loop 1318, which provides the user an easy way to grip the cover 1400 when coupling and decoupling the surgical cassette 1200 to and from the surgical console 100. In certain embodiments, the cover 1400, and thus the surgical cassette 1200, may be configured or specialized for posterior eye procedures. For example, as seen in FIG. 13B, the cover 1400 comprises a suction port 1608 and an infusion port 1606 disposed on its outer surface 1602 and defined therethrough, as detailed further below with respect to FIGS. 16A and 16B. Also disposed within the frontside of the cover 1400 is a drain port 1616.

Figure 15B:
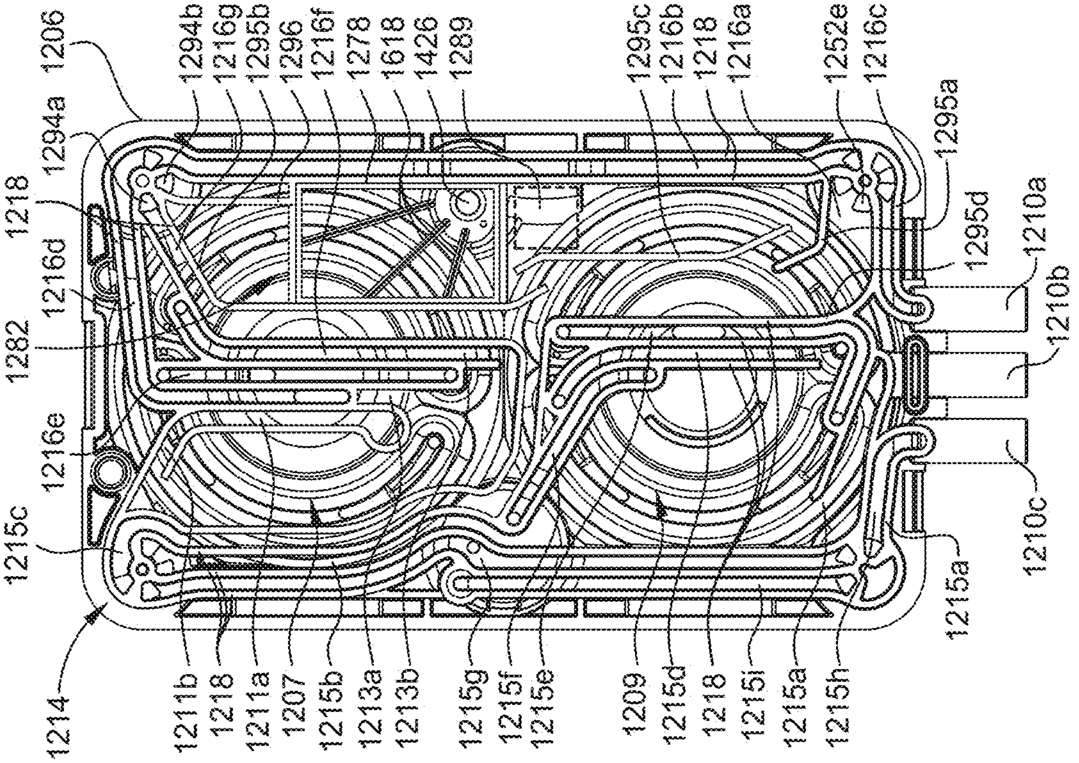
FIG. 15B is a front elevation view of the base of the surgical cassette of FIG. 15A, according to certain embodiments.
Figure 15A:
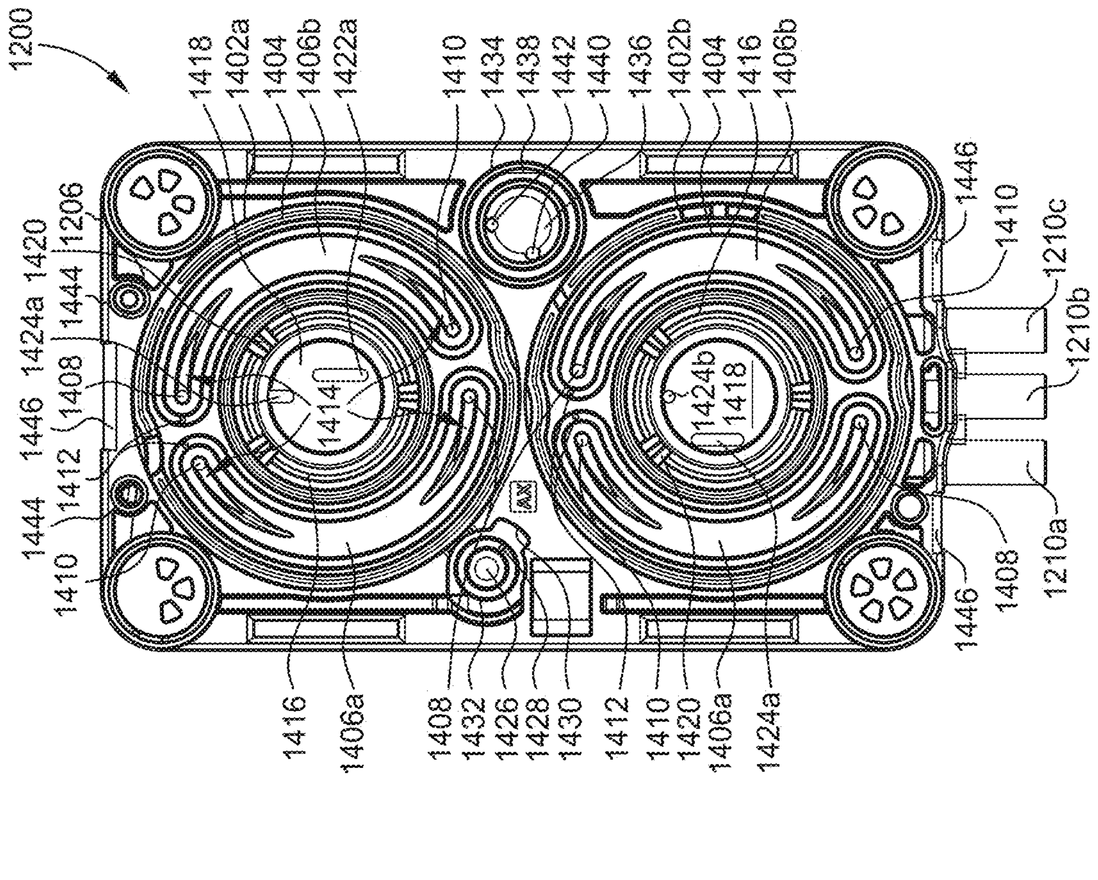
FIG. 15A is a back elevation view of the base of the surgical cassette of FIG. 12 with the pump assemblies, the pressure sensor seal, and the venturi port seal removed, according to certain embodiments.

FIG. 15A shows a backside elevation view of surgical cassette 1200 with the first and second pump assemblies 1202*a-b*, the venturi port seal 1306, and the pressure sensor seal 1308 removed from the base 1206 to show the surfaces and related fluid channels disposed there beneath. Generally, the backside of base 1206 is substantially similar to that of base 206.

For example, disposed beneath the first pump assembly 1202*a* and the second pump assembly 1202*b* are a first well 1402*a* and a second well 1402*b*, respectively. The first and second wells 1402*a*, 1402*b* comprise at least one semi-circular or substantially crescent shaped groove 1404 that accommodates or seats the pump elastomer 1310 therein. However, in certain embodiments, more than two wells 1402 may be utilized in combination with a pump assembly 1202. A small air hole 1412 defined within each groove 1404 permits air trapped beneath the pump elastomer 1310 to escape when the pump elastomer 1310 is being installed during the manufacturing process. In certain embodiments, each of the first and second wells 1402*a*, 1402*b* comprises a first pump channel 1406*a* and second pump channel 1406*b*, each pump channel 1406*a*, 1406*b* further comprising at least one pump channel inlet 1408 defined at one end of the pump channel 1406 and at least one pump channel outlet 1410 defined at an opposing end of the pump channel 1406. Also defined within each pump channel 1406 and adjacent to each inlet 1408 and outlet 1410 is a semi-circular pump channel trough 1414 that, in certain embodiments, comprises a tapered width and depth along its arc length, the trough 1414 terminating at a corresponding inlet 1408 or outlet 1410. Each trough 1414 may have a maximum width and depth adjacent to the corresponding inlet 1408 or outlet 1410 that narrows in width and becomes shallower along its arc length until becoming flush with the surface of the pump channel 1406. Each well 1402*a*, 1402*b* also comprises an angled surface 1416 that is disposed more radially inward relative to the pump channels 1406, the angled surface 1416 providing a transition from the pump channels 1406 to bottom surface 1418.

Disposed within the angled surface 1416 is a plurality of retainer ring keyways 1420 which are configured to accommodate a matching plurality of tabs disposed on the diaphragm retaining rings 1314, for proper orientation of the diaphragm retaining rings 1314 within each well 1402. The bottom surface 1418 of the first well 1402*a*, which corresponds to the aspiration pump assembly 1202*a*, comprises a sensor inlet 1422*a* and a sensor outlet 1424*a*. In certain embodiments, both sensor inlet 1422*a* and sensor outlet 1424*a* of the first pump assembly 202*a* comprises an elongated or extended shape. The bottom surface 1418 of the second well 1402*b*, which corresponds to the irrigation pump assembly 1202*b*, also comprises a corresponding sensor inlet 1422*b* and a sensor outlet 1424*b*. However, in certain embodiments, only the sensor inlet 1422*b* comprises an elongated or extended shape, while the sensor outlet 1424*b* comprises a substantially circular shape. The sensor inlets 1422*a*, 1422*b* and the sensor outlet 1424*a* of the first well 1402*a* comprise an elongated shape so as to minimize the effects of air bubbles and assists in optimizing the path of the fluid as it is being pumped by each respective pump assembly 1202*a*, 1202*b*.

Also seen in FIG. 15A is a venturi port connection 1432, which accommodates the venturi port seal 1306 therein. A seal tab 1430 ensures that the venturi port seal 1306 is properly orientated to the base 1206. The venturi port connection 1432 also comprises an air hole 1428 so that air may escape as the venturi port seal 1306 is being coupled to the venturi port connection 1432 during the manufacturing process. A venturi port 1426 is further defined within a center of the venturi port connection 1432 that allows a venturi pump to be connected thereto for providing a negative or vacuum pressure to a venturi reservoir 1282.

The surgical cassette 1200 further includes a pressure sensor ring 1434, which accommodates the pressure sensor seal 1308 therein. An air hole 1438 defined in the pressure sensor ring 1434 allows air to escape as the pressure sensor seal 1308 is being coupled to the pressure sensor ring 1434 during manufacturing. At the center of the pressure sensor ring 1434 is a sensor surface 1436 that comprises a pressure sensor inlet 1440 and a pressure sensor outlet 1442. When the surgical cassette 1200 is coupled to the console 100, a pressure sensor disposed within the console 100 measures the fluid pressure beneath the pressure sensor seal 1308 as fluid is flowing in from the pressure sensor inlet 1440, across the sensor surface 1436, and then exits through the pressure sensor outlet 1442.

The backside of the base 1206 further comprises one or more locating features 1444 configured to interact or engage with a corresponding plurality of pins disposed in the console 100 to ensure that the surgical cassette 1200 is properly orientated when coupled to the console 100. Additionally, in certain embodiments, a set of sliding features 1446 are configured to interact or engage with a corresponding set of console rollers disposed on the console 100 for retaining the surgical cassette 1200 on the console 100.

FIG. 15B shows a frontside elevation view of the base 1206 shown in FIG. 15A, according to certain embodiments. As shown, a plurality of channels 1215*a-i* and 1216*a-g* are formed in housing 1205. In certain embodiments, the first plurality of channels 1215*a-i* correspond to an irrigation path within the surgical cassette 1200, while the second plurality of channels 1216*a-g* correspond to an aspiration path within the surgical cassette 1200. In certain embodiments, the venturi reservoir 1282 and an adjacent or overlaid filter pocket 1278 are formed in a righthand portion of the base 1206, while a waste reservoir 1207 and an irrigation reservoir 1209 are formed in a lefthand portion of the base 1206, the waste reservoir 1207 being vertically disposed over the irrigation reservoir 1209. The plurality of channels 1215*a-i* and 216*a-f* are arranged to provide a plurality of independent fluid paths between pump assemblies 1202, valve assemblies 1204, venturi reservoir 1282, filter pocket 1278, waste reservoir 1207, irrigation reservoir 1209, and inlet/outlet ports 1210.

Figure 16B:
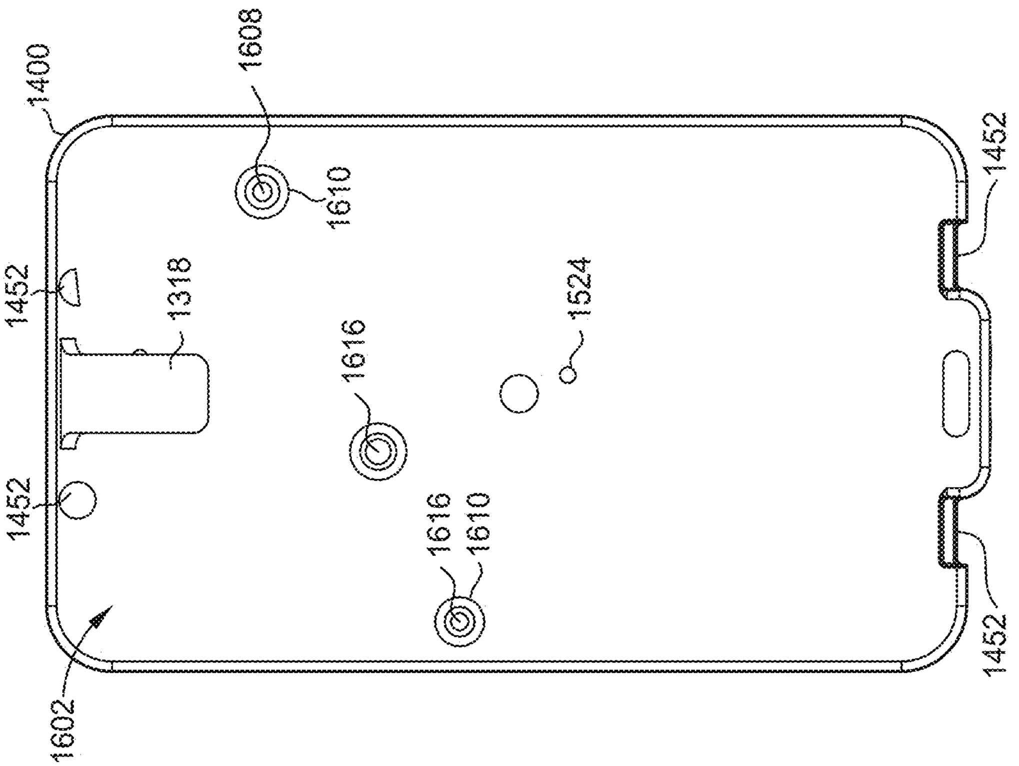
FIG. 16B is a front elevation view of the cover of the surgical cassette of FIG. 16A, according to certain embodiments.
Figure 16A:
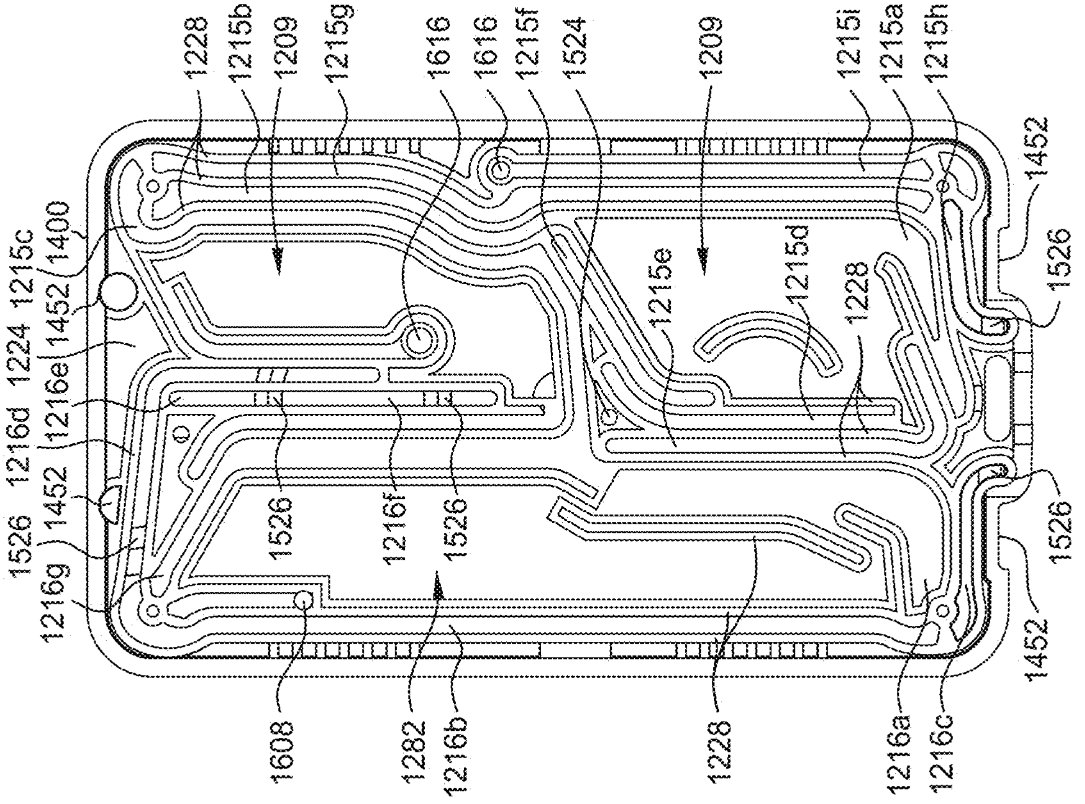
FIG. 16A is a back elevation view of the cover of the surgical cassette of FIG. 12, according to certain embodiments.

Each channel 1215*a-i* and 1216*a-g* is longitudinally defined in a first direction parallel to a plane of housing 1205. Each channel 1215, 1216 includes sidewalls 1218 oriented perpendicular to the first direction which, when combined with a corresponding plurality of faces 1228 disposed on the cover 1400 as seen in FIGS. 16A-16B, enclose the corresponding channel 1216 therebetween. The plurality of channels 1215, 1216 are sealingly enclosed through contact between the sidewalls 1218 formed on frontside 1214 of base 1206 and a corresponding or mirror image set of faces 1228 extending from inner surface 1224 of cover 1400. In order to effect sealing, the sidewalls 1118 and corresponding faces 1228 are molded in certain embodiments to each comprise a cross-section which is substantially half-circular in shape which, when assembled together (e.g., via ultrasonic welding), ensure precise alignment between opposing sides. In some other embodiments, the plurality of channels 1215, 1216 may be formed in cover 1400 instead of base 1206 and sealingly enclosed through contact between a backside surface of cover 1400 and a corresponding frontside face of base 1206. In some other embodiments, base 1206 and cover 1400 may be integrally formed as a single piece. In such embodiments, base 1206 and cover 1400 may be injection molded with the use of a slide technique.

Similar to surgical cassette 200, FIG. 15B shows the venturi reservoir 1282 being disposed inside housing 1205 of surgical cassette 1200 between base 1206 and cover 1400 according to certain embodiments. In general, venturi reservoir 1282 facilitates connection to a vacuum source for suction of fluids during venturi operations, provides a fluid volume sink for normal vacuum venting within the surgical cassette 1200, and provides a fluid volume sink for venting vacuum pressure that may build-up within surgical cassette 1200 in the event of a post-occlusion break surge. In certain embodiments, the venturi reservoir 1282 also allows air to separate from liquid and then evacuate out the cassette 1200 through the surgical console during normal aspiration/suction use with venturi vacuum.

Surgical cassette 1200 may be coupled to an external vacuum source (e.g., a venturi source or pump) disposed in console 100. Vacuum pressure from the external vacuum source is applied to venturi reservoir 1282 through a suction port 1608 in cover 1400 seen in FIGS. 13B and 14B. In the illustrated embodiments, suction port 1608 is a circular opening. However, other shapes, such as elongated slots, are further contemplated. In certain embodiments, vacuum pressure within venturi reservoir 1282 is about 720 mmHg. In certain embodiments, maximum airflow through suction port 1608 is about 1.2 standard liters per minute. The external vacuum source is configured to apply vacuum pressure to venturi reservoir 1282 through a vacuum flow path that passes, upstream to downstream, from venturi port 1426 through the filter 1287 in filter pocket 1278, where the air is filtered before passing up through suction port 1608 in cover 1400 and then reaching the external vacuum source.

Filter pocket 1278 and filter 1287 are in pressure communication with the external vacuum source and suction port 1608 in cover 1400. The location of filter pocket 1278, and thus, filter 1287, overlays at least a portion of venturi reservoir 1282, thus enabling the use of a more compact housing 1205 compared to other designs. An upstream side of filter 1287 faces towards base 1206. A downstream side of filter 1287 faces towards cover 1400. Filter 1287 seals with base 1206 and cover 1400 to prevent liquid from leaking around filter 1287. Filter 1287 permits air to pass through while blocking liquid from passing to the downstream side of filter 1287 and into the external vacuum source. In certain embodiments, filter 1287 is directly coupled to base 1206, such as by ultrasonic welding, while in other embodiments the filter 1287 may be directly coupled to the cover 1400. In certain embodiments, filter 1287 is hydrophobic, and thus impermeable to aqueous fluids. In certain embodiments, a plurality of filter support ribs 1618 are disposed on the inner surface of the base 1206 and within the filter pocket 1278. When in use, the filter support ribs 1618 provide structural support to the filter 1287 so that it does not sag, sink, or otherwise deform under changing pressures. Additionally, because each of the filter support ribs 1618 contact the edges of the filter pocket 1278 but not each other, any air bubbles caught therein have sufficient space to move down towards the vacuum pathway.

Venturi reservoir 1282 includes a level sensor area 1289 defined in base 1206. Suction port 1608 is disposed above level sensor area 1289. Level sensor area 1289 is disposed along an optical path of a light sensor in console 100 that is used to determine a fluid level in venturi reservoir 1282. In certain embodiments, the light sensor is an infrared sensor, a single camera sensor, or a complementary metal oxide semiconductor (CMOS) sensor. The relatively small size or footprint of level sensor area 1289 enables the use of a more compact housing 1205 compared to other designs.

The presence of air bubbles in or near level sensor area 1289 may interfere with accurate detection of the fluid level in venturi reservoir 1282 because the air bubbles can obscure the air-liquid interface. Therefore, in certain embodiments, a plurality of air baffles 1295 (1295*a*-*d*) as seen in FIG. 15B are disposed within venturi reservoir 1282 and the irrigation reservoir 1209 in order to divert air bubbles away from level sensor area 1289 and irrigation path, respectively. The plurality of air baffles 1295 are integral with base 1206 and contact cover 1400 when cover 1400 is coupled to base 1206. In some other embodiments, the plurality of air baffles 1295 are integral with cover 1400 instead of base 1206.

A lower air baffle 1295*a* is disposed above port 1252*e* and extends up and to the left of the viewer in FIG. 15B. An upper air baffle 1295*b* is disposed below port 1294*b* and extends down and to the left of the viewer in FIG. 15B. Air baffles 1295*a*-*b* form corresponding channel-like structures within venturi reservoir 1282 that begin at corresponding ports 1252*c*, 1294*b* and end on the left side of venturi reservoir 1282. For example, first channel 1216*a* corresponds to a portion of venturi reservoir 1282 below lower air baffle 1295*a*. A central air baffle 1295*c* is located to the right of the respective ends of air baffles 1295*a*-*b* and extends from below to above level sensor area 1289. The position of central air baffle 1295*c* prevents air bubbles from crossing level sensor area 1289 even after the air bubbles pass above lower air baffle 1295*a* and below upper air baffle 1295*b*, respectively. An opening between lower air baffle 1295*a* and central air baffle 295*c* provides a path for equalization of fluid on the left and right sides of central air baffle 1295*c*, so that the fluid level in level sensor area 1289 corresponds to the actual fluid level in venturi reservoir 1282. An opening between upper air baffle 1295*b* and central air baffle 1295*c* provides a path for the flow of air bubbles from the left side of central air baffle 1295*c* to suction port 1608 without crossing level sensor area 1289.

A liquid baffle 1296 is disposed within venturi reservoir 1282 above level sensor area 1289. Liquid baffle 1296 is configured to reduce or prevent liquid from entering suction port 1608 in cover 1400, such as during bubbling, frothing, or overflowing of the liquid contained in venturi reservoir

1282. Like air baffles 1295, liquid baffle 1296 is integral with base 1206 and contacts cover 1400 when cover 1400 is coupled to base 1206.

In certain embodiments, the waste reservoir 1207 comprises a drain channel 1211*a* formed therein, which terminates at one end at the drain port 1616 defined in the cover 1400 as detailed further below. In certain embodiments, an opposing end of the drain channel 1211*a* comprises an angled or bent portion 1211*b* that serves to form a lip or rim to the drain channel 1211*a*. As fluid collects within the waste reservoir 1207, the fluid can only move into the drain channel 1211*a* after cresting the angled portion 1211*b*. When fluid flow has stopped, the fluid within the waste reservoir 1207 will remain below the angled portion 1211*b* and will not enter the drain channel 1211*a*. In this manner, the angled portion 1211*b* ensures that when fluid flow through the cassette 1200 is reversed, a defined volume of fluid will always be available within the waste reservoir 1207, thereby preventing air from being pumped to other portions of the surgical cassette 1200. In certain embodiments, the waste reservoir 1207 further comprises reflux structures 1213*a*, 1213*b* that are formed by a parallel pair of vertically orientated sidewalls 1218. When a reverse or reflux flow through the cassette 1200 is required, the reflux structures 1213*a*, 1213*b* serve to draw fluid from a deeper position within the waste reservoir 1207 beneath the respective pump channel outlets 1410.

FIGS. 16A and 16B illustrate opposing views of the cover 1400 in greater detail. FIG. 16A shows a backside of cover 1400 comprising an inner surface 1224 with faces 1228 that correspond to sidewalls 1218 to form channels 1215, 1216 disposed between the cover 1400 and base 1206. Additionally, FIG. 16A depicts the corresponding areas of inner surface 1224 that partially define the reservoirs in surgical cassette 1200 (e.g., the venturi reservoir 1282, irrigation reservoir 1209, and waste reservoir 1207) as formed by the coupling of the cover 1400 and base 1206. FIG. 16B shows a frontside of cover 1400 comprising an outer surface 1602. The cover 1400 further comprises the suction port 1608 that is in fluid communication with the venturi port 1426 when the cover 1400 is coupled to the base 1206. Also defined through the cover 1400 are the drain port 1616, the infusion port 1606, and stacking features 1452.

In certain embodiments, the cover 1400 comprises a plurality of flow path optimization features 1526 formed therein which, when the cover 1400 is joined with the base 1206 to form respective channels 1215, 216, cooperate with the sidewalls 1218 to provide a smooth flow path therein. In certain embodiments, the flow path optimization features 1526 may comprise angled or sloping surfaces to compensate for a corresponding angle, slope, or other non-uniform surface within the portions of the channels 1215, 1216 disposed on the base 1206.

In certain embodiments, both the infusion port 1606 and the suction port 1608 comprise a pair of sterile guards 1610 disposed on the outer surface 1602, which each comprise at least one angle indicator (described above with reference to manifold 600) that assist outside connections or tubing to couple to each of the ports 606, 608 with the proper orientation. Each port 606, 608, in certain embodiments, also comprise at least one locking element (described above with reference to manifold 600) which is configured to lock or maintain the outside connection or tubing in fluid contact with the surgical cassette 1200 after being coupled to each respective port 606, 608.

In certain embodiments, the cover 1400 also comprises one or more sterilization ports 1524 defined therein which permits a sterilization gas such as ethylene oxide or its equivalent to pass there through during the manufacturing process so as to properly sterilize the internal components of the surgical cassette 1200.

In certain embodiments, simplified surgical cassettes are provided according to FIGS. 17A-21D. The simplified surgical cassette designs in FIGS. 17A-21D may be utilized in place of surgical cassette 200, and in combination with ophthalmic surgical system 10 and console 100, as described above. The simplified surgical cassette designs in FIGS. 17A-21D provide a simpler construction and a minimum number of parts, thereby making the manufacturing process of the surgical cassette easier and more efficient. In certain embodiments, the components or features described with reference to the simplified surgical cassettes in FIGS. 17A-21D may be substantially similar to corresponding components or features of surgical cassette 200. Note that while described with certain components or features, the simplified surgical cassettes in FIGS. 17A-21D may include more or less components or features than described. Further note that any fluid paths described with reference to FIGS. 17A-21D may include one or more channels, reservoirs, cavities, or other fluid-containing structures.

As shown in FIGS. 17A-17D, a surgical cassette 1700 comprises an aspiration path and an irrigation path; however, unlike the embodiments shown in FIGS. 2-6B and 9B, only a single pump assembly 1702 is provided, specifically along the aspiration path.

During use, fluid removed or suctioned from the eye of the patient enters an aspiration inlet 1704, where it is then drawn through a first aspiration path 1708 to an aspiration valve assembly 1706 by a negative pressure provided by the pump assembly 1702. In certain embodiments, the aspiration valve assembly 1706 comprises the same components, construction, and/or functions in the same manner as the valves 236 and valve assemblies 204 shown in FIGS. 2, 10A-10B, and 11A-11B, as described above. Dependent upon the configuration or orientation of the aspiration valve assembly 1706, fluid is then directed either to the pump assembly 1702 via a second aspiration path 1710, or directly into an aspiration reservoir 1712 via a third aspiration path 1714. In certain embodiments, when fluid enters the pump assembly 1702, the fluid also passes by an aspiration pressure sensor 1716 disposed in a center of, or adjacent to (e.g., downstream or upstream of, as indicated by 1716 in phantom), the pump assembly 1702 and configured to measure fluidic pressure in the pump assembly 1702 or second aspiration path 1710. The pump assembly 1702 comprises the same components, construction, and/or functions in the same manner as the pump assemblies 202 shown in FIGS. 2, 5A-6B, and 9B, as described above. After passing through the pump assembly 1702, fluid is directed through a fourth aspiration path 1718 and into the aspiration reservoir 1712. Excess fluid within the aspiration reservoir 1712 drains to an outside drain bag or receptacle through a drain port 1734.

The irrigation path within the surgical cassette 1700 comprises, for example, an administration inlet 1720 where fluid, which is to be flowed to the eye of the patient, first enters the surgical cassette 1700. The fluid passes through a first irrigation path 1722 before entering an irrigation valve assembly 1726. In certain embodiments, an irrigation pressure sensor 1724 is disposed within, or adjacent to, first irrigation path 1722 for monitoring pressure of fluid therein. In certain embodiments, the irrigation valve assembly 1726 comprises the same components, construction, and/or functions in the same manner as the valves 236 and valve assemblies 204 shown in FIGS. 2, 10A-10B, and 11A-11B, as described above. Dependent upon the configuration or orientation of the irrigation valve assembly 1726, fluid is then directed either to the aspiration reservoir 1712 via a second irrigation path 1728, or through an irrigation outlet 1730 and out of the surgical cassette 1700 via a third irrigation path 1732.

Figure 17B:
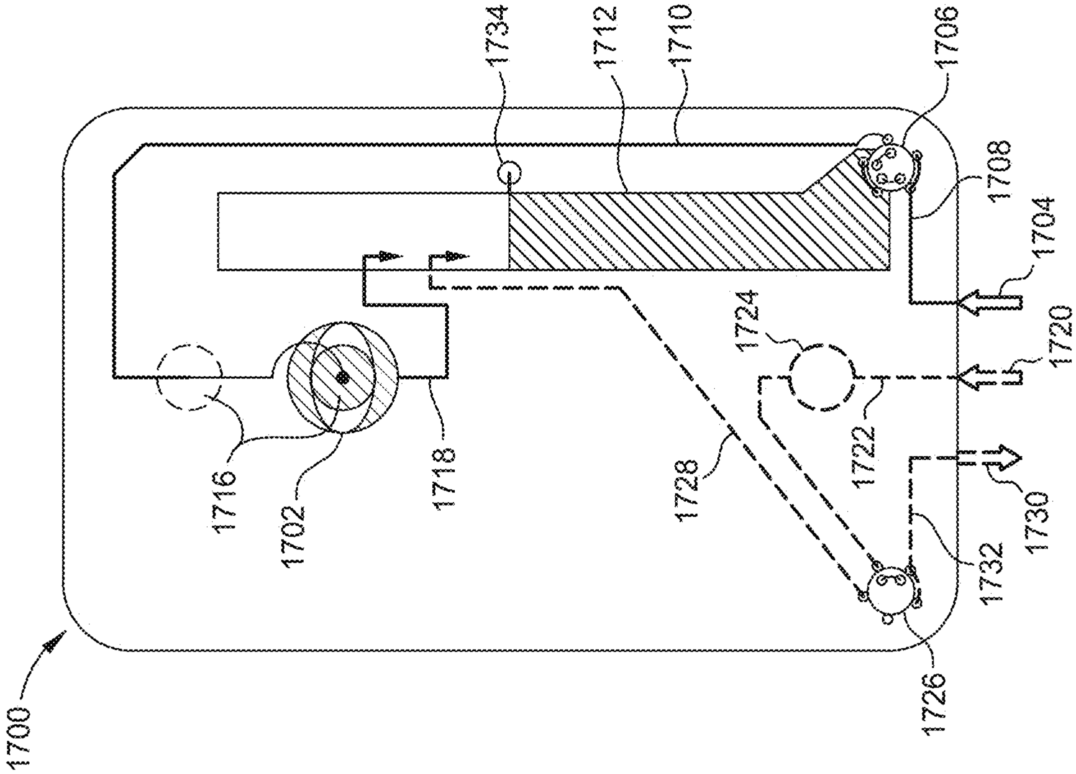
FIGS. 17A-17D are schematic views of a simplified surgical cassette design, according to certain embodiments.
Figure 17A:
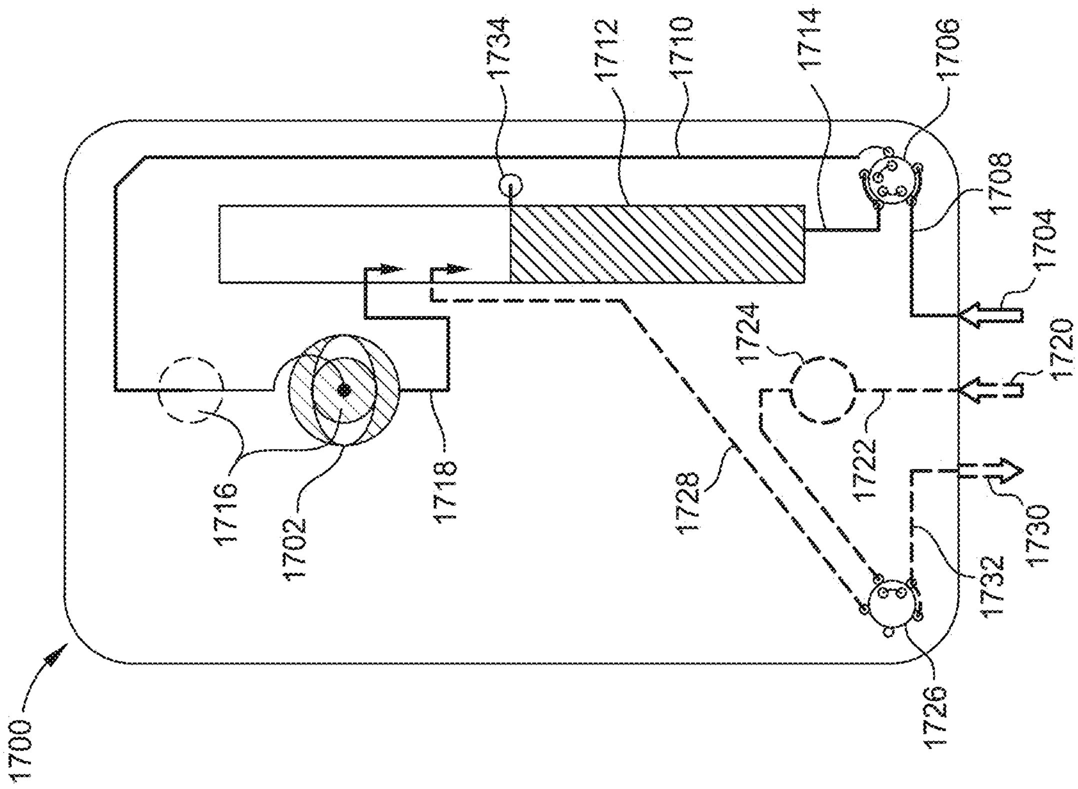
Figure 17D:
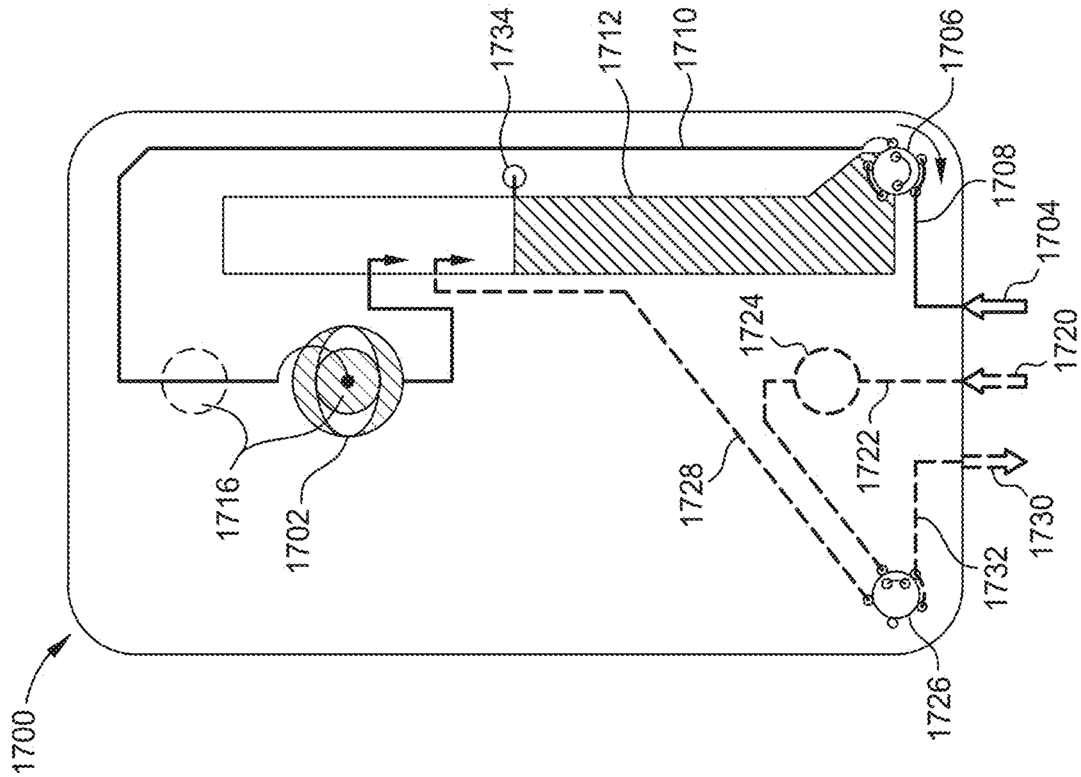
Figure 17C:
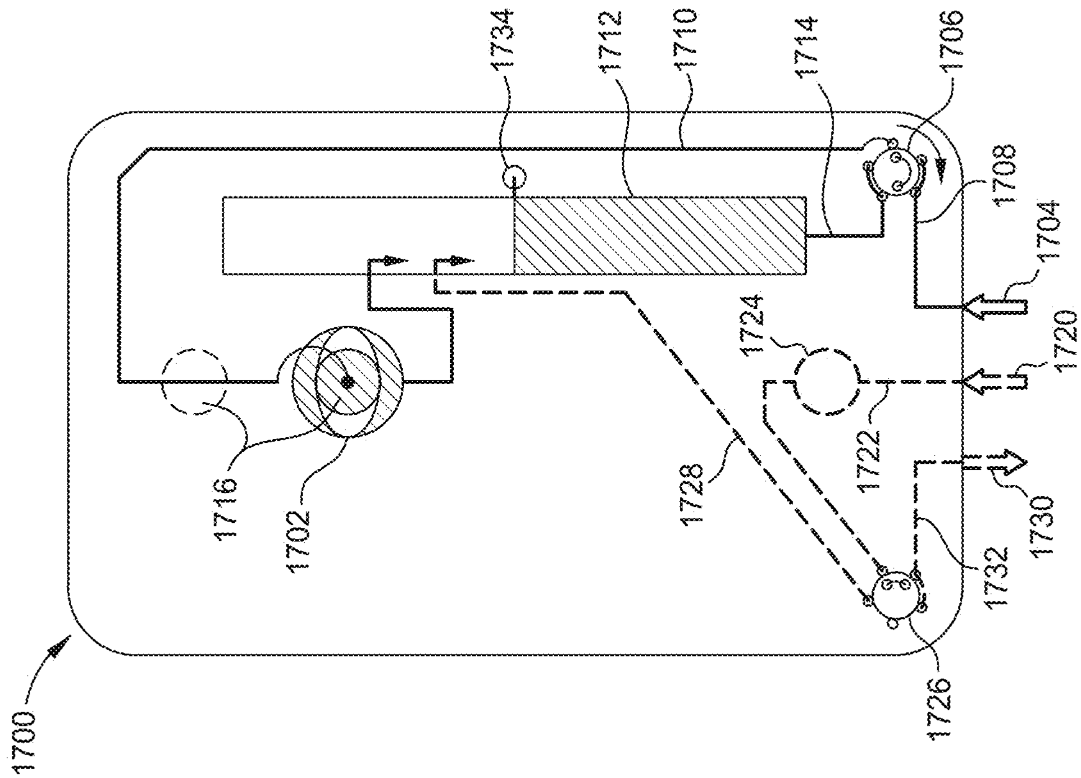

In certain embodiments, the aspiration valve assembly 1706 comprises a dual-path valve, as seen in FIGS. 17A-17B, which permits the aspiration valve assembly 1706 to maintain two open connections between multiple paths simultaneously. For example, open connections between the first aspiration path 1708 and the third aspiration path 1714, and between the second aspiration path 1710 and the third aspiration path 1714, may be maintained depending upon the current orientation of the aspiration valve assembly 1706. In certain other embodiments, the aspiration valve assembly 1706 comprises a single-path valve, as seen in FIGS. 17C-17D, which permits the aspiration valve assembly 1706 to only maintain one open connection between multiple paths, for example, between the first aspiration path 1708 and the third aspiration path 1714, or between the second aspiration path 1710 and the third aspiration path 1714, depending upon the current orientation of the aspiration valve assembly 1706. In certain embodiments, the aspiration valve assembly 1706 comprising a single-path valve rotates 360° so as to complete an entire vent cycle.

In certain embodiments, as seen in FIGS. 17B and 17D, the aspiration reservoir 1712 extends directly over one or more ports of the aspiration valve assembly 1706, which reduces any flow restriction between the aspiration reservoir 1712 and the aspiration valve assembly 1706 as caused by third aspiration path 1714, which may include one or more channels or other structures in FIGS. 17A and 17C.

Figure 18A:
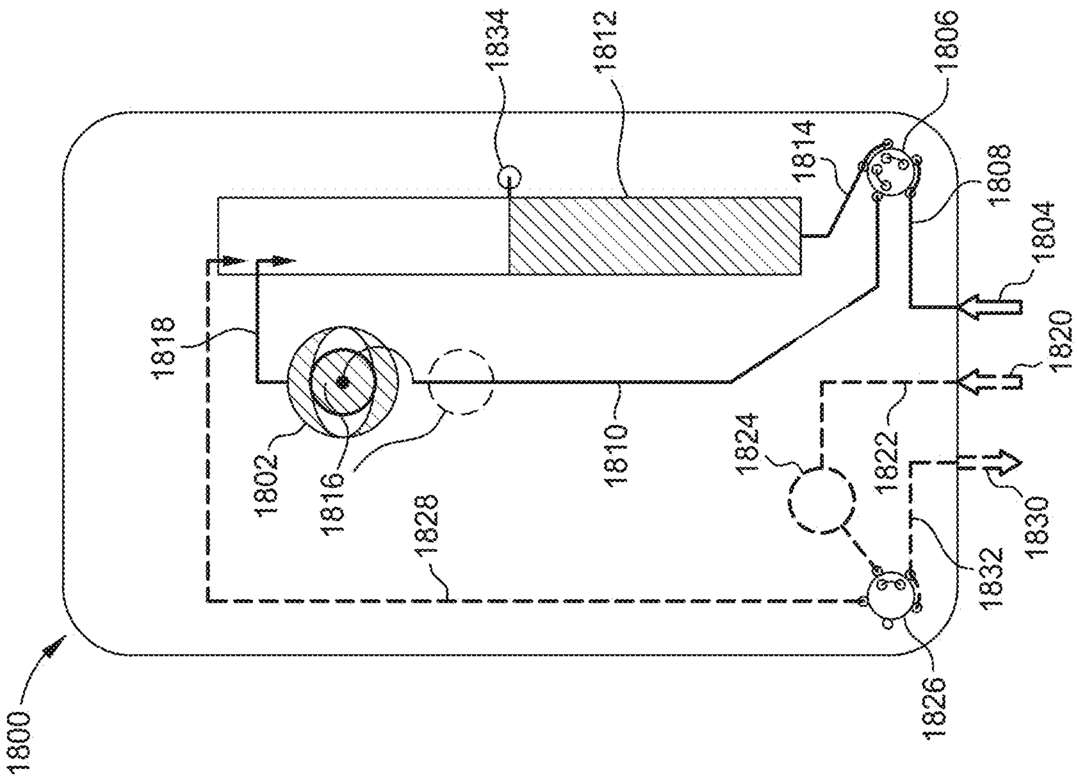
FIGS. 18A-18B is a schematic view of another simplified surgical cassette design, according to certain embodiments.
Figure 18B:
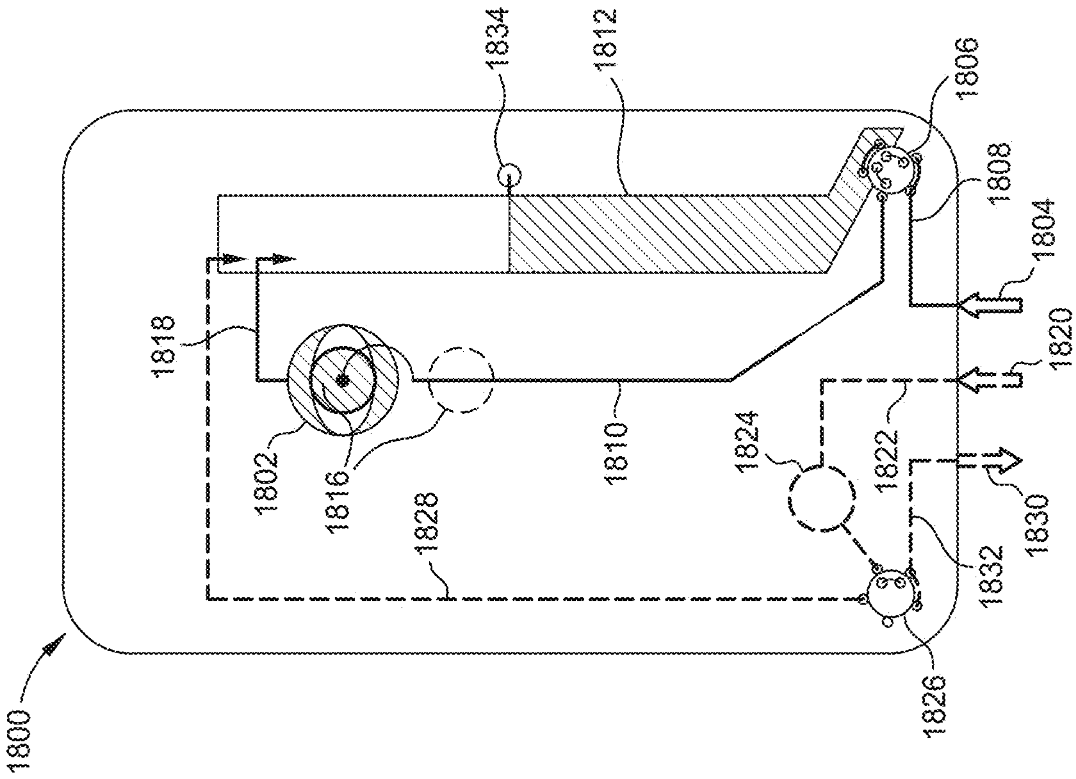

In FIGS. 18A-18B, a surgical cassette 1800 comprises an aspiration path, an irrigation path, and a single pump assembly 1802 provided specifically along the aspiration path.

During use, fluid removed or suctioned from the eye of the patient enters an aspiration inlet 1804, where it is drawn through a first aspiration path 1808 to an aspiration valve assembly 1806 by a negative pressure provided by the pump assembly 1802. In certain embodiments, the aspiration valve assembly 1806 comprises the same components, construction, and/or functions in the same manner as the valves 236 and valve assemblies 204 shown in FIGS. 2, 10A-10B, and 11A-11B, as described above. Dependent upon the configuration or orientation of the aspiration valve assembly 1806, fluid is then directed either to the pump assembly 1802 via a second aspiration path 1810, or directly into an aspiration reservoir 1812 via a third aspiration path 1814. In certain embodiments, the fluid first passes through an aspiration pressure sensor 1816 disposed within, or adjacent to, the second aspiration path 1810, and/or disposed at a center of or adjacent to (e.g., downstream or upstream of, as indicated by 1816 in phantom) the pump assembly 1802. The aspiration pressure sensor 1816 allows for monitoring fluidic pressure in the second aspiration path 1810. The pump assembly 1802 comprises the same components, construction, and/or functions in the same manner as the pump assemblies 202 shown in FIGS. 2, 5A-6B, and 9B as described above. After passing through the pump assembly 1802, fluid is directed through a fourth aspiration path 1818 and into the aspiration reservoir 1812. Excess fluid within the aspiration reservoir 1812 drains to an outside drain bag or receptacle through a drain port 1834.

The irrigation path within the surgical cassette 1800 comprises, for example, an administration inlet 1820, where fluid that is to be sent to the eye of the patient first enters the surgical cassette 1800. The fluid passes through a first irrigation path 1822 before entering an irrigation valve assembly 1826. In certain embodiments, an irrigation pressure sensor 1824 is disposed within, or adjacent to, first irrigation path 1822 for monitoring fluidic pressure therein. In certain embodiments, the irrigation valve assembly 1826 comprises the same components, construction, and functions in the same manner as the valves 236 and valve assemblies 204 shown in FIGS. 2, 10A-10B, and 11A-11B as described above. Dependent upon the configuration or orientation of the irrigation valve assembly 1826, fluid is then directed either to the aspiration reservoir 1812 via a second irrigation path 1828, or through an irrigation outlet 1830 and out of the surgical cassette 1800 via a third irrigation path 1832.

In certain embodiments, as seen in FIG. 18B, the aspiration reservoir 1812 extends directly over one or more ports of the aspiration valve assembly 1806, which reduces any flow restriction between the aspiration reservoir 1812 and the aspiration valve assembly 1806 as caused by third aspiration path 1814, which may include one or more channels or other structures in FIG. 18A.

Figure 19B:
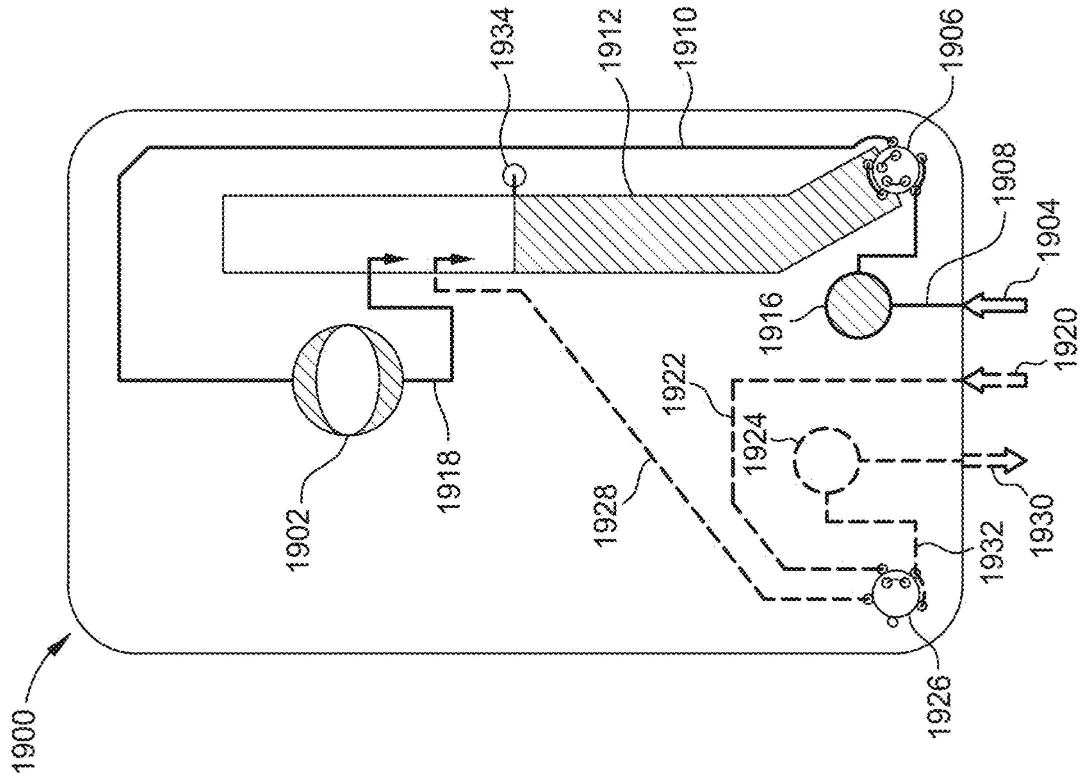
FIGS. 19A-19B is a schematic view of another simplified surgical cassette design, according to certain embodiments.
Figure 19A:
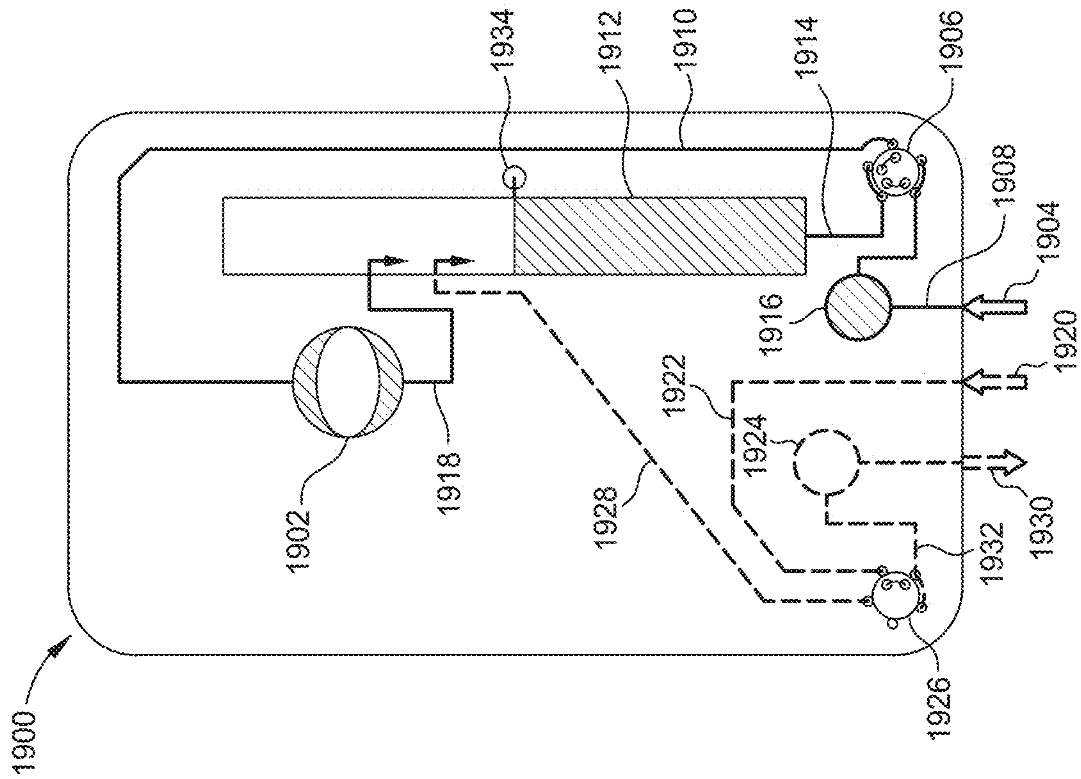

In FIGS. 19A-19B, a surgical cassette 1900 comprises an aspiration path, an irrigation path, and a single pump assembly 1902 provided specifically along the aspiration path.

During use, fluid removed or suctioned from the eye of the patient enters an aspiration inlet 1904, where it is drawn through a first aspiration path 1908 to an aspiration pressure sensor 1916, and then to an aspiration valve assembly 1906 by a negative pressure provided by the pump assembly 1902. In certain embodiments, the aspiration valve assembly 1906 comprises the same components, construction, and/or functions in the same manner as the valves 236 and valve assemblies 204 shown in FIGS. 2, 10A-10B, and 11A-11B as described above. Dependent upon the configuration or orientation of the aspiration valve assembly 1906, fluid is then directed either to the pump assembly 1902 via a second aspiration path 1910, or directly into an aspiration reservoir 1912 via a third aspiration path 1914. The pump assembly 1902 comprises the same components, construction, and/or functions in the same manner as the pump assemblies 202 shown in FIGS. 2, 5A-6B, and 9B as described above. After passing through the pump assembly 1902, fluid is directed through a fourth aspiration path 1918 and into the aspiration reservoir 1912. Excess fluid within the aspiration reservoir 1912 drains to an outside drain bag or receptacle through a drain port 1934.

The irrigation path within the surgical cassette 1900 comprises, for example, an administration inlet 1920, where fluid that is to be sent to the eye of the patient, first enters the surgical cassette 1900. The fluid passes through a first irrigation path 1922 before entering an irrigation valve assembly 1926. In certain embodiments, the irrigation valve assembly 1926 comprises the same components, construction, and/or functions in the same manner as the valves 236 and valve assemblies 204 shown in FIGS. 2, 10A-10B, and 11A-11B, as described above. Dependent upon the configuration or orientation of the irrigation valve assembly 1926, fluid is then directed either to the aspiration reservoir 1912 via a second irrigation path 1928, or through an irrigation outlet 1930 and out of the surgical cassette 1900 via a third irrigation path 1932. In certain embodiments, an irrigation pressure sensor 1924 is disposed within, or along, the third irrigation path 1932 and is configured to measure the fluidic pressure of the fluid as it exits the surgical cassette 1900.

In certain embodiments, as seen in FIG. 19B, the aspiration reservoir 1912 extends directly over one or more ports of the aspiration valve assembly 1906, which reduces any flow restriction between the aspiration reservoir 1912 and the aspiration valve assembly 1906 as caused by third aspiration path 1914, which may include one or more channels or other structures in FIG. 19A.

Figure 20B:
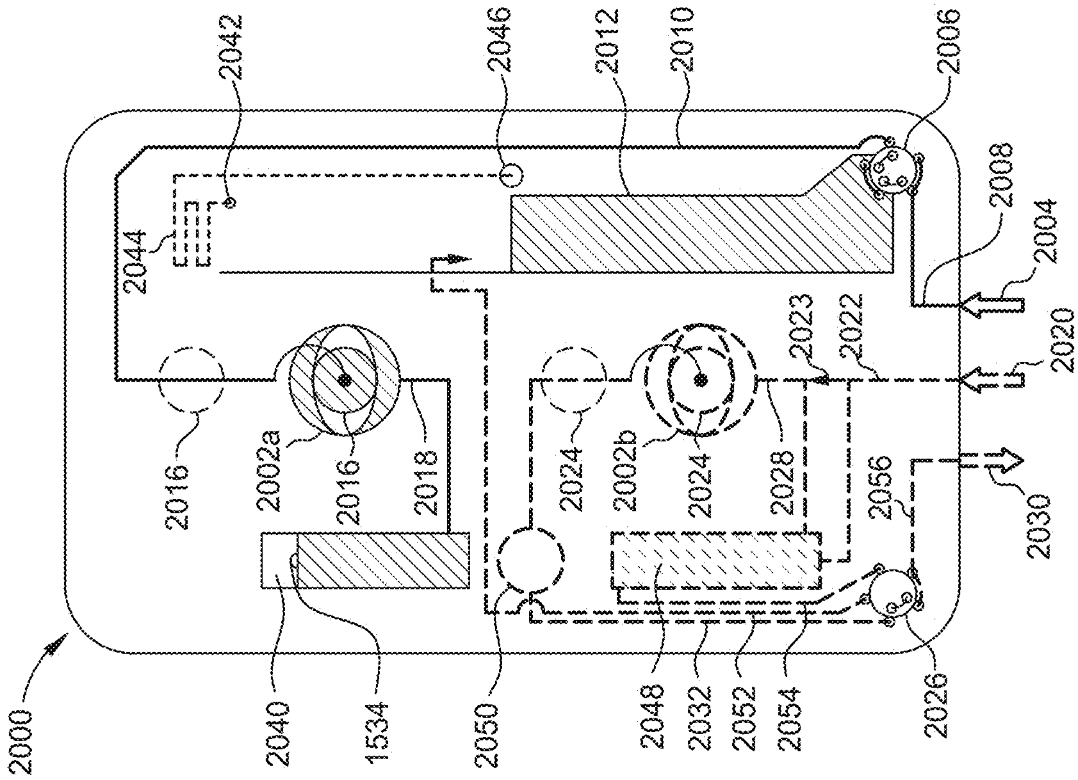
FIGS. 20A-20B is a schematic view of another simplified surgical cassette design, according to certain embodiments.
Figure 20A:
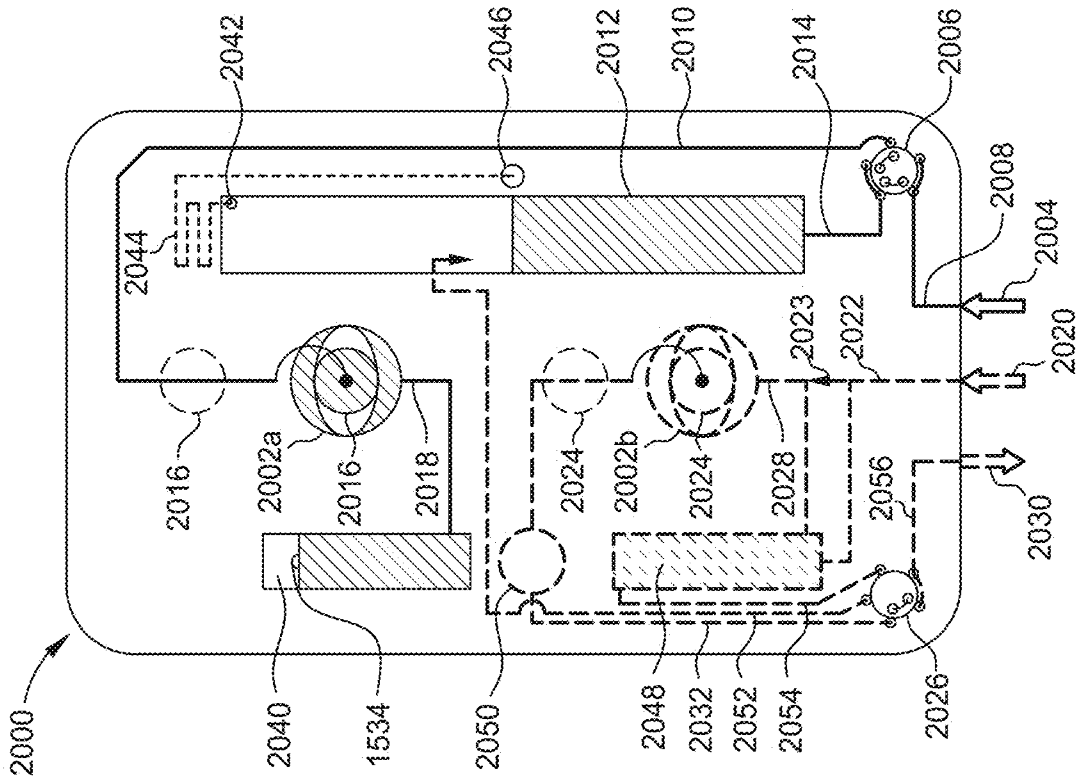

Turning now to FIGS. 20A-20B, a surgical cassette 2000 is shown. The surgical cassette 2000 comprises an aspiration path, an irrigation path, a first pump assembly 2002*a* provided specifically along the aspiration path, and a second pump assembly 2002*b* provided specifically along the irrigation path.

Fluid removed or suctioned from the eye of the patient enters an aspiration inlet 2004, where it is drawn through a first aspiration path 2008 to an aspiration valve assembly 2006 by a negative pressure provided by the first pump assembly 2002*a*. In certain embodiments, the aspiration valve assembly 2006 comprises the same components, construction, and/or functions in the same manner as the valves 236 and valve assemblies 204 shown in FIGS. 2, 10A-10B, and 11A-11B, as described above. Dependent upon the configuration or orientation of the aspiration valve assembly 2006, fluid is then directed either to the first pump assembly 2002*a* via a second aspiration path 2010, or directly into a venturi reservoir 2012 via a third aspiration path 2014. In certain embodiments, when fluid enters the first pump assembly 2002*a*, the fluid also passes through an aspiration pressure sensor 2016 disposed in the center of, or adjacent to (e.g., downstream or upstream of, as indicated by 2016 in phantom), the first pump assembly 2002*a* for monitoring fluidic pressure in the first pump assembly 2002*a* or second aspiration path 2010. The first pump assembly 2002*a* comprises the same components, construction, and/or functions in the same manner as the pump assemblies 202 shown in FIGS. 2, 5A-6B, and 9B as described above. After passing through the pump assembly 2002*a*, fluid is directed through a fourth aspiration path 2018 and into an aspiration reservoir 2040. Excess fluid within the aspiration reservoir 2040 drains to an outside drain bag or receptacle through a drain port 2034, while in certain embodiments, excess fluid within the venturi reservoir 2012 drains through an overflow port 2042, where it is directed through an overflow path 2044 to a venturi port 2046.

The irrigation path within the surgical cassette 2000 comprises, for example, an administration inlet 2020, where fluid that is to be sent to the eye of the patient first enters the surgical cassette 2000. In certain embodiments, the fluid passes through a first irrigation path 2022 before entering an irrigation reservoir 2048. Drawn by a negative pressure from the second pump assembly 2002*b*, the fluid is flowed to the second pump assembly 2002*b* from the irrigation reservoir 2048 via a second irrigation path 2028. Alternatively, in certain embodiments, fluid is flowed directly from the administration inlet 2020 to the second pump assembly 2002*b* without passing through the irrigation reservoir 2048, as indicated by arrow 2023. In such embodiments, first irrigation path 2022 and second irrigation path 2028 may be one and the same.

In certain embodiments, the fluid also passes through an irrigation pressure sensor 2024 disposed in the center of, or adjacent to (e.g., downstream or upstream of, as indicated by 2024 in phantom), the second pump assembly 2002*b*, which allows monitoring of fluidic pressure in the second pump assembly 2002*b* or second irrigation path 2028. Fluid then passes through a third irrigation path 2032 to an irrigation valve assembly 2026. In certain embodiments, the third irrigation path 2032 comprises a backup or redundant pressure sensor 2050 downstream of the irrigation pressure sensor 2024.

In certain embodiments, the irrigation valve assembly 2026 comprises the same components, construction, and/or functions in the same manner as the valves 236 and valve assemblies 204 shown in FIGS. 2, 10A-10B, and 11A-11B, as described above. Dependent upon the configuration or orientation of the irrigation valve assembly 2026, fluid is then directed either to the venturi reservoir 2012 via a fourth irrigation path 2052, back to the irrigation reservoir 2048 via a fifth irrigation path 2054, or through an irrigation outlet 2030 and out of the surgical cassette 2000 via a sixth irrigation path 2056. In certain embodiments, the third irrigation path 1932 comprises an irrigation pressure sensor 1924 configured to measure the fluidic pressure of the fluid as it exits the surgical cassette 1900.

In certain embodiments, as seen in FIG. 20B, the aspiration reservoir 2012 extends directly over one or more ports of the aspiration valve assembly 2006, which reduces any flow restriction between the aspiration reservoir 2012 and the aspiration valve assembly 2006 as caused by third aspiration path 2014, which may include one or more channels or other structures in FIG. 20A.

Figure 21B:
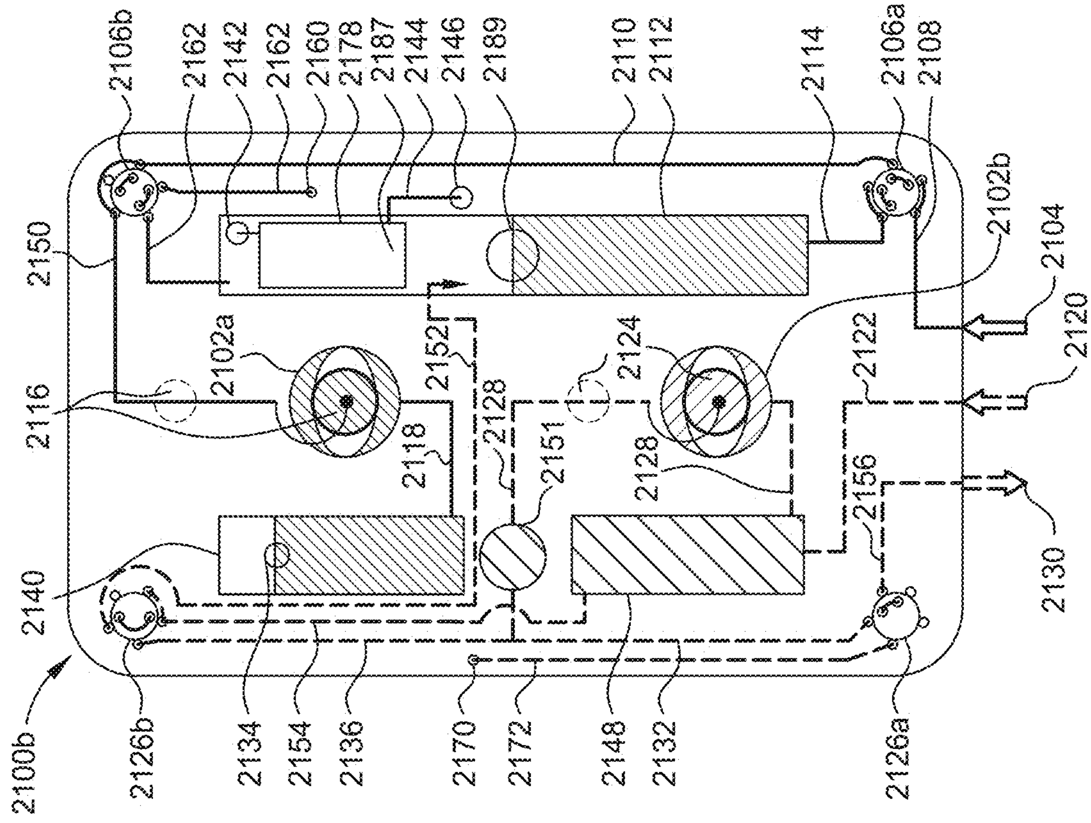
FIGS. 21A-21D are schematic views of another simplified surgical cassette design, according to certain embodiments.
Figure 21A:
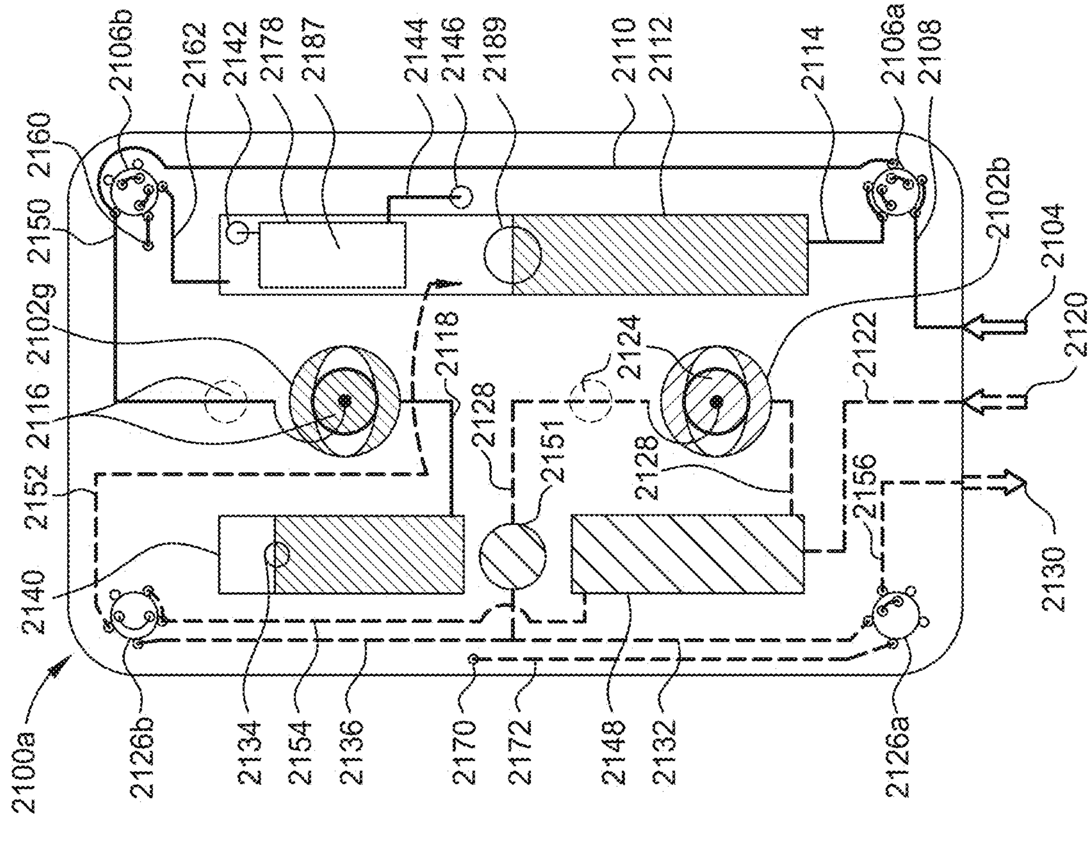

Turning to FIGS. 21A-21B, a surgical cassette 2100*a* is shown. The surgical cassette 2100*a* may be representative of, or be substantially similar in construction to, surgical cassette 200 as shown in FIGS. 2-10B. The surgical cassette 2100*a* comprises an aspiration path, an irrigation path, a first pump assembly 2102*a* provided specifically along the aspiration path, and a second pump assembly 2102*b* provided specifically along the irrigation path.

During use, fluid aspirated from the eye of the patient enters an aspiration inlet 2104, where it is drawn through a first aspiration path 2108 to an aspiration valve assembly 2106*a* and/or 2106*b* by a negative pressure provided by the first pump assembly 2102*a*. In certain embodiments, the aspiration valve assemblies 2106*a* and/or 2106*b* comprise the same components, construction, and/or function in the same manner as the valves 236 and valve assemblies 204 shown in FIGS. 2, 10A-10B, and 11A-11B, as described above. Dependent upon the configuration or orientation of the aspiration valve assemblies 2106*a* and 2106*b*, fluid is then directed either to the first pump assembly 2102*a* via a second aspiration path 2110 and a third aspiration path 2150, or directly into a venturi reservoir 2112 via fourth aspiration paths 2114. In certain embodiments, when fluid enters the first pump assembly 2102*a*, the fluid also passes through an aspiration pressure sensor 2116 disposed in the center of, or adjacent to (e.g., downstream or upstream of, as indicated by 2116 in phantom), the first pump assembly 2102*a* for monitoring fluidic pressure in the first pump assembly 2102*a* or third aspiration path 2150. The first pump assembly 2102*a* comprises the same components, construction, and/or functions in the same manner as the pump assemblies 202 shown in FIGS. 2, 5A-6B, and 9B as described above. After passing through the pump assembly 2102*a*, fluid is directed through a fifth aspiration path 2118 and into an aspiration reservoir 2140. Excess fluid within the aspiration reservoir 2140 drains to an outside drain bag or receptacle through a drain port 2134. In certain embodiments, excess fluid within the venturi reservoir 2112 drains through an overflow port 2142 and into a filter pocket 2178 having a filter 2187 disposed therein, where the fluid is filtered before being directed through an overflow path 2144 to a venturi port 2146. In certain embodiments, the venturi reservoir 2112 comprises a level sensor area 2189 disposed therein, or adjacent thereto, for monitoring fluid levels in the venturi reservoir 2112.

In certain embodiments, a suction fluid path 2162 is provided by the surgical cassette 2100*a*. In such embodiments, dependent upon the configuration or orientation of the valve assembly 2106*b*, fluids are suctioned through a suction port 2160 on a frontside of the surgical cassette 2100*a*. Driven by negative pressure provided by the first pump assembly 2102*a*, the fluids are passed through valve assembly 2106*b*, before being received in the venturi reservoir 2112.

The irrigation path within the surgical cassette 2100*a* comprises, for example, an administration inlet 2120, where fluid that is to be sent to the eye of the patient first enters the surgical cassette 2100*a*. The fluid passes through a first irrigation path 2122 before entering an irrigation reservoir 2148. Drawn by a negative pressure from the second pump assembly 2102*b*, the fluid is flowed to the second pump assembly 2102*b* via a second irrigation path 2128. In certain embodiments, the fluid also passes through an irrigation pressure sensor 2124 disposed in the center of, or adjacent to (e.g., downstream or upstream of, as indicated by 2124 in phantom), the second pump assembly 2102*b*, which allows monitoring of fluidic pressure in the second pump assembly 2102*b* or second irrigation path 2128. Fluid then passes through a third irrigation path 2132 to an irrigation valve assembly 2126*a* or a fourth irrigation path 2136 to an irrigation valve assembly 2126*b*. In certain embodiments, the second irrigation path 2128 comprises a backup or redundant pressure sensor 2151 downstream of the irrigation pressure sensor 2124. In certain embodiments, the irrigation valve assemblies 2126*a* and/or 2126*b* comprise the same components, construction, and/or function in the same manner as the valves 236 and valve assemblies 204 shown in FIGS. 2, 10A-10B, and 11A-11B, as described above. Dependent upon the configuration or orientation of the irrigation valve assemblies 2126*a* and 2126*b*, and driven by the second pump assembly 2102*b*, fluid is then directed either to the venturi reservoir 2112 via a fifth irrigation path 2152, back to the irrigation reservoir 2148 via a sixth irrigation path 2154, through an irrigation outlet 2130 and out of the surgical cassette 2100*a* via a seventh irrigation path 2156, or through an infusion port 2170 and out of the surgical cassette 2100*a* via an infusion fluid path 2172.

In certain embodiments, as seen in FIG. 21B, the aspiration reservoir 2112 extends directly over one or more ports of the aspiration valve assembly 2106, which reduces any flow restriction between the aspiration reservoir 2112 and the aspiration valve assembly 2106 as caused by fourth aspiration path 2114, which may include one or more channels or other structures in FIG. 21A.

Figure 21D:
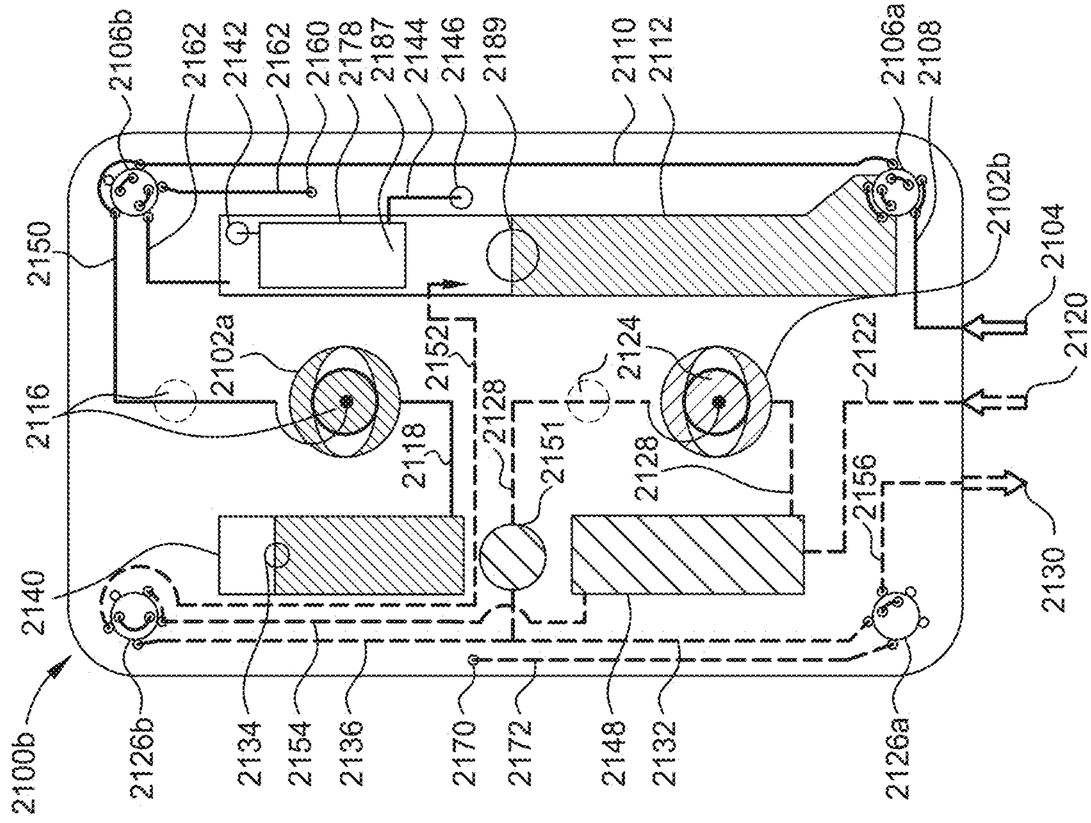
Figure 21C:
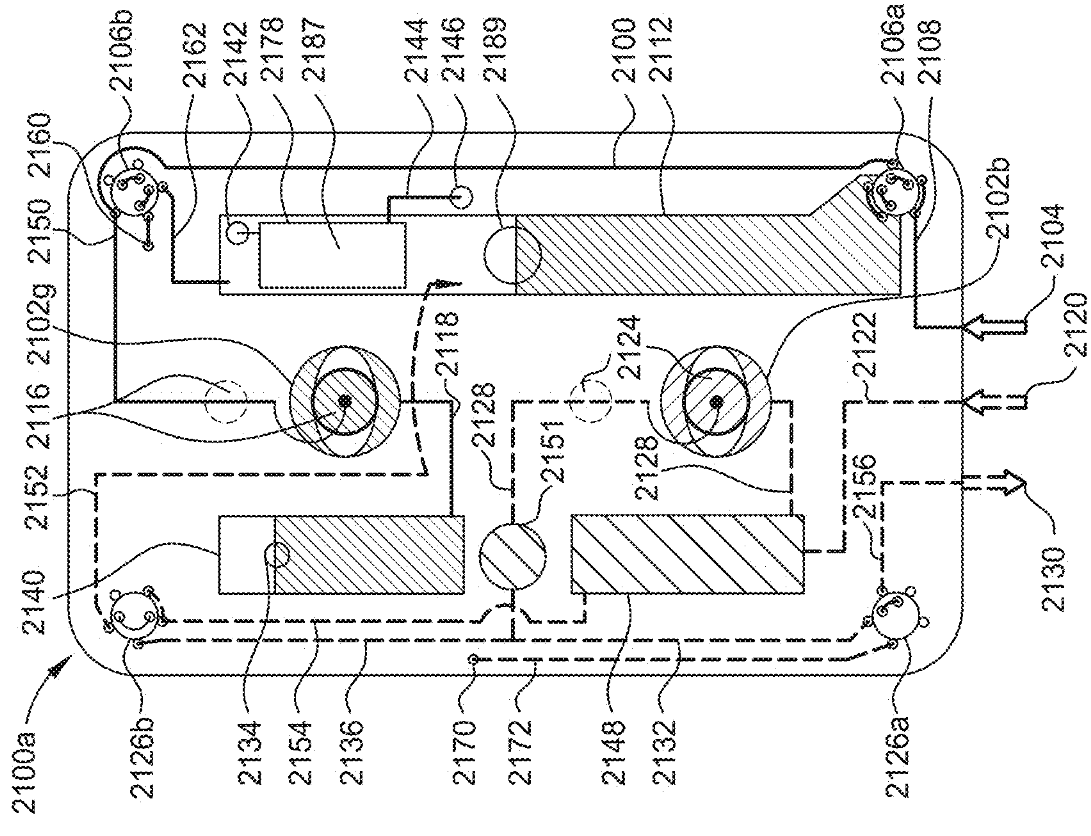

Turning to FIG. 21C, a surgical cassette 2100*b* is shown. The surgical cassette 2100*b* is substantially similar in function to surgical cassette 2100*a*, and thus, comprises similarly functioning components thereto. However, in terms of construction and physical arrangement, the surgical cassette 2100 may be representative of surgical cassette 1200 as shown in FIGS. 12-16B. More particularly, the surgical cassette 2100*b* may comprise of only a base (e.g., base 1500) and a cover (e.g., cover 1600), without a manifold, whereas surgical cassette 2100*a* may comprise of a base (e.g., base 206), a cover (e.g., cover 400), and a manifold (e.g., manifold 600). Accordingly, surgical cassette 2100*b* may be described as a "two-layer" construction, whereas surgical cassette 2100*a* may be described as a "three-layer" construction.

To facilitate the "two-layer" construction, the suction fluid path 2162 and infusion fluid path 2172 of surgical cassette 2100*b* may only extend within, or between, the base and corresponding cover of the surgical cassette 2100*b*. For example, infusion port 2170 and suction port 2160 of surgical cassette 2100*b* may be disposed through the cover of the surgical cassette 2100*b*, and thus, infusion fluid path 2172 and suction fluid path 2162 of surgical cassette 2100*b* may only need to extend within, or between, the base and cover to fluidly couple with the infusion port 2170 and suction port 2160, respectively. Conversely, infusion port 2170 and suction port 2160 of surgical cassette 2100*a* may be disposed through a manifold of the surgical cassette 2100*a*, and thus, infusion fluid path 2172 and suction fluid path 2162 of surgical cassette 2100*a* may need to extend within, or between, the base, the cover, and the manifold to fluidly couple with the infusion port 2170 and suction port 2160, respectively. Further, as shown in FIGS. 21C and 21D, fifth irrigation path 2152 is formed or disposed only between the cover and base of the surgical cassette 2100*b*, and does not need to extend "vertically" to bypass other flow paths, thereby creating a "two-dimensional" or "2D" pathway. Conversely, in FIGS. 21A and 21B, fifth irrigation path 2152 crosses vertically into the manifold of surgical cassette 2100*a* to bypass fifth aspiration path 2118 and/or other flow paths. While only the suction fluid path 2162, infusion fluid path 2172, and irrigation path 2152 are used as examples to describe the "three-layer" and "two-layer" constructions of surgical cassettes 2100*a* and 2100*b*, other fluid pathways and/or fluid lines within the surgical cassettes 2100*a* and 2100*b* may also have similar three- or two-layer arrangements.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A surgical cassette for ophthalmic irrigation or aspiration during a surgical procedure, the surgical cassette comprising:

a base, comprising:

at least one pump assembly disposed in the base;

a plurality of channels configured to be in fluid communication with at least one of the at least one pump assembly or an external source of pressure or vacuum; and one or more valve assemblies disposed in the base and configured to control fluid communication between the plurality of channels of the base; and a cover coupled to the base, the cover comprising at least one port in fluid communication with at least one of the plurality of channels of the base; and a manifold coupled to the cover, the manifold forming at least one channel with an outer surface of the cover, wherein the manifold comprises:

an infusion connector in fluid communication with an infusion channel defined between the manifold and the cover; and a suction connector in fluid communication with a suction channel defined between the manifold and the cover.

2. The surgical cassette of claim 1, wherein the plurality of channels comprises a plurality of sidewalls that are sealingly enclosed through contact between a corresponding plurality of faces extending from an inner surface of the cover.

3. The surgical cassette of claim 1, wherein the base further comprises:

a waste reservoir in fluid communication with at least one of the plurality of channels; and an irrigation reservoir in fluid communication with at least one other of the plurality of channels.

4. The surgical cassette of claim 1, wherein each of the at least one pump assembly is coupled to a corresponding well, each well comprising:

a first pump channel circumferentially disposed around the well;

a second pump channel disposed adjacent to the first pump channel;

a bottom surface disposed radially inward from the first and second pump channels; and an angled surface disposed between the bottom surface of the first and second pump channels.

5. A surgical cassette for ophthalmic irrigation or aspiration during a surgical procedure, the surgical cassette comprising:

a base, comprising:

at least one pump assembly disposed in the base;

a plurality of channels configured to be in fluid communication with at least one of the at least one pump assembly or an external source of pressure or vacuum; and one or more valve assemblies disposed in the base and configured to control fluid communication between the plurality of channels of the base; and a cover coupled to the base, the cover comprising at least one port in fluid communication with at least one of the plurality of channels of the base, wherein the cover comprises:

a bypass channel disposed on an outer surface of the cover;

a bypass inlet defined in one end of the bypass channel, the bypass inlet in fluid communication with at least one of the plurality of channels of the base; and a bypass outlet defined in an opposing end of the bypass channel, the bypass outlet in fluid communication with a venturi reservoir disposed within the base.

6. The surgical cassette of claim 5, wherein the plurality of channels comprises a plurality of sidewalls that are sealingly enclosed through contact between a corresponding plurality of faces extending from an inner surface of the cover.

7. The surgical cassette of claim 5, wherein the base further comprises:

a waste reservoir in fluid communication with at least one of the plurality of channels; and an irrigation reservoir in fluid communication with at least one other of the plurality of channels.

8. A surgical cassette for ophthalmic irrigation or aspiration during a surgical procedure, the surgical cassette comprising:

a base, comprising:

at least one pump assembly disposed in the base;

a plurality of channels configured to be in fluid communication with at least one of the at least one pump assembly or an external source of pressure or vacuum; and one or more valve assemblies disposed in the base and configured to control fluid communication between the plurality of channels of the base;

a cover coupled to the base, the cover comprising at least one port in fluid communication with at least one of the plurality of channels of the base; and a manifold coupled to the cover, the manifold forming at least one channel with an outer surface of the cover, wherein the base comprises:

a venturi reservoir in fluid communication with at least one of the plurality of channels; and a level sensor area configured to indicate a level of fluid within the venturi reservoir.

9. The surgical cassette of claim 8, wherein the manifold comprises a light deflector configured to deflect light from entering the venturi reservoir.

10. The surgical cassette of claim 8, wherein the manifold is comprised of light blocking ink configured to block light from entering the venturi reservoir.

11. The surgical cassette of claim 8, wherein the plurality of channels comprises a plurality of sidewalls that are sealingly enclosed through contact between a corresponding plurality of faces extending from an inner surface of the cover.

12. The surgical cassette of claim 8, wherein the base further comprises:

a waste reservoir in fluid communication with at least one of the plurality of channels; and an irrigation reservoir in fluid communication with at least one other of the plurality of channels.

13. A surgical cassette for ophthalmic irrigation or aspiration during a surgical procedure, the surgical cassette comprising:

a base, comprising:

at least one pump assembly disposed in the base, wherein each of the at least one pump assembly is coupled to a corresponding well, each well comprising:

a first pump channel circumferentially disposed around the well;

a second pump channel disposed adjacent to the first pump channel;

a bottom surface disposed radially inward from the first and second pump channels, wherein the bottom surface comprises a sensor inlet and a sensor outlet defined therein, wherein at least the sensor inlet comprises an elongated opening; and an angled surface disposed between the bottom surface of the first and second pump channels;

a plurality of channels configured to be in fluid communication with at least one of the at least one pump assembly or an external source of pressure or vacuum; and one or more valve assemblies disposed in the base and configured to control fluid communication between the plurality of channels of the base; and a cover coupled to the base, the cover comprising at least one port in fluid communication with at least one of the plurality of channels of the base.

14. A surgical cassette for ophthalmic irrigation or aspiration during a surgical procedure, the surgical cassette comprising:

a base, comprising:

at least one pump assembly disposed in the base, wherein each of the at least one pump assembly is coupled to a corresponding well, each well comprising:

a first pump channel circumferentially disposed around the well;

a second pump channel disposed adjacent to the first pump channel;

a bottom surface disposed radially inward from the first and second pump channels; and an angled surface disposed between the bottom surface of the first and second pump channels, wherein the angled surface comprises a plurality of keyways configured to accommodate a diaphragm retaining ring therein;

a plurality of channels configured to be in fluid communication with at least one of the at least one pump assembly or an external source of pressure or vacuum; and one or more valve assemblies disposed in the base and configured to control fluid communication between the plurality of channels of the base; and a cover coupled to the base, the cover comprising at least one port in fluid communication with at least one of the plurality of channels of the base.

15. A surgical cassette for ophthalmic irrigation or aspiration during a surgical procedure, the surgical cassette comprising:

a base, comprising:

at least one pump assembly disposed in the base, wherein each of the at least one pump assembly is coupled to a corresponding well, each well comprising:

a first pump channel circumferentially disposed around the well;

a second pump channel disposed adjacent to the first pump channel;

a bottom surface disposed radially inward from the first and second pump channels; and an angled surface disposed between the bottom surface of the first and second pump channels, wherein the first and second pump channels each comprise:

a pump inlet defined in one end;

a pump outlet defined in an opposing end; and a pump channel trough disposed through an arc length of the first and second pump channel and adjacent to either the pump inlet or the pump outlet;

a plurality of channels configured to be in fluid communication with at least one of the at least one pump assembly or an external source of pressure or vacuum; and one or more valve assemblies disposed in the base and configured to control fluid communication between the plurality of channels of the base; and a cover coupled to the base, the cover comprising at least one port in fluid communication with at least one of the plurality of channels of the base.

16. A surgical cassette for ophthalmic irrigation or aspiration during a surgical procedure, the surgical cassette comprising:

a base, comprising:

at least one pump assembly disposed in the base;

a plurality of channels configured to be in fluid communication with at least one of the at least one pump assembly or an external source of pressure or vacuum; and one or more valve assemblies disposed in the base and configured to control fluid communication between the plurality of channels of the base; and a cover coupled to the base, the cover comprising at least one port in fluid communication with at least one of the plurality of channels of the base, wherein the cover comprises a filter pocket defined in an outer surface of the cover, the filter pocket comprising:

a vacuum port in fluid communication with a venturi reservoir and in pressure communication with an external vacuum source; and a filter pocket drain in fluid communication with the venturi reservoir.

17. The surgical cassette of claim 16, further comprising a manifold coupled to the cover, the manifold forming at least one channel with the outer surface of the cover, wherein the manifold comprises a plurality of filter support ribs coupled to an inner surface of the manifold, the plurality of filter support ribs being aligned with the filter pocket when the manifold is coupled to the cover.

18. The surgical cassette of claim 16, wherein the plurality of channels comprises a plurality of sidewalls that are sealingly enclosed through contact between a corresponding plurality of faces extending from an inner surface of the cover.

19. The surgical cassette of claim 16, wherein the base further comprises:

a waste reservoir in fluid communication with at least one of the plurality of channels; and an irrigation reservoir in fluid communication with at least one other of the plurality of channels.

20. The surgical cassette of claim 16, further comprising:

a manifold coupled to the cover, the manifold forming at least one channel with the outer surface of the cover, wherein the manifold comprises at least one of a light deflector configured to deflect light from entering the venturi reservoir or a light blocking ink configured to block light from entering the venturi reservoir.

* * * * *